(12) United States Patent
Connell et al.

(10) Patent No.: US 10,973,819 B2
(45) Date of Patent: Apr. 13, 2021

(54) SMALL MOLECULES INHIBITORS OF RAD51

(71) Applicant: The University of Chicago, Chicago, IL (US)

(72) Inventors: Philip Connell, Chicago, IL (US); Wei Lv, Chicago, IL (US); Brian Budke, Chicago, IL (US); Alan Kozikowski, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 16/081,662

(22) PCT Filed: Mar. 2, 2017

(86) PCT No.: PCT/IB2017/051227
§ 371 (c)(1),
(2) Date: Aug. 31, 2018

(87) PCT Pub. No.: WO2017/149493
PCT Pub. Date: Sep. 8, 2017

(65) Prior Publication Data
US 2019/0083491 A1   Mar. 21, 2019

Related U.S. Application Data

(60) Provisional application No. 62/302,569, filed on Mar. 2, 2016.

(51) Int. Cl.
*A61K 31/4985* (2006.01)
*A61K 45/06* (2006.01)
(Continued)

(52) U.S. Cl.
CPC ...... *A61K 31/4985* (2013.01); *A61K 31/5377* (2013.01); *A61K 45/06* (2013.01); *A61P 35/00* (2018.01); *C07D 487/04* (2013.01)

(58) Field of Classification Search
CPC ............ A61K 31/4985; A61K 31/5377; A61K 45/06; A61P 35/00
See application file for complete search history.

(56) References Cited

U.S. PATENT DOCUMENTS

| 4,200,750 A | 4/1980 | Warner, Jr. et al. |
| 2009/0239818 A1* | 9/2009 | Cheng ............... A61K 31/706 514/52 |

(Continued)

FOREIGN PATENT DOCUMENTS

| EP | 2099442 | 11/2014 |
| RU | 2335335 | 10/2008 |
| WO | WO 2015/017866 | 2/2015 |

OTHER PUBLICATIONS

Dorwald (Side Reaction in Organic Synthesis: A Guide to Successful Synthesis Design, Weinheim: WILEY-VCH, Verlag GmbH & Co., KGaA, 2002, Preface).*

(Continued)

*Primary Examiner* — Anna Pagonakis
(74) *Attorney, Agent, or Firm* — Norton Rose Fulbright US LLP

(57) ABSTRACT

Embodiments concern methods and small molecule compositions for selectively inhibiting RAD51-mediated D-loop formation while preserving RAD51's ability to form nucleoprotein filaments. The selective RAD51 D-loop formation activity inhibitors DNA repair while minimizing replication-associated toxicity in normal tissue.

7 Claims, 4 Drawing Sheets

(51) Int. Cl.
C07D 487/04 (2006.01)
A61P 35/00 (2006.01)
A61K 31/5377 (2006.01)

(56) References Cited

U.S. PATENT DOCUMENTS

2010/0240642 A1 9/2010 Oplinger et al.
2011/0275643 A1 11/2011 Liou et al.

OTHER PUBLICATIONS

Desplat et al. Synthesis of new pyrrolo[1,2-a]quinoxaline derivatives as potential inhibitors of Akt kinase. Journal of Enzyme Inhibition and Medicinal Chemistry, Oct. 2008, 23(5): 648-658.*
Bennardo et al., "Alternative-NHEJ is a Mechanistically Distinct Pathway of Mammalian Chromosome Break Repair," PLoS Genet., 2008, 4:e1000110.
Budke et al., "An Optimized RAD51 Inhibitor That Disrupts Homologous Recombination without Requiring Michael Acceptor Reactivity," J. Med. Chem., 2013, 56:254-263.
Budke et al., "Real-Time Soluation Measurement of Rad51- and Reca-Mediated Strand Assimilation without Background Annealing," Nucleic Acids Res., 2013, 41:e130.
Budke et al., "RI-1: A chemical inhibitor of RAD51 that disrupts homologous recombination in human cells," Nucleic Acids Res., 2012, 40:7347-7357.
Campiani et al., "Pyrroloquinoxaline Derivatives as High-Affinity and Selective 5-HT$_3$ Receptor Agonists: Synthesis, Further Structure-Activity Relationships, and Biological Studies," J. Med. Chem., 1999, 42:4362-4379.
Carvalho et al., "Targeting Homologous Recombination-Mediated DNA Repair in Cancer," Expert. Opin. Ther. Targets., 2014, 18:427-458.
Cheng et al., "Design and synthesis of (2-(5-chloro-2,2-dimethyl-2,3-dihydrobenzofuran-7-yl)cyclopropyl)methanamine as a selective serotonin 2C agonist" Tetrahedron Lett., 2015, 56:3420-3422.
Cheng et al., "Optimization of 2-Phenylcyclopropylmethylamines as Selective Serotonin 2C Receptor Agonists and Their Evaluation as Potential Antipsychotic Agents," J. Med. Chem., 2015, 58:1992-2002.
Desplat et al., "Synthesis of New Pyrrolo[1,2-a]quinoxaline Derivatives as Potential Inhibitors of Akt Kinase," Journal of Enzyme Inhibition and Medicinal Chemistry, 2008, 23(5):648-658.
Guillon et al., "Synthesis, analytical Behavior and Biological Evaluation of New 4-Substituted Pyrrolo[1,2-α] Quinoxalines as Antileishmanial Agents," Bioorg. Med. Chem., 2007, 15:194-210.
Guillon et al., "Synthesis, antimalarial activity, and molecular modeling of new pyrrolo[1,2-a]quinoxalines, bispyrrolo[1,2-a]quinoxalines, bispyrido[3,2-e]pyrrolo[1,2-a]pyrazines, and bispyrrolo[1,2-a]thieno[3,2-e]pyrazines.," J. Med. Chem., 2004, 47: 1997-2009.
Hansen et al., "The role of RAD51 in Etoposide (VP16) resistance in small cell lung cancer," Int. J. Cancer, 2003, 105:472-479.
Hine et al., "Use of the Rad51 promoter for targeted anti-cancer therapy," Proc. Natl. Acad. Sci. U.S.A., 2008, 105:20810-20815.
Huang et al., "Inhibition of Homologous Recombination in Human Cells by Targeting Rad51 Recombinase," J. Med. Chem., 2012, 55:3011-3020.
Huang et al., "Targeting the Homologous Recombination Pathway by Small Molecule Modulators," Bioorg. Med. Chem. Lett., 2014, 24:3006-3013.
International Search Report and Written Opinion issued in International Patent Application No. PCT/IB2017/051227, dated Jun. 7, 2017.

Ishida et al., "DIDS, a Chemical Compound That Inhibits Rad51-Mediated Homologous Pairing and Strand Exchange,"Nucleic Acids Res., 2009, 37:3367-3376.
Jayathilaka et al., "A Chemical Compound That Stimulates the Human homologous Recombination Protein RAD51," Proc. Natl. Acad. Sci. U.S.A., 2008, 105:15848-15853.
Kalinin et al., "Pyrrolo{a,2-α]Quinozalines Based on Pyrroles (Review)" Chemistry of Heterocyclic Compounds, 2011, 46(12): 1423-1442.
Klein, "The consequence of Rad51 overexpression for normal and tumor cells," DNA Repair (AMST), 2008, 7:686-693.
Liu et al., "XRCC2 and XRCC3, New human Rad51-family members, promote chromosome stability and protect against DNA cross-links and other damages," Mol. Cell, 1998, 1:783-793.
Morgan et al., "Inhibitors of Tubulin Assembly Identified through Screening a Compound Library," Chem Biol Drug Des., 2008, 72(6):513-524.
Murahari et al., "Current Overview on the Usage of Poly(ADP-ribose)polymerase(PARP) Inhibitors in Treating Cancer," Clinical Cancer Drugs, 2014, 1(2):127-148.
Preetam et al., "An Eco-Friendly Pictet Spengler Approach to Pyrrolo- and Indolo[1,2-a]Quinoxalines Using P-Dodecylbenzenesulfonic Acid as an Efficient Bronsted Acid Catalyst," RSC Advances, 2015, 5:21843-21853.
Pubchem ID 103514671 "4-Phenylpyrrolo[1,2-A]Quinoxaline," Retrieved from the Internet on May 22, 2017, URL<https://pubhem.ncbi.nlm.nih.gov/substance/103514671#section=RelatedRecords>.
Pubchem ID 49794744, "N-Ethyl-4-(6-methylquinoline-2-yl)aniline" 2010, 9 pages.
Raderschall et al., "Elevated Levels of Rad51 Recombination Protein in Tumor Cells," Cancer Res., 2002, 62:219-225.
Renodon-Corniere et al., "New potential therapeutic approaches in targeting Rad51-Dependent homologous recombination," New Research Directions in DNA repair, 2013.
Russel et al., "Gleevec-mediated inhibition of RAD51 expression and enhancement of tumor cell radiosensitivity," Cancer Res., 2003, 63:7377-7383.
Schlacher et al., "Double-Strand Break Repair-Independent Role for BRCA2 in Blocking Stalled Replication Fork degradation by MRE11," Cell, 2011, 145:529-542.
Slupianek et al., "BCR/ABL regulates RecA homologs, resulting in drug resistance," Mol. Cell, 2001, 8:795-806.
Takaku et al., "Halenaquinone, a Chemical Compound That Specifically Inhibits the Secondary DNA Binding of RAD51," Genes Cells, 2011, 16:427-436.
Takata et al., "Chromosome instability and defective recombinatorial repair in knockout mutants of the five Rad51 paralogs" Mol. Cell. Bio., 2001, 21:2858-2866.
Tebbs et al., "Correction of chromosomal instability and sensitivity to diverse mutagens by a clones cDNA of the XRCC3 DNA repair gene," Proc. Natl. Acad. Sci. U.S.A., 1995, 62:6534-6385.
Thompson et al., "Homologous recombinatorial repair of DNA ensures mammalian chromosome stability" Mutat. Res., 2001, 477:131-153.
Vispe et al., "Overexpression of Rad51 protein stimulates homologous recombination and increases resistance of mammalian cells to ionizing radiation" Nucleic Acids Res., 1998, 26:2859-2864.
Wang et al., "Iodine-Catalyzed Facile Synthesis of Pyrrolo- and Indolo[1,2-a]Quinoxalines," Asian Journal of Organic Chemistry, 2015, 4:866-869.
Ying et al., "Mre11-Dependent Degradation of Stalled DNA Replication Forks in Prevented by BRCA2 and PARP1" Cancer Res, 2012, 72:2814-2821.

* cited by examiner

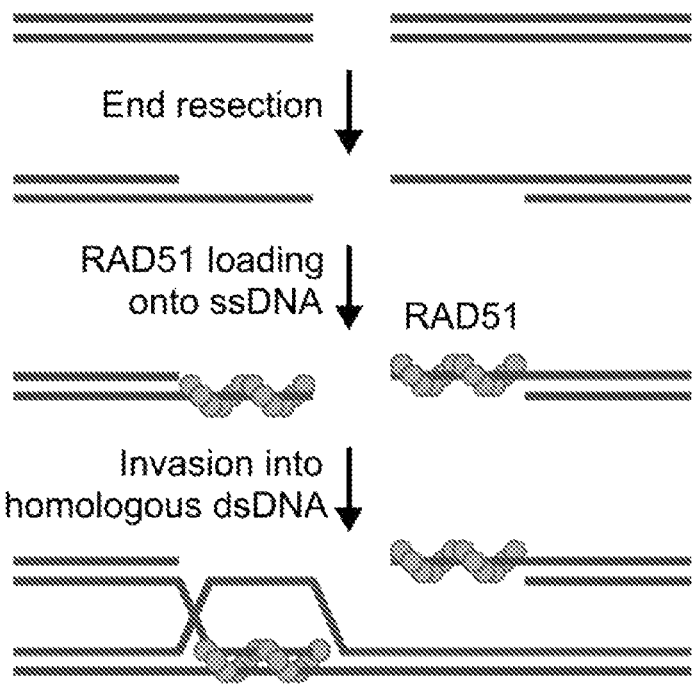
FIG. 1
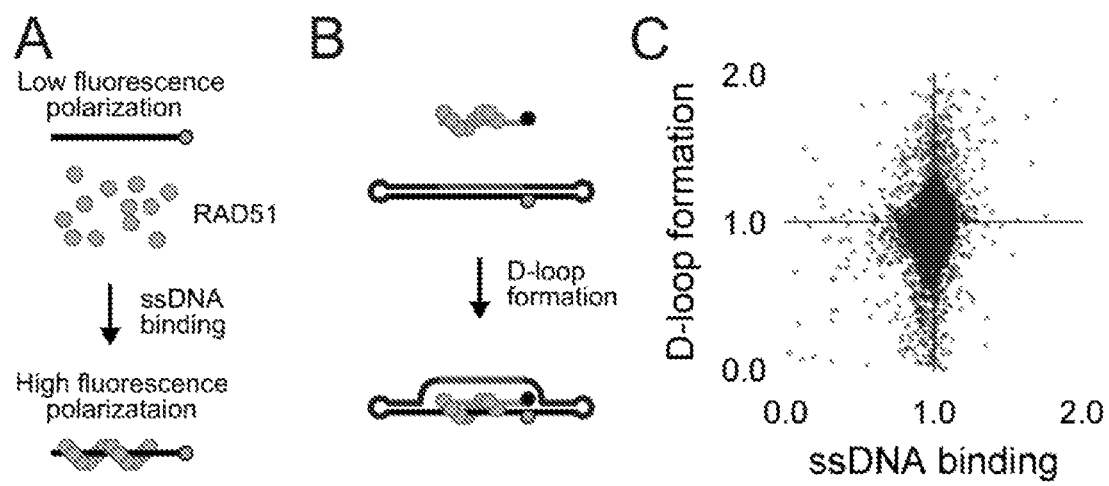
FIG. 2A-C

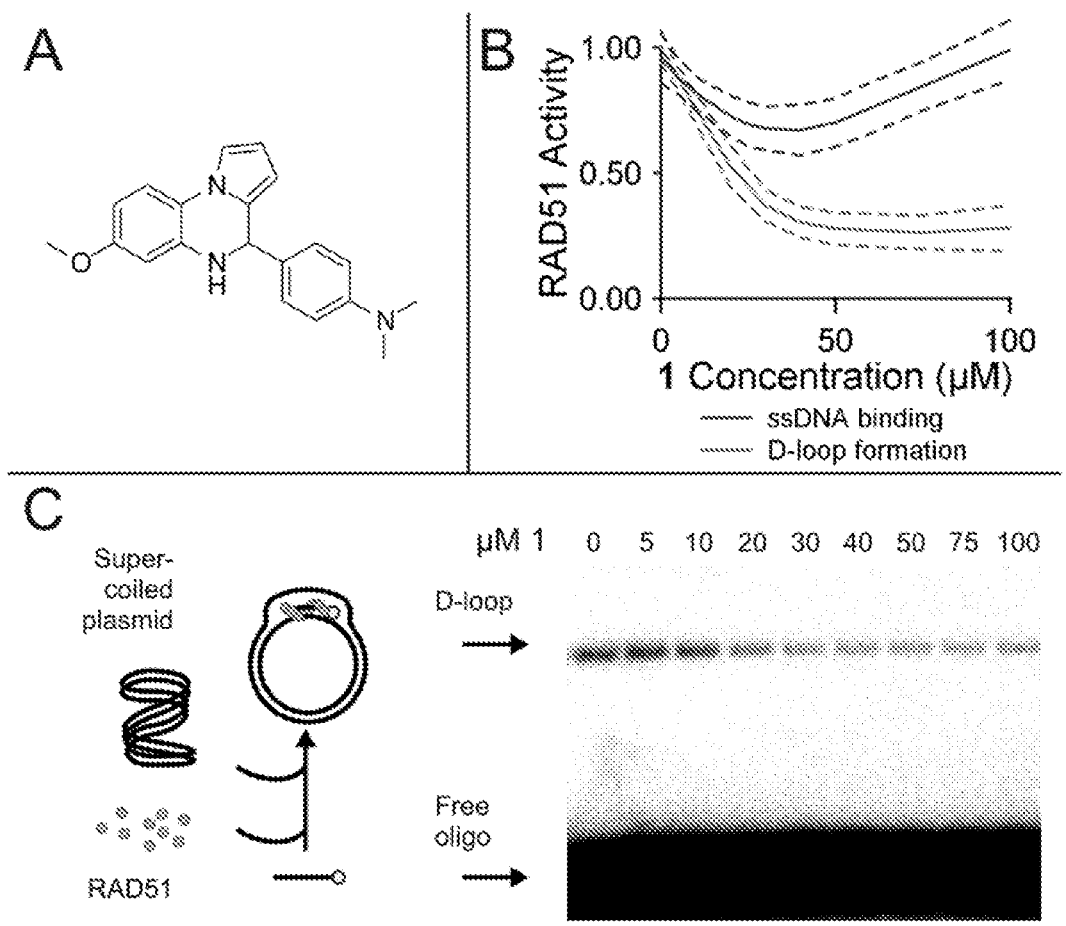
FIG. 3A-C
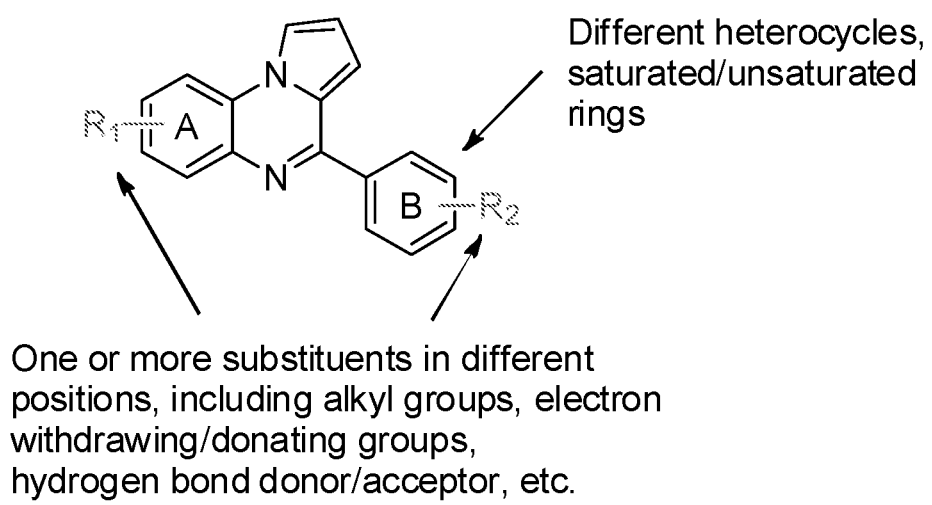
FIG. 4

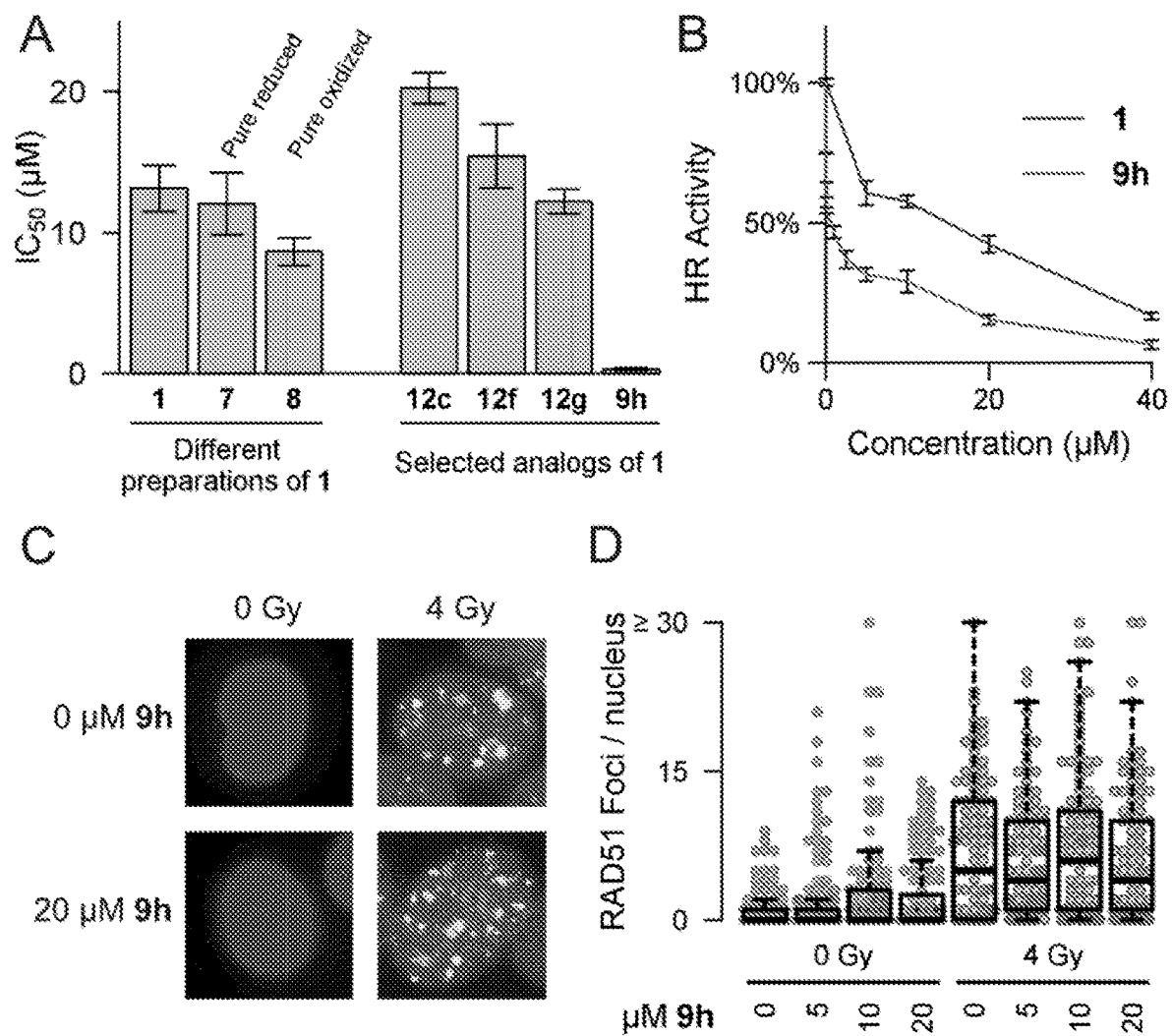
FIG. 5A-D

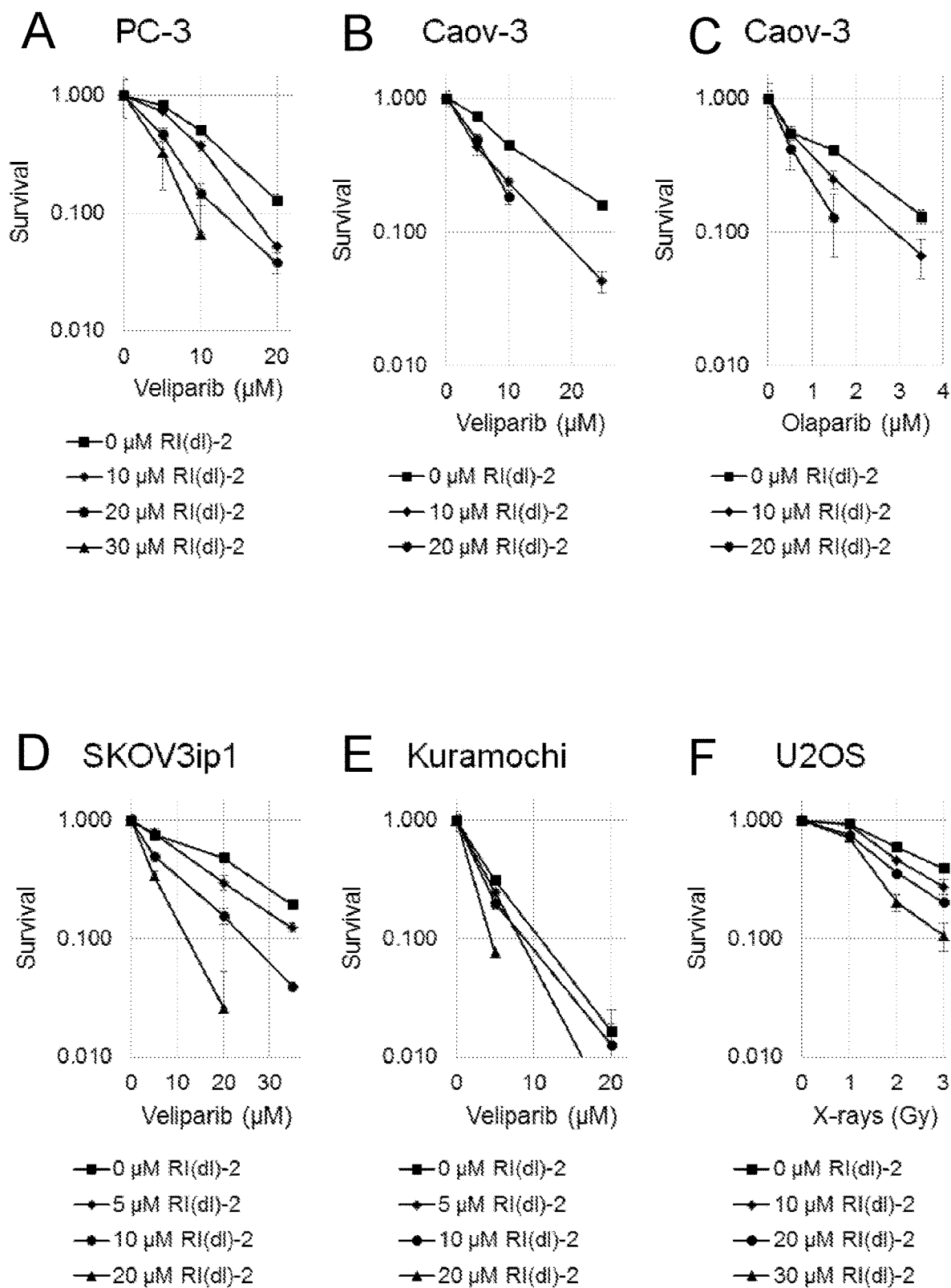
FIG. 6A-F

SMALL MOLECULES INHIBITORS OF RAD51

CROSS-REFERENCE TO RELATED APPLICATIONS

This application is a national phase application under 35 U.S.C. § 371 of International Application No. PCT/IB2017/051227 filed Mar. 2, 2017, which claims the benefit of priority of U.S. Provisional Patent Application No. 62/302,569 filed Mar. 2, 2016. The entire contents of each of the above-referenced disclosures are specifically incorporated herein by reference.

BACKGROUND OF THE INVENTION

1. Field of the Invention

The present invention relates generally to the fields of biochemistry, cell biology, organic chemistry, and oncology. More specifically, it concerns small molecules that inhibit RAD51 D-loop activity without affecting RAD51 ssDNA binding activity, and methods for their use as anti-cancer agents.

2. Description of Related Art

Homologous recombination (HR) is an evolutionarily conserved DNA repair process, which repairs DNA double strand breaks (DSBs) and promotes tolerance of inter-strand DNA cross-links (ICLs). Unlike the error-prone non-homologous end-joining (NHEJ) pathway of DSB rejoining, HR faithfully repairs DNA damage by utilizing an undamaged homologous DNA template to guide the repair process.[1, 2] An initial step of HR involves nuclease processing that generates a 3' single-stranded DNA (ssDNA) tail at the site of DNA damage. The ssDNA is then coated with RAD51 protein to form a helical nucleoprotein filament. This resulting nucleoprotein filament subsequently searches for a homologous DNA sequence and invades it to form a joint molecule intermediate, termed a D-loop. Finally, with the assistance of other related HR proteins, accurate DNA synthesis is performed using the undamaged homologous sequence as a template.

Since HR facilitates cellular recovery from harmful DNA lesions, cells with deficient HR functionality are especially vulnerable to radiotherapy and chemotherapeutic agents that generate DSBs or DNA replication-blocking lesions.[2-4] RAD51, the central protein of HR, is over-expressed in various types of human cancer cells.[5, 6] These high expression levels of RAD51 can elevate HR efficiency in cancer cells, thereby inducing cellular resistance to DNA-damaging chemotherapy and radiotherapy.[7-10] Inhibition of RAD51 by antisense RNAs or RAD51 inhibitors are reported to enhance the sensitivity of cancer cells to chemotherapy and radiotherapy.[11-13] These observations support the concept of RAD51 as a therapeutic target and the development of small molecule therapeutics to sensitize tumors.[14-16]

Although several small molecule RAD51 inhibitors have been developed, most of these inhibitors act by preventing the formation of RAD51-ssDNA nucleoprotein filaments.[13, 14, 16-19] One possible exception is halenaquinone, a chemical purported to specifically inhibit D-loop formation by RAD51.[20] However, halenaquinone also reduces the sub-nuclear appearance of RAD51 foci at DSB sites in cells, which raises questions as to its mechanistic interaction with RAD51 in cells.

In addition to its function in HR, RAD51 filaments also serve an important function at stalled DNA replication forks.[21, 22] These RAD51 nucleoprotein filaments protect the ssDNA from extensive nuclease processing, thereby aiding in replication and preserving genomic integrity. Since most RAD51 inhibitors act by preventing the formation of RAD51 nucleoprotein filaments on ssDNA, they are expected to inhibit both HR and replication fork stabilization activities of RAD51. As such, their use is predicted to generate unintended toxicity to normal cells by interrupting this centrally-important function in normal replication. Selectively inhibiting RAD51-mediated D-loop formation while preserving RAD51's ability to form nucleoprotein filaments may target DNA repair while minimizing replication-associated toxicity in normal tissue.

SUMMARY OF THE INVENTION

Embodiments are based on the identification and characterization of compounds that inhibit RAD51's D-loop activity while having minimal effects on RAD51's ssDNA binding activity. Therefore, there are methods and compositions involving compounds that selectively inhibit RAD51 D-loop activity. In certain embodiments, methods and compositions concern compounds that selectively decrease, inhibit, or reduce RAD51 D-loop activity.

In certain embodiments, there are methods for inhibiting RAD51 D-loop formation activity in a cell comprising providing to the cell an effective amount of a RAD51 modulator, wherein the inhibitor is a small molecule that directly inhibits RAD51 D-loop formation. This means that small molecules alter the D-loop formation activity of RAD51 protein (or a RAD51 protein analog or homolog) directly (i.e., RAD51 activity decreases when the RAD51 protein is contacted or incubated with the small molecule), and not indirectly, such as by altering the expression level of RAD51. In some embodiments, there are methods for inhibiting RAD51-mediated D-loop formation while preserving RAD51's ability to form nucleoprotein filaments and RAD51's ability to bind single stranded DNA. In certain aspects, small molecules are presented which selectively inhibit RAD51's D-loop formation activity over RAD51's ability to form nucleoprotein filaments and RAD51's ability to bind single stranded DNA.

In some embodiments, the methods and compositions concern a compound that is an inhibitor of RAD51 D-loop activity, meaning that the compound directly decreases, inhibits, and/or attenuates RAD51 D-loop formation activity when the RAD51 protein is exposed to the compound. The terms "inhibitor" and "antagonist" are used interchangeably herein.

Therefore, embodiments cover a number of methods involving a RAD51 D-loop-formation inhibitor, that decrease, inhibit or reduce RAD51 D-loop-formation activity by or by at least about 10, 15, 20, 25, 30, 35, 40, 45, 50, 55, 60, 65, 70, 75, 80, 85, 90, 95, or 100% (and any range derivable therein) compared to RAD51 D-loop-formation activity in the absence of the RAD51 D-loop-formation inhibitor. Therefore, in some embodiments, there are methods for inhibiting RAD51 D-loop-formation in a cell comprising providing to the cell an effective amount of a small molecule that directly inhibits RAD51 D-loop-formation activity in a cell. In particular embodiments, the RAD51 D-loop-formation inhibitor decreases RAD51 filament formation when the inhibitor is incubated with RAD51 protein under conditions to promote filament formation. In certain other embodiments, the RAD51 D-loop-formation inhibitor does not not inhibit RAD51's ability to bind single stranded DNA (ssDNA) or RAD51's ability to form nucleoprotein filaments.

A RAD51 D-loop formation inhibitor is a compound that acts in conjunction with RAD51 protein to inhibit, attenuate or decrease the D-loop formation activity of the RAD51 protein. In some embodiments, the RAD51 D-loop formation inhibitors selectively inhibit RAD51 D-loop formation activity over RAD51's ability to bind single stranded DNA (ssDNA) and RAD51's ability to form nucleoprotein filaments. In certain embodiments the RAD51 D-loop formation activity inhibitor is a small molecular weight compound. In specific embodiments, the RAD51 D-loop formation activity inhibitor is a compound of formula:

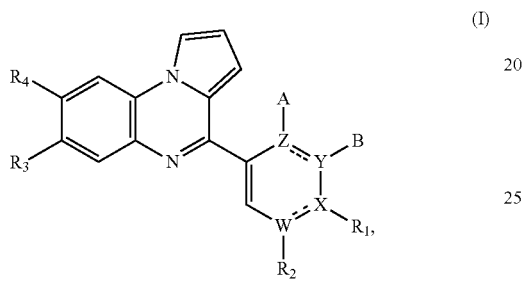

(I)

wherein $R_1$ is hydrogen, hydroxyl, ether, halo-alkyl ether, nitro, amine, alkylamine, dialkylamine, or heterocycle, $R_2$ is hydrogen, nitro, or amine, $R_3$ and R4 are independently selected from hydrogen, halogen, hydroxyl, ether, halo-alkyl ether, alkoxyalkyl, or 2-oxy-2-methylpropanamide, W is C or CH, X is C, CH, or N, Y is C, CH, or N, Z is C or CH, and A and B are H or join to form a carbocyclic ring. It is specifically contemplated that salts, enantiomers, derivatives, metabolites, and prodrugs of these compounds may also be used as RAD51 D-loop formation activity inhibitors in some embodiments of the invention.

In some embodiments, a RAD51 D-loop formation inhibitor is one of the following compounds:

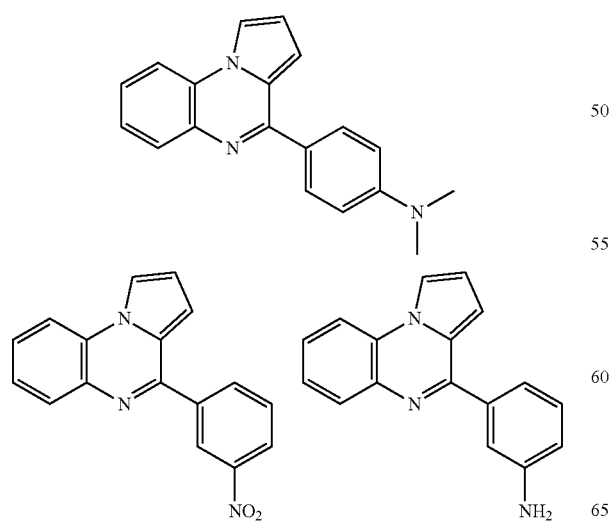

-continued

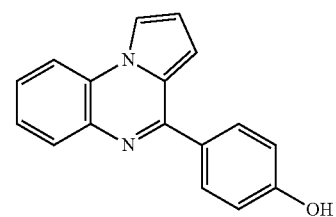

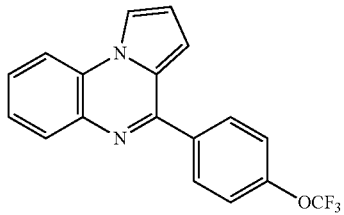

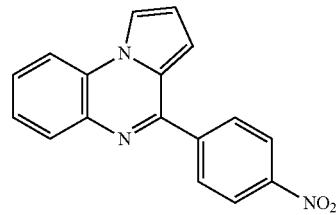

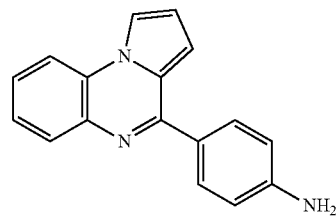

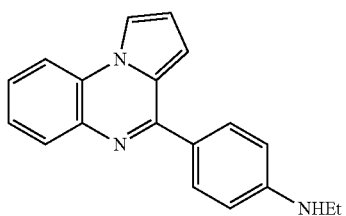

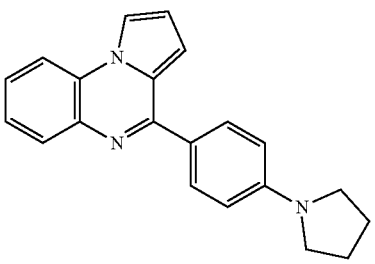

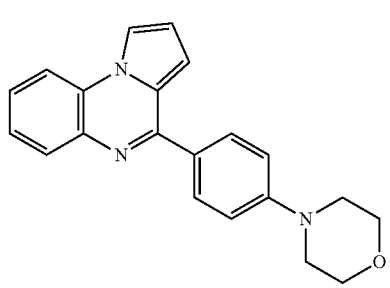

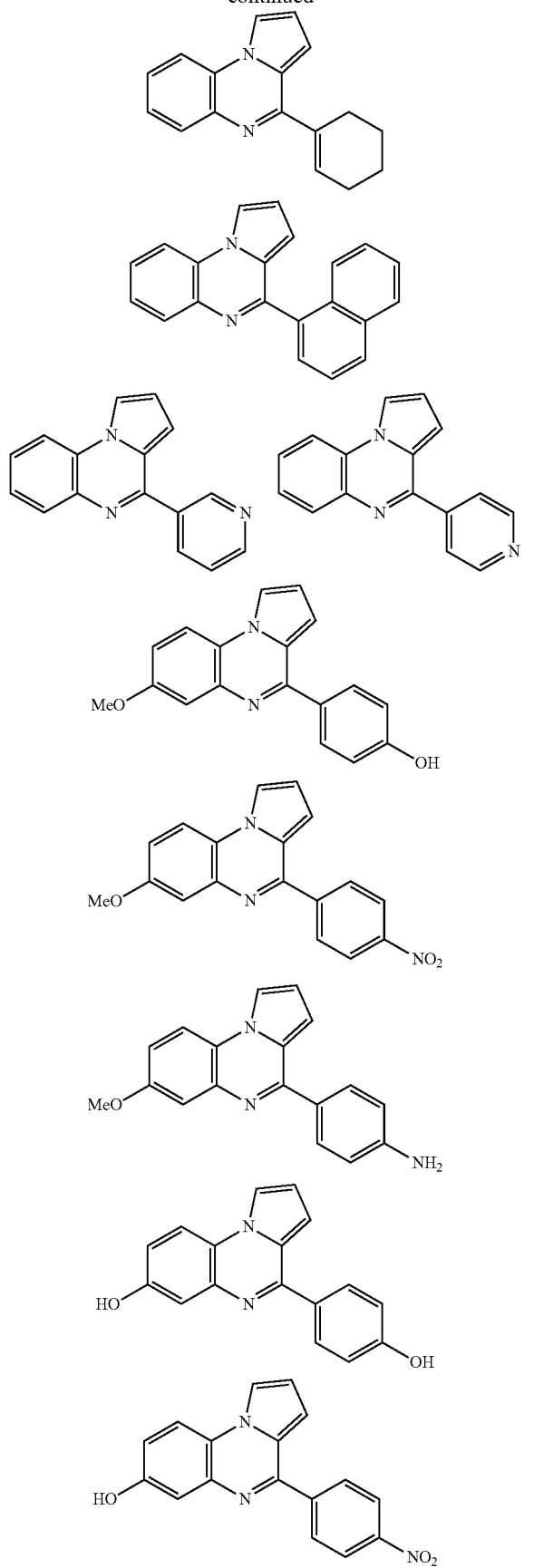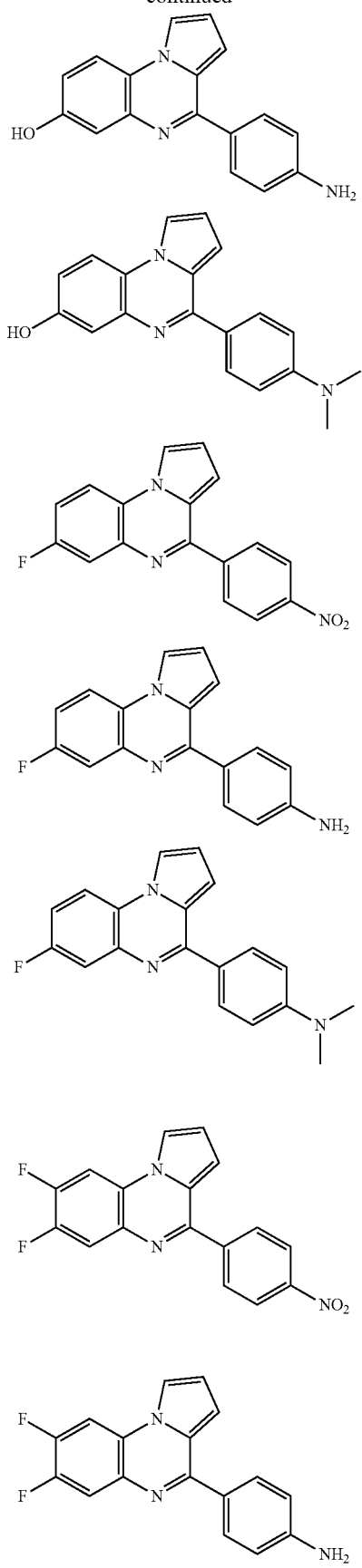

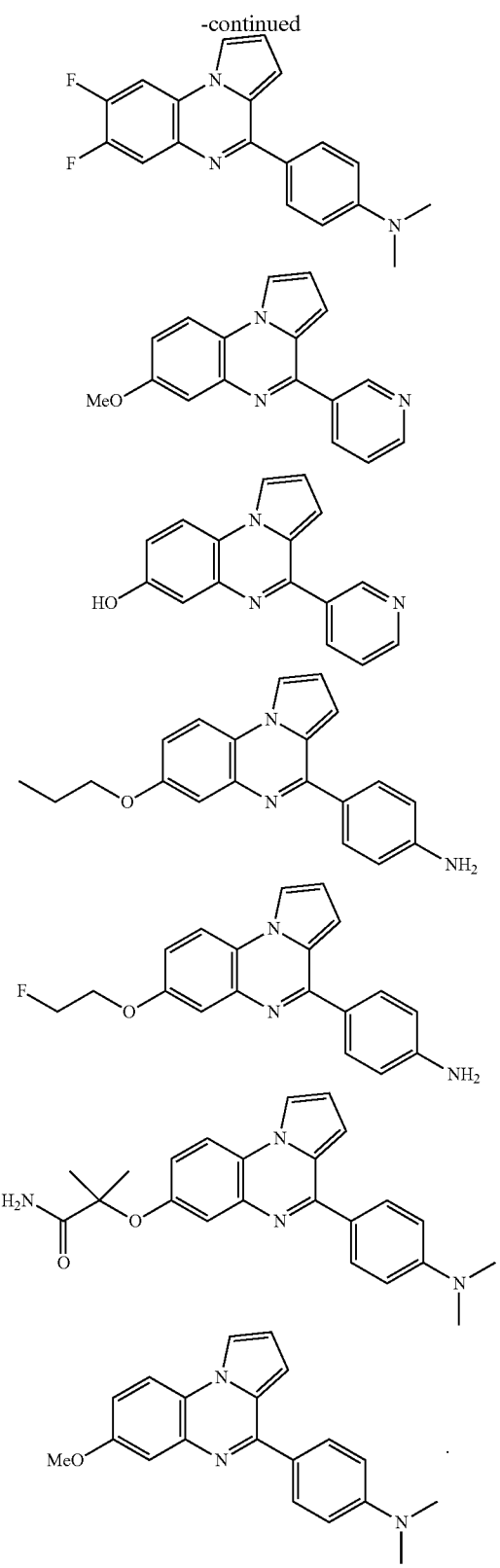

Additional embodiments concern methods for sensitizing cancer cells to a DNA damaging agent comprising administering to a cancer patient an effective amount of a small molecule that directly inhibits RAD51 D-loop formation activity in the cancer cells. In some embodiments, methods for sensitizing cancer cells to a DNA damaging agent comprising administering to a cancer patient an effective amount of a small molecule that selectively inhibits RAD51 D-loop formation activity over RAD51's ability to bind single stranded DNA in the cancer cells.

In certain embodiments, a patient is identified as having cancer or a method includes identifying a patient as having cancer.

An "effective amount" of a compound or composition, generally, is defined as that amount sufficient to detectably and repeatedly achieve the stated desired result, for example, to ameliorate, reduce, minimize or limit the extent of the disease or its symptoms or to increase, stimulate, or promote a desirable physiological response, such as homologous recombination. In some embodiments, the stated result may include elimination, eradication or cure of disease.

It is contemplated that in certain embodiments, a cell is a human cell and the subject or patient is a human patient. In other embodiments, a cell is a mammalian cell and the subject or patient is a mammalian patient. In some embodiments, a cell is a Drosophila cell and the subject or patient is a Drosophila patient. It will be understood that different mammals have their own RAD51 protein that would be a homolog of the human protein. In certain other embodiments, the cell is a eukaryotic cell, while in other embodiments, the cell is a prokaryotic cell and a RAD51 protein homolog or analog is the protein that is modulated. In specific embodiments, a cell may be a sex cell, while in others, the cell is a somatic cell. In particular embodiments, cells used in methods of the invention may be from a cell line. In certain embodiments, the cell is a cell from or in any organism described herein. Moreover, in some embodiments the cell is a cancer cell, while in other embodiments a cell is non-cancerous or normal. In some cases, a cancer cell is resistant to chemotherapy or radiation. Furthermore, it is contemplated that a cell can be in a patient. In some embodiments, the patient has been determined to have chemotherapy- or radiation-resistant cancer. The cancer patient may have cancer of the lung, liver, skin, eye, brain, gum, tongue, hematopoietic system or blood, head, neck, breast, pancreas, prostate, kidney, bone, testicles, ovary, cervix, gastrointestinal tract, lymph system, small intestine, colon, or bladder. Additionally, a cell may be an embryonic stem (ES) cell, such as a murine ES cell, which are used for generating knockout mice. Alternatively, cells may be murine cells that are used for generating a transgenic mouse. Other transgenic animals can be generated using a particular animals cells in the context of methods of the invention.

Methods can be implemented as treatment for patients with cancer. The cancer may be any cancer treatable by administration of a compound described herein. In certain embodiments, a cancer may be treatable using a combination treatment involving a conventional DNA damaging agent with a RAD51 D-loop formation activity inhibitor. In some instances, the RAD51 D-loop formation activity inhibitor may be what allows a cancer to be treated with the DNA damaging agent. Methods can be implemented with any cancer that may be treated with a DNA damaging agent. For example, the cancer may be breast, prostate, ovarian, brain, melanoma, colorectal, liver, lymphoma, lung, oral, head, neck, spleen, lymph node, small intestine, large intestine, blood cells, stomach, pancreatic, endometrium, testicle, skin, esophagus, bone marrow, blood, cervical, bladder, Ewing's sarcoma, thyroid, a glioma, and/or gastrointestinal. Methods and compositions are applicable to other cancers discussed herein, including pre-cancers and tumor cells.

In some embodiments, a cancer patient may have been treated with or will be treated with a DNA damaging agent. In related embodiments, a subject may have been exposed to a DNA damaging agent (as a harmful agent and not as part of a treatment) or be at risk for such exposure. It is contemplated that in some embodiments, the DNA damaging agent is an alkylating agent, nitrosourea, anti-metabolite, plant alkaloid, plant extract, or radioisotope. In specific embodiments, the DNA damaging agent is actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide or etoposide (VP16). In some embodiments, the agent generates interstrand DNA crosslinks (ICL). One example of a DNA damaging agent that generates ICLs is mytomycin C. Any other DNA damaging agent discussed herein may be implemented in methods. In certain embodiments, the DNA damaging agent is radiation.

Methods may involve multiple administrations of one or more compounds, compositions, and/or agents. In certain embodiments, cells or a subject are provided with a RAD51 D-loop formation activity inhibitor and a DNA damaging agent. It is contemplated that compounds, compositions, and/or agents may be formulated in a pharmaceutically acceptable formulation in certain embodiments of the invention.

Moreover, in some methods the order in which things are provided to cells or a subject may vary. In some embodiments, a RAD51 D-loop formation activity inhibitor is provided prior to a DNA damaging agent being provided to a cell or subject. In other embodiments, a RAD51 D-loop formation activity inhibitor is provided simultaneously with a DNA damaging agent or after the DNA damaging agent is provided. It is contemplated that a RAD51 D-loop formation activity inhibitor may be provided to a cell or subject within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 33, 34, 35, 36, 37, 38, 39, 40, 41, 42, 43, 44, 45, 46, 47, 48 hours and/or 1, 2, 3, 4, 5, 6, or 7 days (or any range derivable therein) of the cell or subject being provided with a DNA damaging agent, and vice versa. In certain embodiments, a RAD51 D-loop formation activity inhibitor is provided before, during, and/or after a DNA damaging agent is provided.

In certain embodiments, there are methods for inhibiting RAD51-mediated homologous recombination in a cell comprising providing to the cell an effective amount of a RAD51 modulator, wherein the inhibitor is a small molecule that directly inhibits RAD51 D-loop formation. In some embodiments, there are methods for inhibiting RAD51-mediated homologous recombination while preserving RAD31's ability to form nucleoprotein filaments and RAD51's ability to bind single stranded DNA. In certain aspects, small molecules are presented which selectively inhibit RAD51-mediated homologous recombination over RAD51's ability to form nucleoprotein filaments and RAD51's ability to bind single stranded DNA. In some aspects, a method for inhibiting RAD51-mediated homologous recombination in a cell comprises providing to the cell an effective amount of a RAD51 modulator, wherein the RAD51 modulator is a compound of formula (I):

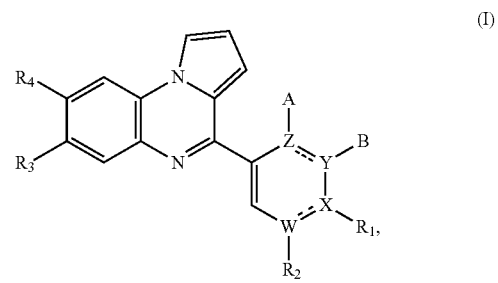

wherein $R_1$ is hydrogen, hydroxyl, ether, halo-alkyl ether, nitro, amine, alkylamine, dialkylamine, or heterocycle, $R_2$ is hydrogen, nitro, or amine, $R_3$ and R4 are independently selected from hydrogen, halogen, hydroxyl, ether, halo-alkyl ether, alkoxyalkyl, or 2-(2-methylpropanamide) ether, W is C or CH, X is C, CH, or N, Y is C, CH, or N, Z is C or CH, and A and B are H or join to form a carbocyclic ring. It is specifically contemplated that salts, enantiomers, derivatives, metabolites, and prodrugs of these compounds may also be used as RAD51-mediated homologous recombination inhibitors in some embodiments of the invention.

In some embodiments, a method for inhibiting RAD51-mediated homologous recombination in a cell comprises providing to the cell an effective amount of at least one of the following RAD51 modulators:

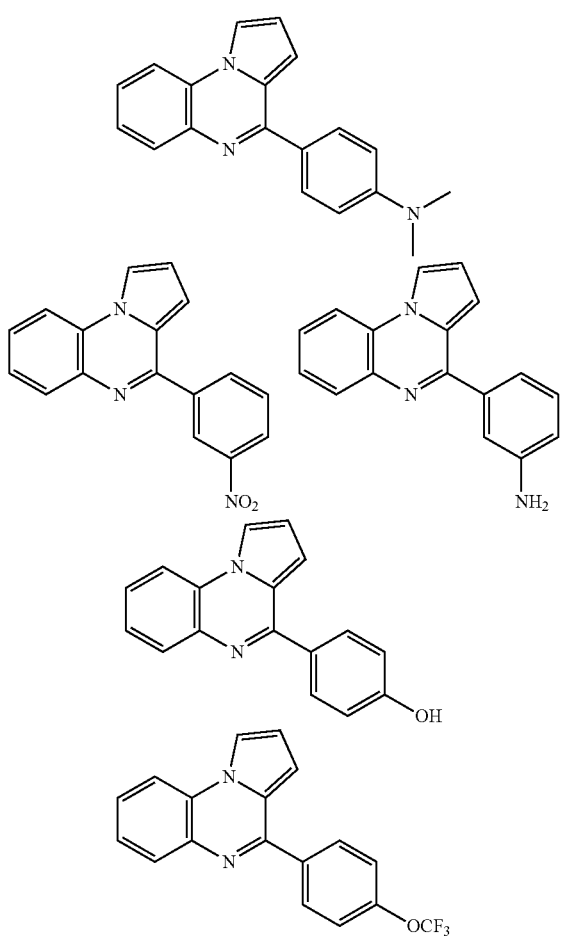

-continued
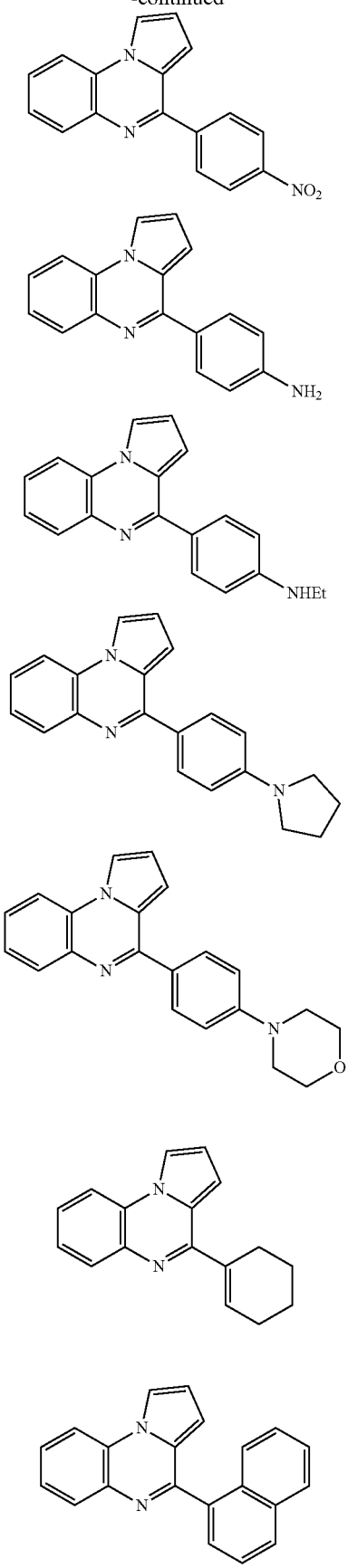
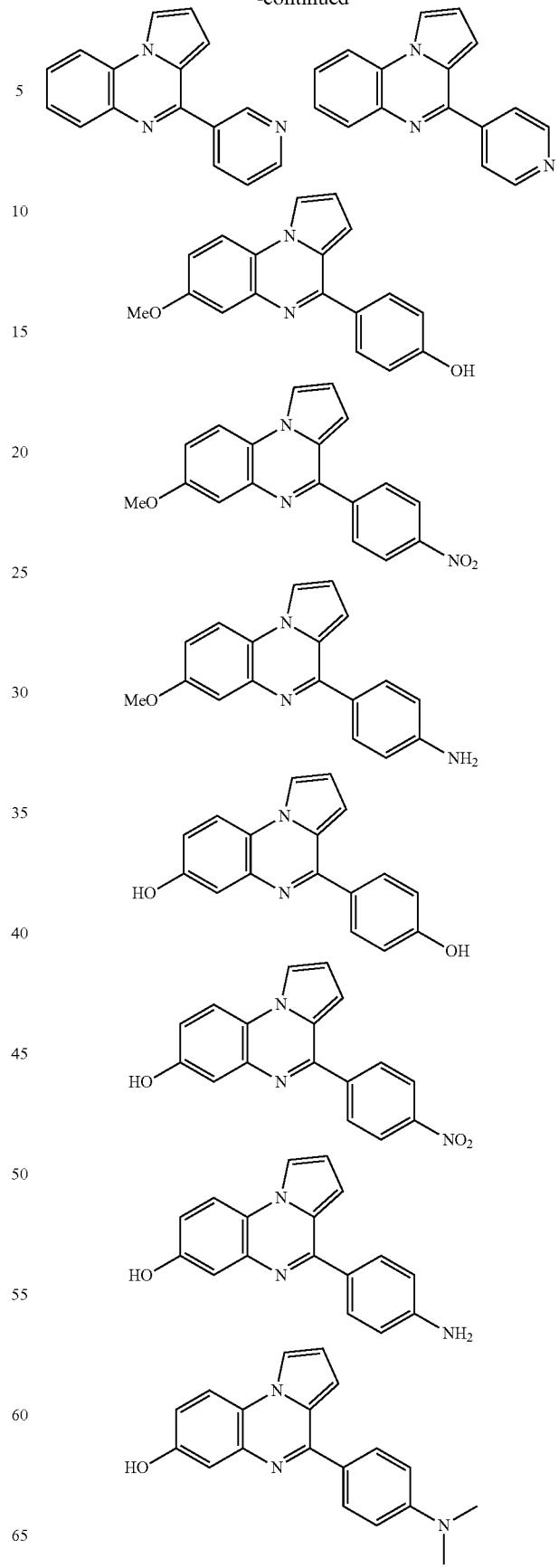

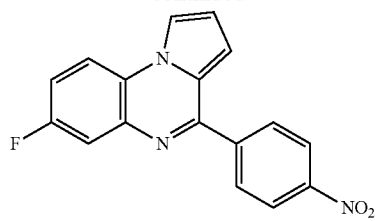
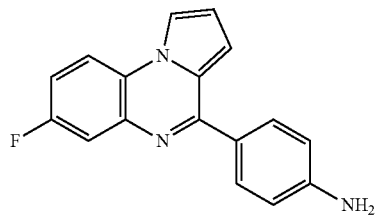
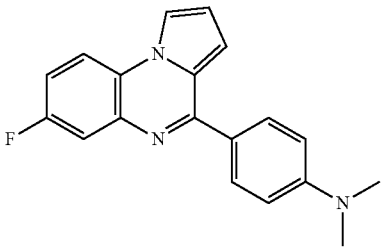
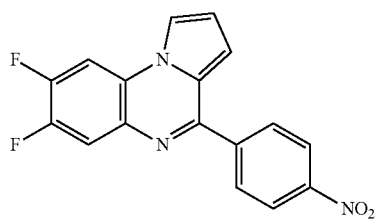
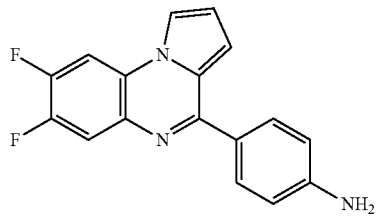
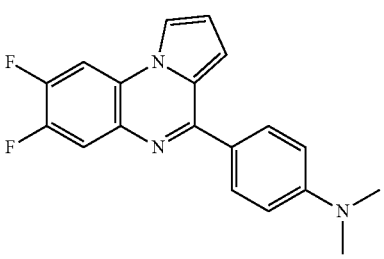
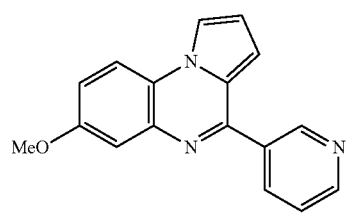

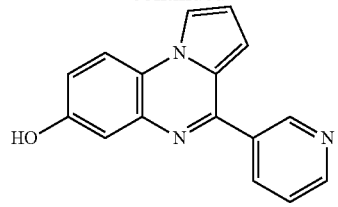
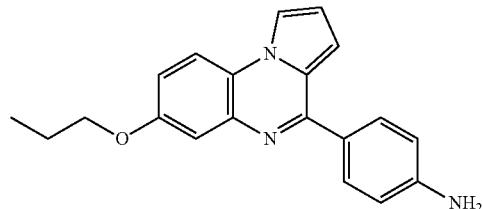
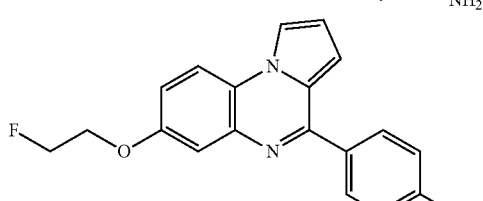
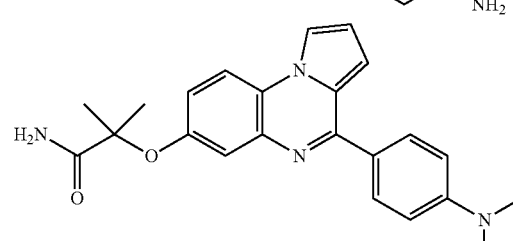
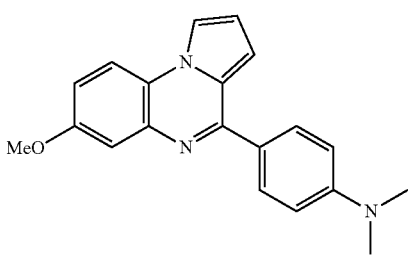

In some aspects, a composition is presented comprising a pharmaceutical formulation a compound of formula (I):

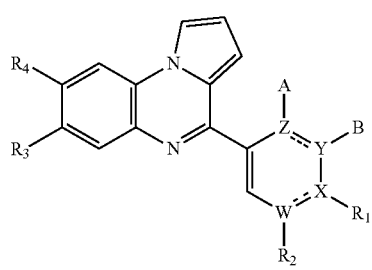

(I)

wherein $R_1$ is hydrogen, hydroxyl, ether, halo-alkyl ether, nitro, amine, alkylamine, dialkylamine, or heterocycle, $R_2$ is hydrogen, nitro, or amine, $R_3$ and $R_4$ are independently selected from hydrogen, halogen, hydroxyl, ether, halo-alkyl ether, alkoxyalkyl, or 2-oxy-2-methylpropanamide, W is C or CH, X is C, CH, or N, Y is C, CH, or N, Z is C or CH, and A and B are H or join to form a carbocyclic ring. It is specifically contemplated that salts, enantiomers, derivatives, metabolites, and prodrugs of these compounds may also be used in some embodiments of the pharmaceutical formulation. It is specifically contemplated that one or more embodiments with respect to the chemical structure of the compound may be excluded as part of the claimed compound.

In some embodiments, a pharmaceutical comprises at least one of the following compounds:

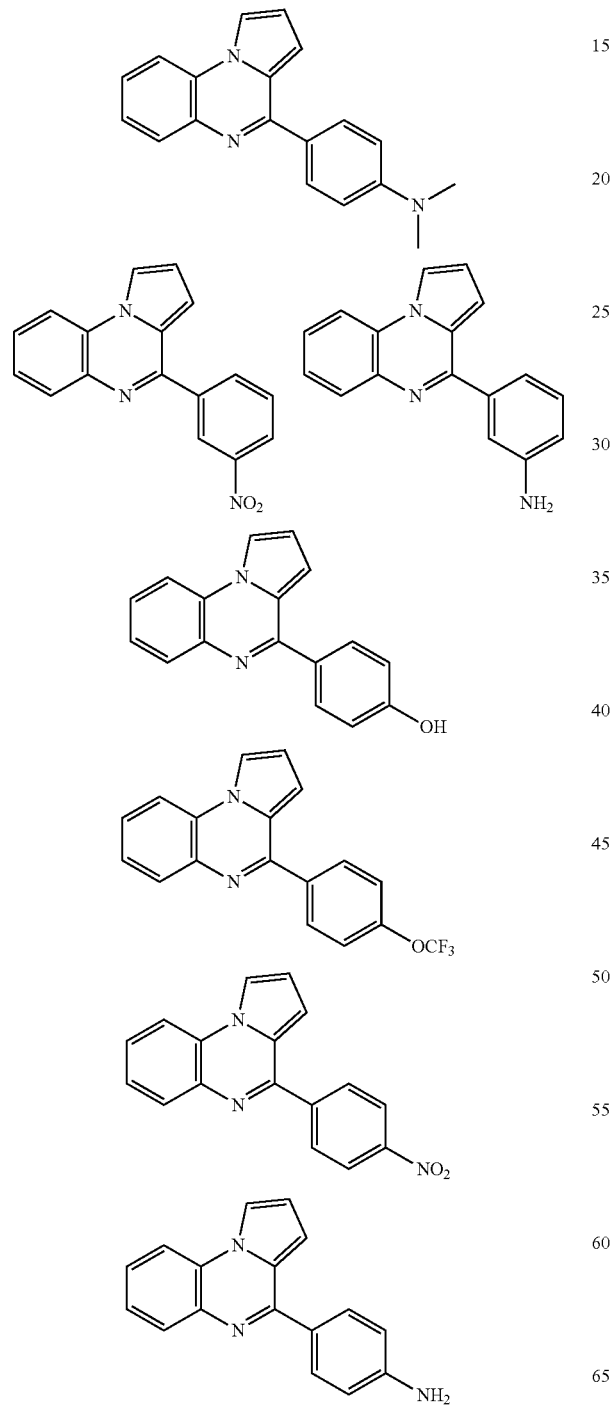

-continued

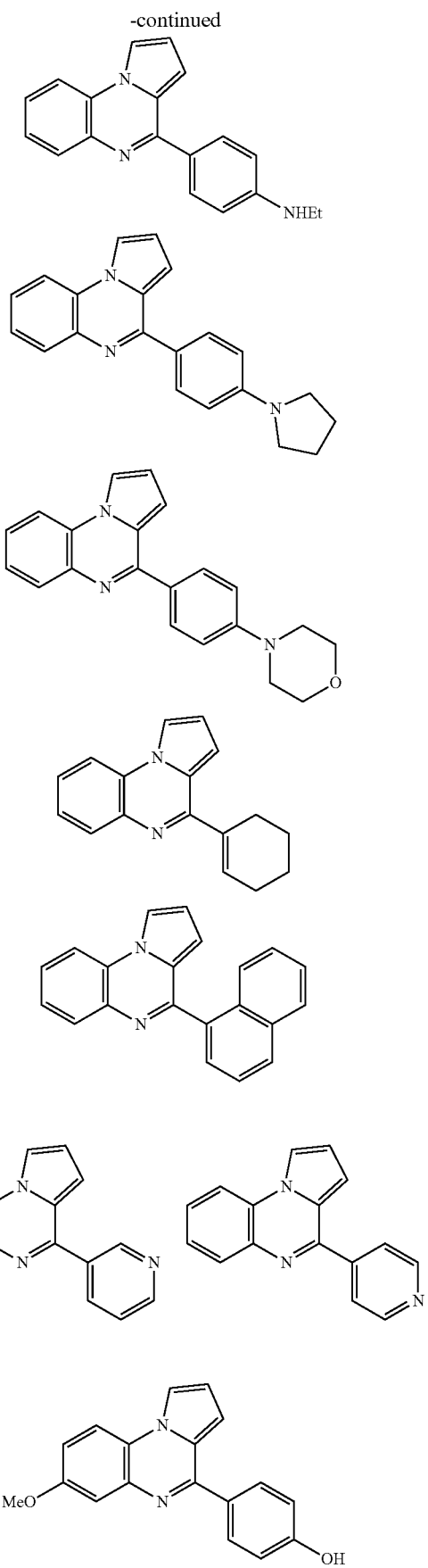

-continued
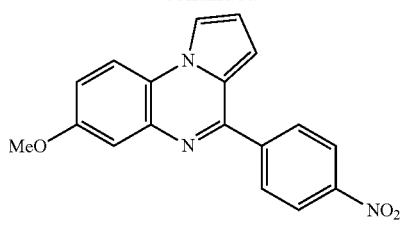
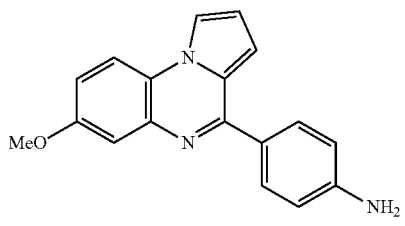
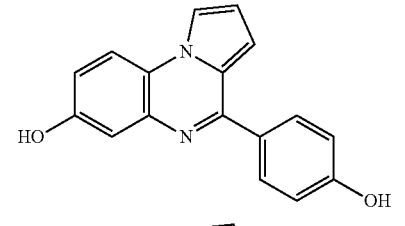
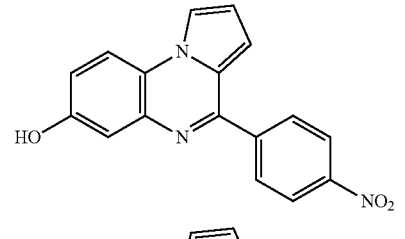
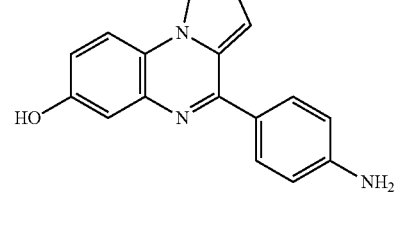
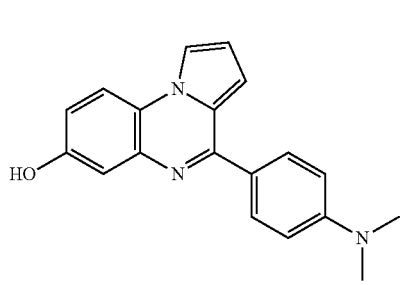
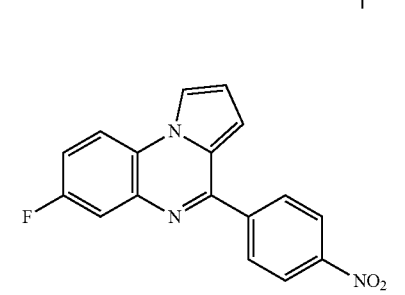
-continued
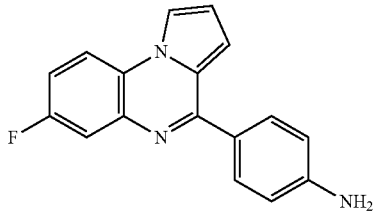
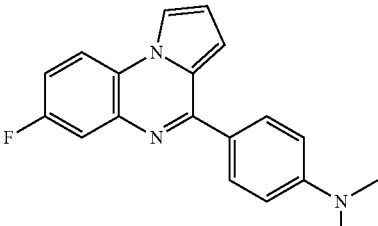
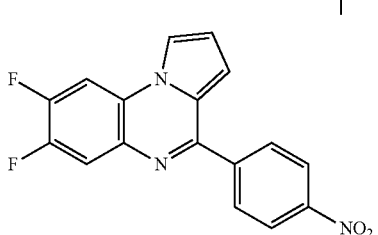
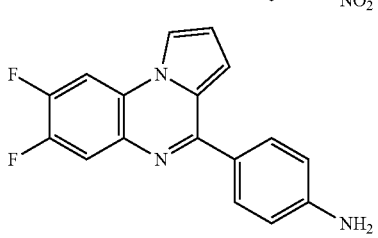
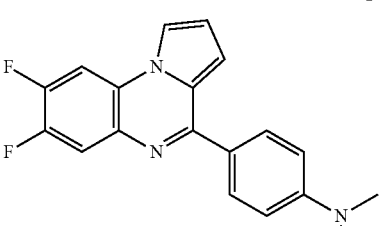
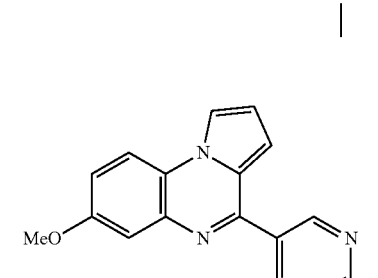
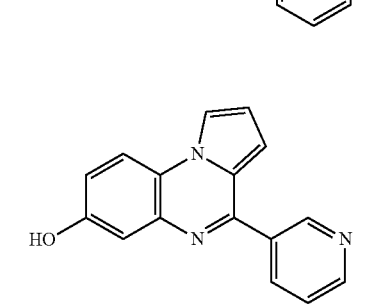

-continued

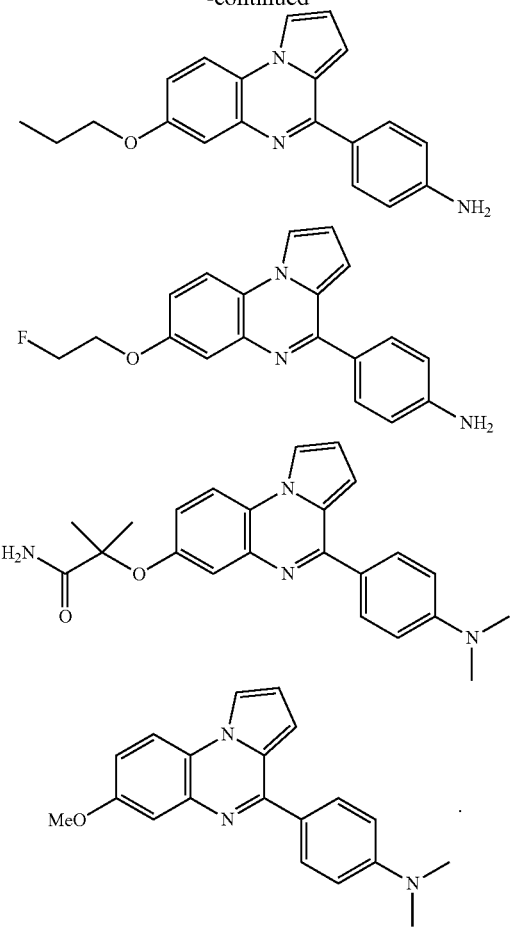

It is specifically contemplated that one or more of the above or described chemical structures may be excluded as an embodiment.

In some embodiments, a composition is presented comprising a pharmaceutical formulation comprising a compound of formula (II):

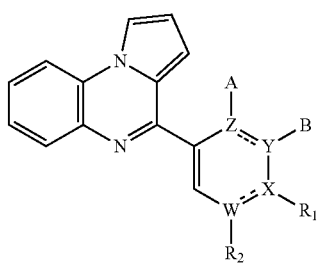

(II)

wherein $R_1$ is hydrogen, hydroxyl, ether, halo-alkyl ether, nitro, amine, alkylamine, dialkylamine, or heterocycle, $R_2$ is hydrogen, nitro, or amine, W is C or CH, X is C, CH, or N, Y is C, CH, or N, Z is C or CH, and A and B are H or join to form a carbocyclic ring. It is specifically contemplated that salts, enantiomers, derivatives, metabolites, and prodrugs of these compounds may also be used in some embodiments of the pharmaceutical formulation. In some embodiments, the pharmaceutical formulation comprises a compound of the following formula:

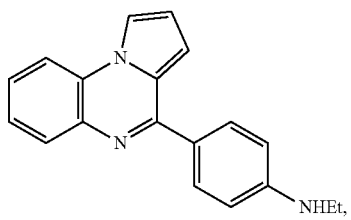

or a salt, enantiomer, derivative, metabolite, or prodrug thereof. It is specifically contemplated that one or more embodiments with respect to the chemical structure of the compound may be excluded as part of the claimed compound.

Some embodiments are directed towards a compound of formula (III):

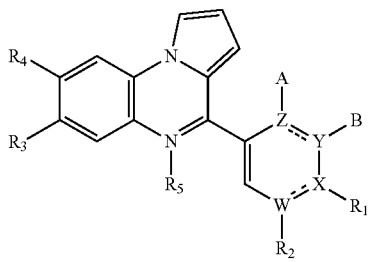

(III)

wherein $R_1$ is hydrogen, hydroxyl, ether, halo-alkyl ether, nitro, amine, alkylamine, dialkylamine, or heterocycle, $R_2$ is hydrogen, nitro, or amine, $R_3$ and R4 are independently selected from hydrogen, halogen, hydroxyl, ether, halo-alkyl ether, alkoxyalkyl, or 2-oxy-2-methylpropanamide, $R_5$ is hydrogen or nothing, W is C or CH, X is C, CH, or N, Y is C, CH, or N, Z is C or CH, and A and B are H or join to form a carbocyclic ring, or a salt, enantiomer, derivative, metabolite, or prodrug thereof. It is specifically contemplated that one or more embodiments with respect to the chemical structure of the compound may be excluded as part of the claimed compound.

In some aspects, the compound of formula (III) is further defined as:

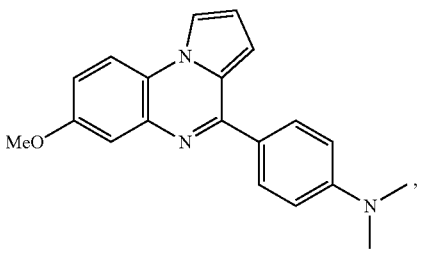 [SMILES: COc1ccc2c(c1)nc(-c1ccc(N(C)C)cc1)c1cccn12]

or a salt, enantiomer, derivative, metabolite, or prodrug thereof. It is specifically contemplated that any composition described herein may contain a combination of compounds described herein. It may contain at least or at most 1, 2, 3, 4, 5, 6 or more such compounds (and any range derivable therein).

In some embodiments, a method of synthesizing a compound of formula (I) is presented,

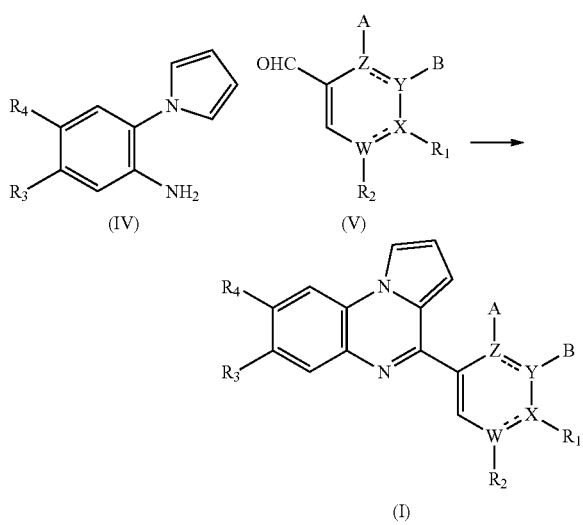

wherein $R_1$ is hydrogen, hydroxyl, ether, halo-alkyl ether, nitro, amine, alkylamine, dialkylamine, or heterocycle, $R_2$ is hydrogen, nitro, or amine, W is C or CH, X is C, CH, or N, Y is C, CH, or N, Z is C or CH, and A and B are H or join to form a carbocyclic ring, and $R_3$ and R4 are independently selected from hydrogen, halogen, hydroxyl, ether, halo-alkyl ether, alkoxyalkyl, or 2-oxy-2-methylpropanamide, comprising reacting a compound of formula (IV) with a compound of formula (V) in the presence of a base and a Lewis acid. In some embodiments, the base is an amine. In certain embodiments, the base is 1,2,3-benzotriazole. In some aspects, the Lewis acid is aluminum trichloride. The method of synthesizing a compound of formula (I) may further comprise the step of reacting a crude reaction mixture of the compound of formula (I) with an oxidant. In some embodiments, the oxidant is manganese dioxide.

Some embodiments are directed towards a method of synthesizing compound 8.

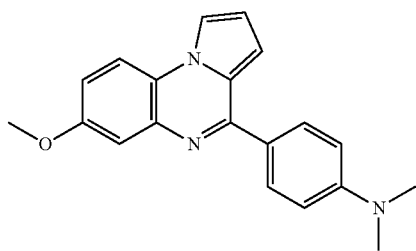

In some aspects, a method of preparing compound 8 comprises the step of reacting 5-methoxy-2-(1H-pyrrol-1-yl)aniline and 4-(dimethylamino)benzaldehyde in the presence of a base and a Lewis acid. In some embodiments, the base is an amine. In certain embodiments, the base is 1,2,3-benzotriazole. In some aspects, the Lewis acid is aluminum trichloride. A method of synthesizing compound 8 may further comprise the step of reacting a crude reaction mixture of 5-methoxy-2-(1H-pyrrol-1-yl)aniline and 4-(dimethylamino) benzaldehyde with an oxidant. In some embodiments, the oxidant is manganese dioxide.

A "disease" is defined as a pathological condition of a body part, an organ, or a system resulting from any cause, such as infection, genetic defect, or environmental stress. A "health-related condition" is defined herein to refer to a condition of a body part, an organ, or a system that may not be pathological, but for which treatment is sought. Examples include conditions for which cosmetic therapy is sought, such as skin wrinkling, skin blemishes, and the like. The disease can be any disease, and non-limiting examples include hyperproliferative diseases such as cancer and pre-malignant lesions, wounds, and infections.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 1. Schematic representation of the mechanism of DNA double strand breaks repair by homologous recombination. Following a DSB, the DNA ends are resected to generate 3' ssDNA overhangs onto which RAD51 loads. The resulting RAD51-ssDNA nucleoprotein filament is capable of invading homologous dsDNA and base-pairing with complementary DNA, thereby forming a heteroduplex and displacing a loop (D-loop) of ssDNA.

FIGS. 2A-C: High-throughput (HT) screen for compounds that inhibit RAD51's D-loop activity: FIG. 2A. One biochemical assay monitors RAD51 binding to fluorescently-labeled ssDNA, which is detected as an increase in fluorescence polarization. FIG. 2B. A second parallel biochemical assay monitors fluorescence intensity, which decreases upon pairing of Black Hole Quencher 1-labeled ssDNA with a fluorescein-labeled complementary double-hairpin duplex. FIG. 2C. Compounds were tested for the ability to influence the efficiency of these two RAD51-mediated processes, and the results of this HT are displayed. Blue symbols=ASDI library compounds, red symbols=LOPAC library compounds.

FIG. 3. Compound 1 inhibits RAD51 HR activity with minimal interference of RAD51-ssDNA binding. FIG. 3A Structure of 1. FIG. 3B 1 inhibits D-loop formation by >70% at concentrations that give less than 50% ssDNA binding inhibition. Solid lines represent local weighted regression with dashed lines representing the 95% confidence intervals. FIG. 3C Gel-based D-loop assay used to generate D-loop formation curve in B showing that 1 inhibits RAD51-mediated assimilation of a radiolabeled ssDNA oligonucleotide into the homologous region of a supercoiled dsDNA plasmid.

FIG. 4. An overview is shown for the optimization strategy of 8.

FIGS. 5A-5C: FIG. 5A Inhibition of cellular HR activity by 1 and optimized analogs of 1 using the DR-GFP assay. Data were collected at 24 hours following transfection with the I-SceI bearing plasmid pCBASce. Error bars denote the standard error. FIG. 5B Inhibition of cellular HR activity by 1 and optimized analog 9h at 24 hours post-transfection. Error bars denote the standard error. FIG. 5C Representative micrographs showing RAD51 foci in green within the nucleus counterstained with DAPI (blue). FIG. 5D RAD51 focus counts per nucleus for at least 100 nuclei at 6 hours post-irradiation.

FIGS. 6A-6F: Clonogenic survival of tumor cell lines treated with veliparib, olaparib, or ionizing radiation followed by outgrowth in the presence of varying amounts of RAD51 D-loop activity inhibitor RI(dl)-2 (compound 9h) or vehicle. RI(dl)-2 (compound 9h) significantly sensitizes cancer cell lines when administered immediately after veliparib, olaparib, or irradiation and allowed to incubate with cells for the duration of clonogenic outgrowth thereafter. FIG. 6A PC-3 cell line treated with veliparib. FIG. 6B Caov-3 cell line treated with veliparib. FIG. 6C Caov-3 cell line treated with olaparib. FIG. 6D SKOV3.ip1 cell line treated with veliparib. FIG. 6E Kuramochi cell line treated with veliparib. FIG. 6F U2OS cell line treated with ionizing radiation (x-rays).

DESCRIPTION OF ILLUSTRATIVE EMBODIMENTS

The present invention overcomes the deficiencies of the prior art by providing compounds that selectively inhibit the D-loop-formation activity of a protein involved in homologous recombinational (HR) DNA repair, RAD51. Inhibiting RAD51-mediated D-loop formation while preserving RAD51's ability to form nucleoprotein filaments may target DNA repair while minimizing replication-associated toxicity in normal tissue. Drugs that selectively inhibit RAD51 D-loop formation activity could potentially be used as decreased-toxicity alternatives to inhibit HR in cancer cells, thereby decreasing side effects associated with broad spectrum RAD51 inhibitors.

A. RAD51 PROTEIN

A common hallmark of tumor cells is the over-expression of the RAD51 recombinase protein. Numerous lines of evidence indicate that tumor cells are especially dependent upon the HR function of RAD51.[11, 12, 28] This well-established feature of cancer cells has made RAD51 an attractive drug target, and several small molecules that inhibit cellular RAD51 function have been described as reviewed by Huang and Mazin.[16] In addition to its classical role in catalyzing homologous strand exchange, RAD51 additionally plays a central role in protecting stalled replication forks from nucleolytic degradation.[21, 22] This protective function in replication requires that RAD51 is able to bind ssDNA, however it may not require the strand invasion activity of RAD51.

B. DEVELOPMENT OF SELECTIVE RAD51 HR INHIBITORS

Presented herein are the results of a drug development campaign to inhibit RAD51's HR activity while sparing its ssDNA binding activity. Compound 1 was identified as a promising lead compound, and subsequent SAR efforts yielded additional compounds with biochemical and cell-based activities.

This series of compounds represents a major step forward in the development of RAD51-targeting small molecules. These are the only known compounds that specifically inhibit RAD51's HR activity without interfering with its ability to bind ssDNA both in vitro and in cells. Halenaquinone was previously reported to strongly inhibit RAD51's HR activity while sparing its ssDNA binding activity in biochemical assays.[20] However, Halenaquinone was shown to inhibit the formation of RAD51 foci in human cells following irradiation, suggesting that in a cellular context this compound may prevent sufficient loading of RAD51 onto damaged DNA at the site of radiation-induced DSBs to form visible foci. Other characterized RAD51 inhibitors including our previously-described inhibitors RI-1 and RI-2 act by preventing RAD51 from loading onto damaged DNA.[13,19]

Compound 1 and the analogs presented herein represent potential cancer therapeutics aimed at sensitizing tumors to DNA-damaging therapies. Considering its high potency for inhibiting both D-loop formation and HR, compound 9h provides an important candidate for further investigation. Meanwhile, since compound 9h has almost no impact on RAD51-ssDNA binding, it also presents a novel tool for basic scientists who wish to study the different functions of RAD51.

C. CANCER AND DNA DAMAGING AGENTS

In certain embodiments, the invention is applicable to the treatment of cancer insofar as such treatments may involve DNA damaging agents.

Cancer cells that may be treated by methods and compositions of the invention also include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The term "DNA damaging agent" refers to any agent that directly or indirectly damages DNA for which homologous recombination could repair the damage. Specific examples of DNA-damaging agents include alkylating agents, nitrosoureas, anti-metabolites, plant alkaloids, plant extracts and radioisotopes. Specific examples of agents also include DNA-damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubicin (Cerubicine), idarubicin (Idamycin) and epirubicin (Ellence), anthracyclin analogs such as mitoxantrone, actinimycin D, non-intercalating topoisomerase inhibitors such as epipodophyllotoxins (etoposide or VP16, teniposide or VM-26), podophylotoxin, bleomycin (Bleo), pepleomycin, compounds that form adducts with nucleic acid including platinum derivatives, e.g., cisplatin (CDDP), trans analog of cisplatin, carboplatin, iproplatin, tetraplatin and oxaliplatin, as well as camptothecin, topotecan, irinotecan (CPT-11), and SN-38. Specific examples of nucleic acid damaging treatments include radiation e.g., ultraviolet (UV), infrared (IR), or α-, β-, or γ-radiation, as well as environmental shock, e.g., hyperthermia. One of skill in the art can identify and use other DNA-damaging agents and treatments.

D. CHEMICAL DEFINITIONS

As used herein, a "small molecule" refers to an organic compound that is either synthesized via conventional organic chemistry methods (e.g., in a laboratory) or found in nature. Typically, a small molecule is characterized in that it contains several carbon-carbon bonds, and has a molecular weight of less than about 1500 grams/mole. In certain embodiments, small molecules are less than about 1000 grams/mole. In certain embodiments, small molecules are less than about 550 grams/mole. In certain embodiments, small molecules are between about 200 and about 550 grams/mole. In certain embodiments, small molecules exclude peptides (e.g., compounds comprising 2 or more amino acids joined by a peptidyl bond). In certain embodiments, small molecules exclude nucleic acids.

As used herein, the term "amino" means $-NH_2$; the term "nitro" means $-NO_2$; the term "halo" or "halogen" designates $-F$, $-Cl$, $-Br$ or $-I$; the term "mercapto" means $-SH$; the term "cyano" means $-CN$; the term "azido" means $-N_3$; the term "silyl" means $-SiH_3$, and the term "hydroxy" means $-OH$. In certain embodiments, a halogen may be $-Br$ or $-I$.

As used herein, a "monovalent anion" refers to anions of a −1 charge. Such anions are well-known to those of skill in the art. Non-limiting examples of monovalent anions include halides (e.g., $F^-$, $Cl^-$, $Br^-$ and $I^-$), $NO_2^-$, $NO_3^-$, hydroxide ($OH^-$) and azide ($N_3^-$).

As used herein, the structure ══ indicates that the bond may be a single bond or a double bond. Those of skill in the chemical arts understand that in certain circumstances, a double bond between two particular atoms is chemically feasible and in certain circumstances, a double bond is not.

The present invention therefore contemplates that a double bond may be formed only when chemically feasible.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$ alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)$ $CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)$ $CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, and —$CH_2Si(CH_3)_3$. The term "haloalkyl" refers to any alkyl group having one or more hydrogen atoms replaced by a halogen atom. —$CF_3$ and —$CH_2CH_2Cl$ are non-limiting examples of haloalkyl groups.

The term "heterocycle" refers to a cyclic functional group that has atoms of at least two different elements as members of its ring(s). Pyrrole, isoxazole, furan, pyridine, thiophene are non-limiting examples of heterocycles.

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted $C_n$-alkenyl, and heteroatom-substituted $C_n$-alkenyl. In certain embodiments, lower alkenyls are contemplated. The term "lower alkenyl" refers to alkenyls of 1-6 carbon atoms (that is, 1, 2, 3, 4, 5 or 6 carbon atoms). The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —$CH=CH_2$ (vinyl), —$CH=CHCH_3$, —$CH=CHCH_2CH_3$, —$CH_2CH=CH_2$ (allyl), —$CH_2CH=CHCH_3$, and —$CH=CH$—$C_6H_5$. The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —$CH=CHF$, —$CH=CHCl$ and —$CH=CHBr$, are non-limiting examples of heteroatom-substituted alkenyl groups.

The term "aryl" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C≡CH$, —$C_6H_4C≡CCH_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, quinolyl, indolyl, and imidazoyl. In certain embodiments, heteroatom-substituted aryl groups are contemplated. In certain embodiments, heteroatom-unsubstituted aryl groups are contemplate. In certain embodiments, an aryl group may be mono-, di-, tri-, tetra- or penta-substituted with one or more heteroatom-containing substitutents.

The term "aralkyl" includes heteroatom-unsubstituted aralkyl, heteroatom-substituted aralkyl, heteroatom-unsubstituted $C_n$-aralkyl, heteroatom-substituted $C_n$-aralkyl, heteroaralkyl, and heterocyclic aralkyl groups. In certain embodiments, lower aralkyls are contemplated. The term "lower aralkyl" refers to aralkyls of 7-12 carbon atoms (that is, 7, 8, 9, 10, 11 or 12 carbon atoms). The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. Non-limiting examples of heteroatom-unsubstituted aralkyls are: phenyl-methyl (benzyl, Bn) and phenylethyl. The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "acyl" includes straight-chain acyl, branched-chain acyl, cycloacyl, cyclic acyl, heteroatom-unsubstituted acyl, heteroatom-substituted acyl, heteroatom-unsubstituted $C_n$-acyl, heteroatom-substituted $C_n$-acyl, alkylcarbonyl, alkoxycarbonyl and aminocarbonyl groups. In certain embodiments, lower acyls are contemplated. The term "lower acyl" refers to acyls of 1-6 carbon atoms (that is, 1, 2, 3, 4, 5 or 6 carbon atoms). The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —CHO, —C(O)CH$_3$, —C(O)CH$_2$CH$_3$, C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, and —COC$_6$H$_3$(CH$_3$)$_2$, are non-limiting examples of heteroatom-unsubstituted acyl groups. The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The groups, —C(O)CH$_2$CF$_3$, —CO$_2$H, —CO$_2^-$, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, and —CONHCH$_2$CF$_3$, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted $C_n$-alkoxy, and heteroatom-substituted $C_n$-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted $C_n$-alkenyloxy, and heteroatom-substituted $C_n$-alkenyloxy. The term "heteroatom-unsubstituted $C_n$-alkenyloxy" refers to a group, having the structure —OR, in which R is a heteroatom-unsubstituted $C_n$-alkenyl, as that term is defined above. The term "heteroatom-substituted $C_n$-alkenyloxy" refers to a group, having the structure —OR, in which R is a heteroatom-substituted $C_n$-alkenyl, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted $C_n$-alkynyloxy, and heteroatom-substituted $C_n$-alkynyloxy. The term "heteroatom-unsubstituted $C_n$-alkynyloxy" refers to a group, having the structure —OR, in which R is a heteroatom-unsubstituted $C_n$-alkynyl, as that term is defined above. The term "heteroatom-substituted $C_n$-alkynyloxy" refers to a group, having the structure —OR, in which R is a heteroatom-substituted $C_n$-alkynyl, as that term is defined above.

The term "aryloxy" includes heteroatom-unsubstituted aryloxy, heteroatom-substituted aryloxy, heteroatom-unsubstituted $C_n$-aryloxy, heteroatom-substituted $C_n$-aryloxy, heteroaryloxy, and heterocyclic aryloxy groups. The term "heteroatom-unsubstituted $C_n$-aryloxy" refers to a group, having the structure —OAr, in which Ar is a heteroatom-unsubstituted $C_n$-aryl, as that term is defined above. A non-limiting example of a heteroatom-unsubstituted aryloxy group is —OC$_6$H$_5$. The term "heteroatom-substituted $C_n$-aryloxy" refers to a group, having the structure —OAr, in which Ar is a heteroatom-substituted $C_n$-aryl, as that term is defined above.

The term "aralkyloxy" includes heteroatom-unsubstituted aralkyloxy, heteroatom-substituted aralkyloxy, heteroatom-unsubstituted $C_n$-aralkyloxy, heteroatom-substituted $C_n$-aralkyloxy, heteroaralkyloxy, and heterocyclic aralkyloxy groups. The term "heteroatom-unsubstituted $C_n$-aralkyloxy" refers to a group, having the structure —OAr, in which Ar is a heteroatom-unsubstituted $C_n$-aralkyl, as that term is defined above. The term "heteroatom-substituted $C_n$-aralkyloxy" refers to a group, having the structure —OAr, in which Ar is a heteroatom-substituted $C_n$-aralkyl, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups. The term "heteroatom-unsubstituted $C_n$-acyloxy" refers to a group, having the structure —OAc, in which Ac is a heteroatom-unsubstituted $C_n$-acyl, as that term is defined above. For example, —OC(O)CH$_3$ is a non-limiting example of a heteroatom-unsubstituted acyloxy group. The term "heteroatom-substituted $C_n$-acyloxy" refers to a group, having the structure —OAc, in which Ac is a heteroatom-substituted $C_n$-acyl, as that term is defined above. For example, —OC(O)OCH$_3$ and —OC(O)NHCH$_3$ are non-limiting examples of heteroatom-unsubstituted acyloxy groups.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted $C_n$-alkylamino, and heteroatom-substituted $C_n$-alkylamino. The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —$NHCH_3$, —$NHCH_2CH_3$, —$NHCH_2CH_2CH_3$, —$NHCH(CH_3)_2$, —$NHCH(CH_2)_2$, —$NHCH_2CH_2CH_2CH_3$, —$NHCH(CH_3)CH_2CH_3$, —$NHCH_2CH(CH_3)_2$, —$NHC(CH_3)_3$, —$N(CH_3)_2$, —$N(CH_3)CH_2CH_3$, —$N(CH_2CH_3)_2$, N-pyrrolidinyl, and N-piperidinyl. The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "alkenylamino" includes straight-chain alkenylamino, branched-chain alkenylamino, cycloalkenylamino, cyclic alkenylamino, heteroatom-unsubstituted alkenylamino, heteroatom-substituted alkenylamino, heteroatom-unsubstituted $C_n$-alkenylamino, heteroatom-substituted $C_n$-alkenylamino, dialkenylamino, and alkyl(alkenyl)amino groups. The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "alkynylamino" includes straight-chain alkynylamino, branched-chain alkynylamino, cycloalkynylamino, cyclic alkynylamino, heteroatom-unsubstituted alkynylamino, heteroatom-substituted alkynylamino, heteroatom-unsubstituted $C_n$-alkynylamino, heteroatom-substituted $C_n$-alkynylamino, dialkynylamino, alkyl(alkynyl)amino, and alkenyl(alkynyl)amino groups. The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "arylamino" includes heteroatom-unsubstituted arylamino, heteroatom-substituted arylamino, heteroatom-unsubstituted $C_n$-arylamino, heteroatom-substituted $C_n$-arylamino, heteroarylamino, heterocyclic arylamino, and alkyl(aryl)amino groups. The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above.

The term "aralkylamino" includes heteroatom-unsubstituted aralkylamino, heteroatom-substituted aralkylamino, heteroatom-unsubstituted $C_n$-aralkylamino, heteroatom-substituted $C_n$-aralkylamino, heteroaralkylamino, heterocyclic aralkylamino groups, and diaralkylamino groups. The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above.

The term "amido" includes straight-chain amido, branched-chain amido, cycloamido, cyclic amido, heteroatom-unsubstituted amido, heteroatom-substituted amido, heteroatom-unsubstituted $C_n$-amido, heteroatom-substituted $C_n$-amido, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The group, —NHC(O)CH$_3$, is a non-limiting example of a heteroatom-unsubstituted amido group. The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is a non-limiting example of a heteroatom-substituted amido group.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. The term "heteroatom-unsubstituted $C_n$-alkylthio" refers to a group, having the structure —SR, in which R is a heteroatom-unsubstituted $C_n$-alkyl, as that term is defined above. The group, —SCH$_3$, is an example of a heteroatom-unsubstituted alkylthio group. The term "heteroatom-substituted $C_n$-alkylthio" refers to a group, having the structure —SR, in which R is a heteroatom-substituted $C_n$-alkyl, as that term is defined above.

The term "alkenylthio" includes straight-chain alkenylthio, branched-chain alkenylthio, cycloalkenylthio, cyclic alkenylthio, heteroatom-unsubstituted alkenylthio, heteroatom-substituted alkenylthio, heteroatom-unsubstituted $C_n$-alkenylthio, and heteroatom-substituted $C_n$-alkenylthio. The term "heteroatom-unsubstituted $C_n$-alkenylthio" refers to a group, having the structure —SR, in which R is a heteroatom-unsubstituted $C_n$-alkenyl, as that term is defined above. The term "heteroatom-substituted $C_n$-alkenylthio" refers to a group, having the structure —SR, in which R is a heteroatom-substituted $C_n$-alkenyl, as that term is defined above.

The term "alkynylthio" includes straight-chain alkynylthio, branched-chain alkynylthio, cycloalkynylthio, cyclic alkynylthio, heteroatom-unsubstituted alkynylthio, heteroatom-substituted alkynylthio, heteroatom-unsubstituted $C_n$-alkynylthio, and heteroatom-substituted $C_n$-alkynylthio. The term "heteroatom-unsubstituted $C_n$-alkynylthio" refers to a group, having the structure —SR, in which R is a heteroatom-unsubstituted $C_n$-alkynyl, as that term is defined above. The term "heteroatom-substituted $C_n$-alkynylthio" refers to a group, having the structure —SR, in which R is a heteroatom-substituted $C_n$-alkynyl, as that term is defined above.

The term "arylthio" includes heteroatom-unsubstituted arylthio, heteroatom-substituted arylthio, heteroatom-unsubstituted $C_n$-arylthio, heteroatom-substituted $C_n$-arylthio, heteroarylthio, and heterocyclic arylthio groups. The term "heteroatom-unsubstituted $C_n$-arylthio" refers to a group, having the structure —SAr, in which Ar is a heteroatom-unsubstituted $C_n$-aryl, as that term is defined above. The group, —SC$_6$H$_5$, is an example of a heteroatom-unsubstituted arylthio group. The term "heteroatom-substituted $C_n$-arylthio" refers to a group, having the structure —SAr, in which Ar is a heteroatom-substituted $C_n$-aryl, as that term is defined above.

The term "aralkylthio" includes heteroatom-unsubstituted aralkylthio, heteroatom-substituted aralkylthio, heteroatom-unsubstituted $C_n$-aralkylthio, heteroatom-substituted $C_n$-aralkylthio, heteroaralkylthio, and heterocyclic aralkylthio groups. The term "heteroatom-unsubstituted $C_n$-aralkylthio" refers to a group, having the structure —SAr, in which Ar is a heteroatom-unsubstituted $C_n$-aralkyl, as that term is defined above. The group, —SCH$_2$C$_6$H$_5$, is an example of a heteroatom-unsubstituted aralkyl group. The term "heteroatom-substituted $C_n$-aralkylthio" refers to a group, having the structure —SAr, in which Ar is a heteroatom-substituted $C_n$-aralkyl, as that term is defined above.

The term "acylthio" includes straight-chain acylthio, branched-chain acylthio, cycloacylthio, cyclic acylthio, heteroatom-unsubstituted acylthio, heteroatom-substituted acylthio, heteroatom-unsubstituted $C_n$-acylthio, heteroatom-substituted $C_n$-acylthio, alkylcarbonyloxy, arylcarbonyloxy, alkoxycarbonyloxy, aryloxycarbonyloxy, and carboxylate groups. The term "heteroatom-unsubstituted $C_n$-acylthio" refers to a group, having the structure —SAc, in which Ac is a heteroatom-unsubstituted $C_n$-acyl, as that term is defined above. The group, —SCOCH$_3$, is an example of a heteroatom-unsubstituted acylthio group. The term "heteroatom-substituted C$_n$-acylthio" refers to a group, having the structure —SAc, in which Ac is a heteroatom-substituted C$_n$-acyl, as that term is defined above.

The term "alkylsilyl" includes straight-chain alkylsilyl, branched-chain alkylsilyl, cycloalkylsilyl, cyclic alkylsilyl, heteroatom-unsubstituted alkylsilyl, heteroatom-substituted alkylsilyl, heteroatom-unsubstituted C$_n$-alkylsilyl, and heteroatom-substituted C$_n$-alkylsilyl. The term "heteroatom-unsubstituted C$_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted C$_1$-C$_{10}$-alkylsilyl has 1 to 10 carbon atoms. An alkylsilyl group includes dialkylamino groups. The groups, —Si(CH$_3$)$_3$ and —Si(CH$_3$)$_2$C(CH$_3$)$_3$, are non-limiting examples of heteroatom-unsubstituted alkylsilyl groups. The term "heteroatom-substituted C$_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted C$_1$-C$_{10}$-alkylsilyl has 1 to 10 carbon atoms.

Any apparently unfulfilled valency is to be understood to be properly filled by hydrogen atom(s). For example, a compound with a substituent of —O or —N is to be understood to be —OH or —NH$_2$, respectively.

Any genus, subgenus, or specific compound discussed herein is specifically contemplated as being excluded from any embodiment described herein.

Compounds described herein may be prepared synthetically using conventional organic chemistry methods known to those of skill in the art and/or are commercially available (e.g., ChemBridge Co., San Diego, Calif.).

The claimed invention is also intended to encompass salts of any of the compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps during synthesis. Salts include, but are not limited to, sodium, lithium, potassium, amines, tartrates, citrates, hydrohalides, phosphates and the like. A salt may be a pharmaceutically acceptable salt, for example. Thus, pharmaceutically acceptable salts of compounds of the present invention are contemplated.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

Derivatives of compounds of the present invention are also contemplated. In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S- or the R-configuration, as defined by the IUPAC 1974 Recommendations. Compounds may be of the D- or L-form, for example. It is well known in the art how to prepare and isolate such optically active forms. For example, mixtures of stereoisomers may be separated by standard techniques including, but not limited to, resolution of racemic form, normal, reverse-phase, and chiral chromatography, preferential salt formation, recrystallization, and the like, or by chiral synthesis either from chiral starting materials or by deliberate synthesis of target chiral centers.

In addition, atoms making up the compounds of the present invention are intended to include all isotopic forms of such atoms. Isotopes, as used herein, include those atoms having the same atomic number but different mass numbers.

By way of general example and without limitation, isotopes of hydrogen include tritium and deuterium, and isotopes of carbon include $^{13}$C and $^{14}$C.

As noted above, compounds of the present invention may exist in prodrug form. As used herein, "prodrug" is intended to include any covalently bonded carriers which release the active parent drug or compounds that are metabolized in vivo to an active drug or other compounds employed in the methods of the invention in vivo when such prodrug is administered to a subject. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a subject, cleaves to form a free hydroxyl, free amino, or carboxylic acid, respectively. Other examples include, but are not limited to, acetate, formate, and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (2002), which is incorporated herein by reference.

E. PHARMACEUTICAL FORMULATIONS AND ADMINISTRATION THEREOF

1. Pharmaceutical Formulations and Routes of Administration

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Compounds may comprise different types of carriers depending on whether it is to be administered in solid, liquid or aerosol form, and whether it need to be sterile for such routes of administration as injection. Compounds or compositions can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, systemically, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990).

The actual dosage amount of a composition or compound that is administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a composition. In other embodiments, the compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

In other embodiments, one may use eye drops, nasal solutions or sprays, aerosols or inhalants. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof a lubricant, such as, for example, magnesium stearate; a sweetening agent, such as, for example, sucrose, lactose, saccharin or combinations thereof a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

2. Combination Therapy

In some embodiments, it is contemplated that the RAD51 modulators may be used in conjunction with DNA damaging agents as part of a treatment regimen. This process may involve contacting the cell(s) with the agents at the same time or within a period of time wherein separate administration of the agents produces a desired therapeutic benefit. This may be achieved by contacting the cell, tissue or organism with a single composition or pharmacological formulation that includes two or more agents, or by contacting the cell with two or more distinct compositions or formulations, wherein one composition includes one agent and the other includes another.

Compounds discussed herein may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more DNA damaging agents may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering the RAD51 modulator.

Various combination regimens of the agents may be employed. Non-limiting examples of such combinations are shown below, wherein a compound of the present invention is "A" and a second agent, such as a DNA damaging agent, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

In some embodiments, more than one course of therapy may be employed. It is contemplated that multiple courses may be implemented. In certain embodiments, a patient may have previously undergone radiation or chemotherapy for a cancer that turns out to be chemotherapy- or radiation-resistant. Alternatively, a patient may have a recurring cancer that is to be treated with a DNA damaging agent.

F. ORGANISMS AND CELL SOURCE

Cells that may be used in some methods can be from a variety of sources. Embodiments include the use of mammalian cells, such as cells from monkeys, chimpanzees, rabbits, mice, rats, ferrets, dogs, pigs, humans, and cows. Alternatively, the cells may be from fruit flies, yeast, or *E. coli*, which are all model systems for evaluating homologous recombination.

Methods can involve cells, tissues, or organs involving the heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord.

Moreover, methods can be employed in cells of the following type: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

Moreover, methods can be implemented with or in plants or parts of plants, including fruit, flowers, leaves, stems, seeds, cuttings. Plants can be agricultural, medicinal, or decorative.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Screen for RAD51 D-Loop Inhibitors

Two parallel HT screens to identify small molecules that inhibit RAD51 D-loop activity without affecting its ssDNA binding activity. A previously-described fluorescence polarization-based microplate assay was used to assess the compounds' effects on RAD51-ssDNA binding[23] (FIG. 2a). In order to enable a screen for D-loop specific RAD51 inhibitors, a microplate-based assay that can accurately quantify D-loop formation in a high-throughput fashion [24] (FIG. 2b) was previously developed. This method makes use of two substrates: a closed linear double-hairpin dsDNA, and an ssDNA fused with a black hole quencher. The sequence homology of the two substrates enables RAD51 to catalyze the formation of D-loops, which is quantified as a function of quenched fluorescence. Among the screening compounds tested, those that prevented RAD51 D-loop formation while exerting little effect on RAD51-ssDNA binding (FIG. 2c) were of primary focus. Potential hits were confirmed using secondary low-throughput re-testing, which involved a gel-based D-loop assay to exclude the possibility that the observed inhibition of D-loop activity was due to artefactual interference by compound auto-fluorescence or fluorescence quenching.

Example 2

Cells, Media, and Plasmids

The 293-DR-GFP reporter cell line and pCBASce plasmid were described previously.[27] Cell cultures were maintained in complete DMEM (DMEM+4.5 g/L D-glucose+L-glutamine+10% fetal calf serum+penicillin/streptomycin).

Example 3

Screening Libraries

High-throughput screening of the ASDI Diversity library of 6800 compounds and the Library of Pharmacologically Active Compounds (LOPAC1280) was conducted. From each of the library master plates, 2.5 nmol of compound was acoustically transferred to individual assay plates at Nextval, Inc. This gave a final concentration of 50 µM for each library compound in 50 µl per well of final reaction volume for both the RAD51-DNA binding and RAD51-mediated strand pairing assays.

Example 4

DNA Binding Assay

The fluorescence polarization-based DNA binding assay and purification of human RAD51 used for this assay was performed as previously described with a few modifications.[23] Reactions were carried out in black 384-well polystyrene plates. In each well, RAD51 protein was combined with reaction buffer and varying concentrations of compound in DMSO in an initial volume of 40 µl and incubated at 37° C. for 40 minutes. Then, 10 µl of reaction buffer containing fluorescently-labeled ssDNA substrate (5'-Alexa488-oligo-dT$_{45}$) was added and the reaction incubated at 37° C. for another 40 minutes, after which the plate was read on a Tecan Infinite 200 Pro plate reader equipped with two sets of 485±25 nm/535±35 nm with parallel or perpendicularly-oriented polarization filters. In both steps of the reaction setup, buffer components were maintained at 20 mM HEPES-NaOH (pH 7.5), 2 mM ATP, 10 mM MgCl$_2$, 0.1 mM TCEP-HCl (tris(2-carboxyethyl)phosphine), and 0.25 µM BSA. The final reaction contained 4% DMSO, 0.2 µM RAD51, 30 mM NaCl, 2% glycerol, and 2.22 nM ssDNA substrate. Compound IC$_{50}$ values were obtained by least-squares regression fitting of appropriate linear, log, or sigmoid dose-response models to the data, with the standard error indicated.

Example 5

Solution Assay for RAD51-Mediated Strand Pairing

The FRET-based solution assay for RAD51-mediated strand pairing was performed as described previously.[24] Reactions were performed in black 384-well polystyrene plates. RAD51 in reaction buffer and compound in DMSO were combined in 20 µl and incubated at room temperature for 40 minutes. Then, 10 µl of solution containing the Black Hole Quencher (BHQ1)-tagged ssDNA substrate and CaCl$_2$ was added to each well and the reaction was incubated at 37° C. for 5 minutes to allow RAD51-ssDNA filaments to form. Finally, 20 µl of solution was added containing the Alexa488-tagged dsDNA double hairpin substrate with homology to the ssDNA substrate and the plate was incubated at 37° C. for 50 minutes to allow RAD51-mediated strand invasion, which is measured as a decrease in fluorescence intensity as the BHQ1-tagged ssDNA is paired with the Alexa488-tagged dsDNA. The final reaction contained 25 mM HEPES-NaOH (pH 7.5), 3 mM ATP, 1 mM TCEP-HCl, 1.5 µM BSA, 4% DMSO, 0.1 µM RAD51, 2 mM NaCl, 0.1% glycerol, 10 nM ssDNA, and 5 nM dsDNA. The concentration of CaCl$_2$ was maintained at 5 mM throughout all three steps of the reaction setup. Fluorescence measurements were taken on a Tecan Infinite 200 Pro plate reader equipped with 485±20 nm/535±35 nm filters.

Example 6

Gel-Based D-Loop Assay

Human RAD51 in reaction buffer was combined with compound in 8 µl DMSO, incubated at 37° C. for 10 min, and then 1 µl of 5'-$^{32}$P-labeled 90-mer ssDNA (5'-TACGAATGCACACGGTGTGGTGGGCCCAGGTAT-TGTTAGCGGTTTGAAGCAGGC-GGCAGAAGAAGTAACAAAGGAACCTAGAGGC-CTTTT) with homology to the plasmid pRS306 [34] was added and the reaction was incubated at 37° C. for an additional 5 minutes. 1 µl of supercoiled pRS306 was then added to the reaction and incubated at 37° C. for 20 minutes; at this point the reaction consisted of 25 mM HEPES-NaOH (pH 7.0), 1 mM ATP, 1 mM MgCl$_2$, 1 mM DTT, 1.5 µM BSA, 4.5% DMSO, 0.5 µM RAD51, 11 mM NaCl, 1% glycerol, 20 nM ssDNA, and 5 nM pRS306. The reactions were de-proteinized with 0.8% SDS and 0.8 mg/ml proteinase K, mixed with gel loading buffer, and run on a 0.9% agarose/1×TAE gel, which was dried and exposed to a phosphor screen overnight and imaged on a Storm 860 PhosphorImager. Compound IC$_{50}$ values were obtained by least-squares regression fitting of appropriate linear, log, or sigmoid dose-response models to the data, with the standard error indicated.

Example 7

Quantitation of HR Efficiency in Cells

293-DR-GFP cells were electroporated in Opti-MEM with 37.5 µg/ml pCBASce in 0.4 cm cuvettes at 325 V, 975 µF and seeded into 6-well plates with 2.5 ml complete DMEM+0.5% DMSO with compound and allowed to outgrow for 24 hours. Following outgrowth, cells were harvested and suspended in PBS with 1 µg/ml 7-aminoactinomycin D (7-AAD) and analyzed on a BD FACSCalibur flow cytometer. Dead and apoptotic cells were gated out based on size, shape, and 7-AAD staining and the fraction of GFP-positive cells among the population of live cells was determined.

Example 8

RAD51 Cytological Focus Formation

Cells were grown on glass coverslips for two days prior to irradiation with X-rays at 1.5 Gy/min using a Philips RT250 Maxitron. Following 6 hours of outgrowth, the adherent cells were incubated in permeabilization buffer (20 mM HEPES-NaOH (pH 7.4), 50 mM NaCl, 3 mM MgCl$_2$, 0.5% Triton X-100, 300 mM sucrose) for 10 minutes at room temperature and then fixed in ice-cold fixation buffer (3% paraformaldehyde, 3.4% sucrose in 1×PBS) for 10 minutes at room temperature. The coverslips were washed 3 times in PBS, incubated in blocking buffer (1% BSA in 1×PBS) for 30 minutes, incubated with rabbit anti-human RAD51 primary antibody (Pacific Immunology) at a 1:1000 dilution in blocking buffer for 18 hours at 4° C., washed 3 times in PBS, incubated with Alexa488-conjugated goat anti-rabbit IgG secondary antibody (Invitrogen) at a 1:1000 dilution in blocking buffer for 1 hour at room temperature, washed 3 times in PBS, air-dried, and mounted onto glass slides in Vectashield with DAPI H-1200 (Vector laboratories). Slides were viewed on a Zeiss Axio Imager.M1 epifluorescence microscope equipped with a CCD camera for acquiring images of at least 100 randomly-selected nuclei per test condition at a representative focal plane within the nuclear volume. Sub-nuclear RAD51 foci were quantified using ImageJ (NIH, Bethesda, Md.) using a custom macro set that automatically counts foci. Plots of RAD51 foci were generated using R software with the optional Bee Swarm package.[35,36]

Example 9

RAD51 D-Loop Inhibitory and RAD51-ssDNA Binding Stimulatory/Inhibitory Activities

TABLE 1

| Activity of Cmpds. 1, 7, and 8 | | | | |
|---|---|---|---|---|
| | D-Loops | | ssDNA binding | |
| Cpd | Max inhibition effect | IC$_{50}$(µM) | Max effect | IC$_{50}$(µM) |
| 1 | 76 ± 4% | 20.0 ± 3.3 | 33 ± 10%↓ | >100 |
| 7 | 17 ± 3% | >100 | 47 ± 33%↑ | Stim |
| 8 | 67 ± 11% | 13.0 ± 4.7 | 40 ± 28%↑ | Stim |

"↑" Indicates that the compound stimulates RAD51-ssDNA binding.
"↓" Compound inhibits RAD51-ssDNA binding.
"Stim" Compound is a stimulator.

TABLE 2

Activity of Cmpds. 9a-j and 11a-d

| Cpd | R | D-Loops Max inhibition effect | D-Loops IC$_{50}$ (μM) | ssDNA binding Max effect | ssDNA binding IC$_{50}$ (μM) |
|---|---|---|---|---|---|
| 9a | 4-N(CH$_3$)$_2$ | 61 ± 4% | 27.6 ± 6.0 | 88 ± 22%↑ | Stim |
| 9b | 3-NO$_2$ | 20 ± 8% | >100 | 52 ± 14%↓ | >100 |
| 9c | 3-NH$_2$ | 79 ± 8% | 91.1 ± 10.3 | 11 ± 9%↓ | >100 |
| 9d | 4-OH | 38 ± 3% | >100 | 14 ± 16%↓ | >100 |
| 9e | 4-OCF$_3$ | 22 ± 8% | >100 | 30 ± 21%↑ | Stim |
| 9f | 4-NO$_2$ | 2 ± 21% | >100 | 16 ± 13%↓ | >100 |
| 9g | 4-NH$_2$ | 100 ± 2% | 22.1 ± 2.4 | 18 ± 11%↓ | >100 |
| 9h | 4-NHEt | 91 ± 2% | 15.8 ± 3.1 | 2 ± 24%↑ | >100 |
| 9i | 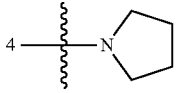 [SMILES: *N1CCCC1] | 8 ± 7% | >100 | 69 ± 35%↑ | Stim |
| 9j | 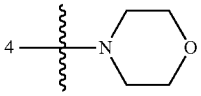 | 68 ± 7% | 27.2 ± 3.0 | 11 ± 19%↓ | >100 |
| 11a | 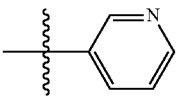 [SMILES: *c1cccnc1] | 70 ± 13% | 71.7 ± 18.1 | 6 ± 10%↓ | >100 |
| 11b | 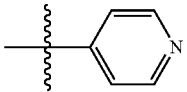 [SMILES: *c1ccncc1] | 63 ± 4% | 79.4 ± 6.0 | 7 ± 38%↓ | >100 |
| 11c | 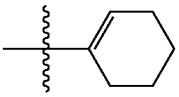 [SMILES: *C1=CCCCC1] | 5 ± 11% | >100 | 42 ± 17%↑ | Stim |
| 11d | 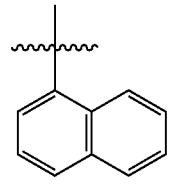 [SMILES: *c1cccc2ccccc12] | 42 ± 11% | >100 | 56 ± 31%↑ | Stim |

↑Compound stimulates RAD51-ssDNA binding.
↓Compound inhibits RAD51-ssDNA binding.
Stim Compound is a stimulator.

TABLE 3

Activity of Cmpds. 12a-m, 13a-b, 15a-b and 16

| Cpd | R$_1$ | R$_2$ | D-Loops Max inhibition effect | D-Loops IC$_{50}$ (μM) | ssDNA binding Max effect | ssDNA binding IC$_{50}$ (μM) |
|---|---|---|---|---|---|---|
| 12a | 7-OCH$_3$ | —OH | 13 ± 12% | >100 | 100 ± 18%↓ | 35.0 ± 14.0 |
| 12b | 7-OCH$_3$ | —NO$_2$ | 17 ± 7% | >100 | 105 ± 47%↑ | Stim |
| 12c | 7-OCH$_3$ | —NH$_2$ | 100 ± 4% | 13.2 ± 2.8 | 29 ± 8%↓ | >100 |
| 12d | 7-OH | —OH | 97 ± 8% | 27.6 ± 4.9 | 72 ± 11%↓ | >100 |

TABLE 3-continued

Activity of Cmpds. 12a-m, 13a-b, 15a-b and 16

| Cpd | $R_1$ | $R_2$ | D-Loops Max inhibition effect | D-Loops $IC_{50}$ (μM) | ssDNA binding Max effect | ssDNA binding $IC_{50}$ (μM) |
|---|---|---|---|---|---|---|
| 12e | 7-OH | —NO$_2$ | 13 ± 10% | >100 | 92 ± 21%↓ | 57.8 ± 3.0 |
| 12f | 7-OH | —NH$_2$ | 100 ± 3% | 8.4 ± 3.4 | 82 ± 23%↓ | 96.9 ± 44.9 |
| 12g | 7-OH | —N(CH$_3$)$_2$ | 91 ± 8% | 9.8 ± 3.5 | 34 ± 32%↑ | Stim |
| 12i | 7-F | —NH$_2$ | 95 ± 6% | 25.0 ± 5.1 | 60 ± 18%↓ | 81.5 ± 16.6 |
| 12j | 7-F | —N(CH$_3$)$_2$ | 31 ± 4% | >100 | 57 ± 28%↑ | Stim |
| 12l | 7,8-diF | —NH$_2$ | 59 ± 4% | 34.0 ± 2.9 | 42 ± 8%↓ | >100 |
| 12m | 7,8-diF | —N(CH$_3$)$_2$ | 19 ± 15% | >100 | 65 ± 22%↑ | Stim |
| 13a | 7-OCH$_3$ | | 74 ± 5% | 38.6 ± 6.2 | 16 ± 28%↓ | >100 |
| 13b | 7-OH | | 53 ± 30% | 64.9 ± 31.6 | 87 ± 10%↓ | >100 |
| 15a | 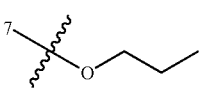 [SMILES: *OCCC] | —NH$_2$ | 75 ± 7% | 46.1 ± 2.8 | 117 ± 18%↑ | Stim |
| 15b | 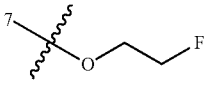 [SMILES: *OCCF] | —NH$_2$ | 98 ± 5% | 20.0 ± 4.1 | 79 ± 23%↑ | Stim |
| 16 | 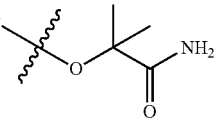 | —N(CH$_3$)$_2$ | 38 ± 4% | >100 | 131 ± 28%↑ | Stim |

↑Compound stimulates RAD51-ssDNA binding.
↓Compound inhibits RAD51-ssDNA binding.
Stim Compound is a stimulator.

Example 10

General Information for Synthetic Procedures

The nuclear magnetic resonance ($^1$H and $^{13}$C NMR) spectra were obtained using a Bruker spectrometer with TMS as an internal standard. Automated column chromatography was performed using the CombiFlash Rf apparatus loaded with Merck silica gel (40-60 mesh). Preparative HPLC was carried out using a Shimadzu preparative liquid chromatograph with a column from ACE 5 AQ (150 mm×21.2 mm) with 5 μm particle size. All solvents used in preparative HPLC were spiked with 0.05% TFA. The purities of biologically important compounds are ≥95% as determined by analytical HPLC (ACE 3AQ C18 column (150 mm×4.6 mm, particle size 3 μM), 0.05% TFA in H$_2$O/0.05% TFA in MeOH gradient eluting system).

Example 11

Synthesis and Activities of the Reduced and Oxidized Forms of 1

As compound 1 was identified from a commercial compound library, its chemical structure was confirmed by carrying out an independent synthesis as detailed in Scheme 1. The starting material 2a was first condensed with dimethoxytetrahydrofuran (3) in refluxing acetic acid to afford 4a. The nitro group of 4a was then reduced, and the aniline 5a was reacted with benzaldehyde 6a in the presence of 1,2,3-benzotriazole and AlCl$_3$ to provide the desired product 7 in low yield.

Scheme 1. Synthesis of 7[a]

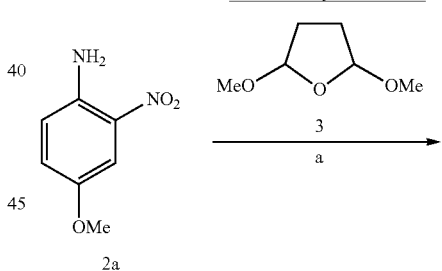

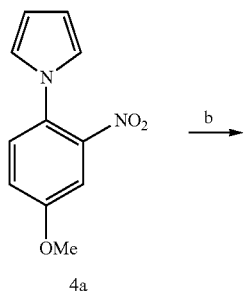

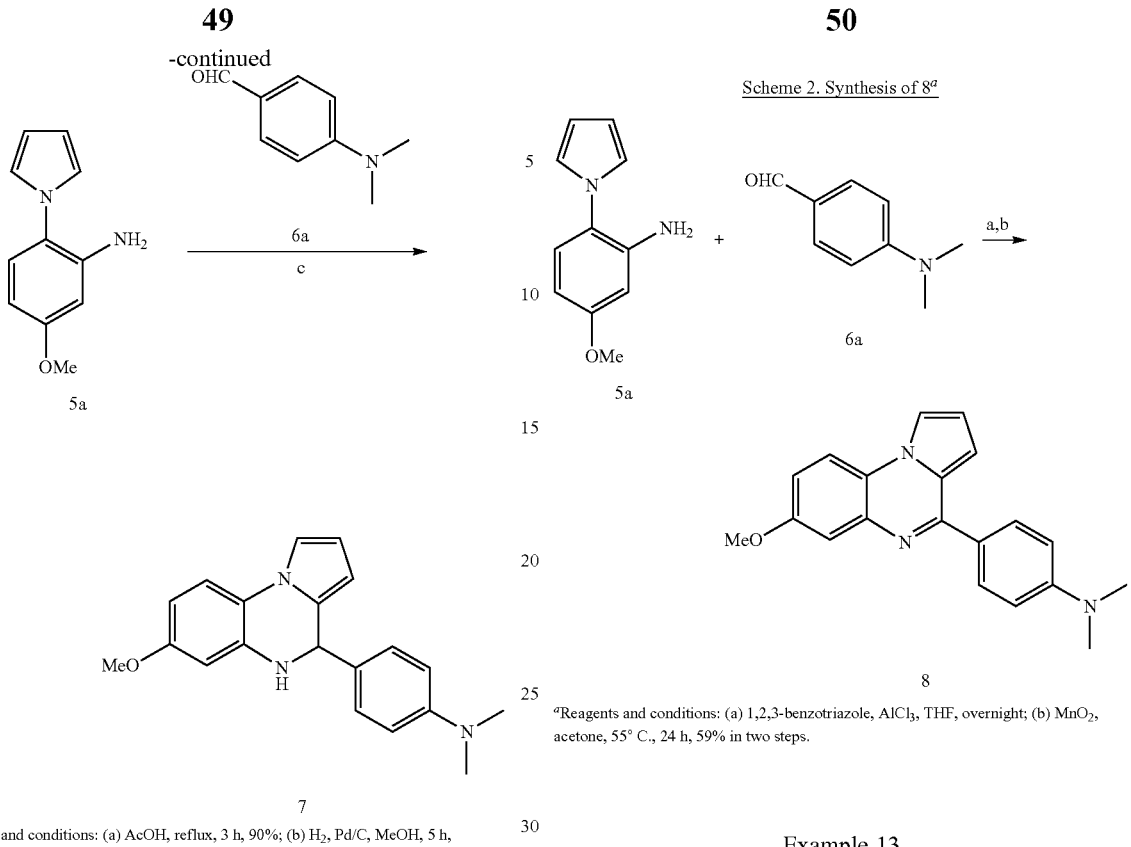

Scheme 2. Synthesis of 8[a]

[a]Reagents and conditions: (a) 1,2,3-benzotriazole, AlCl₃, THF, overnight; (b) MnO₂, acetone, 55° C., 24 h, 59% in two steps.

[a]Reagents and conditions: (a) AcOH, reflux, 3 h, 90%; (b) H₂, Pd/C, MeOH, 5 h, 97%; (c) 1,2,3-benzotriazole, AlCl₃, THF, 4 h, 8%.

The newly synthesized compound 7 was then subjected to biological evaluation as shown in Table 1. Compound 7 displayed a much weaker D-loop inhibitory activity in comparison to the compound 1 obtained from the commercial source (maximum inhibition of 17% for 7 vs 76% for 1). Moreover, compound 7 also showed significant stimulatory activity in RAD51-ssDNA binding when compared to 1 (47% stimulation vs. 30% inhibition). These experimental results signify that compound 7 and 1 are distinct compounds. Compound 7 was not stable when exposed to air at room temperature; instead, it slowly oxidized over time to compound 8 (Scheme 2). Additionally, some of the oxidized product 8 was always produced during the preparation of compound 7.

Example 12

Synthesis of Compound 8

The oxidized form 8 was synthesized by following the route as shown in Scheme 2. The aniline 5a and benzaldehyde 6a were reacted in the presence of 1,2,3-benzotriazole and AlCl₃ at room temperature until the conversion was complete, which resulted in a mixture of the reduced (7) and oxidized (8) forms. This crude mixture was then heated in acetone with MnO₂ to induce further oxidation, thereby yielding the oxidized form 8 as the exclusive product. Subsequent testing in the D-loop assay (Table 1) showed that compound 8 exhibits similar activity to 1 in terms of maximal inhibition (67% vs 76%, respectively) and $IC_{50}$ values (13.0 vs 20.0 μM, respectively). These results thus confirm that the oxidized form 8 is the actual substance that generates the D-loop inhibitory activity of the commercially obtained compound 1.

Example 13

Structure Optimization of 8

To improve upon the D-loop inhibitory activity, medicinal chemical studies were undertaken to optimize 8. An overview of the optimization strategy is summarized in FIG. 4. First, different functional groups were appended to rings A and B as substituents, including alkyl groups of different sizes, electron withdrawing/donating groups, and hydrogen bond donor/acceptor groups. Next, replacement of the phenyl ring B with different heterocycles or other saturated/unsaturated rings was investigated in order to probe its role. For each of the prepared compounds, the gel-based D-loop assay and the microplate-based DNA binding assay were used to characterize the biochemical activities.

Example 14

Optimization of Ring B

To synthesize analogues with different substituents in the B-ring, the aniline 5b was treated with different benzaldehydes 6a-h in the presence of 1,2,3-benzotriazole and AlCl₃ (in Scheme 3). The crude products were then oxidized with MnO₂ to provide 9a-j in good yield. Interestingly, when benzaldehyde 6f was reacted with the aniline 5b under these conditions, partial de-ethylation was observed and the mono-ethylated product 9h was isolated as the major product. The analogues 9c and 9g were obtained by reducing the nitro group of 9b and 9f via hydrogenation. To synthesize analogues in which the B-ring was replaced with other aromatic or saturated rings, the aniline 5b was reacted with different aldehydes 10a-d under similar conditions (in Scheme 4) to afford the products 11a-d in good yield.

Scheme 3. Synthesis of Analogues 11a-d[a]

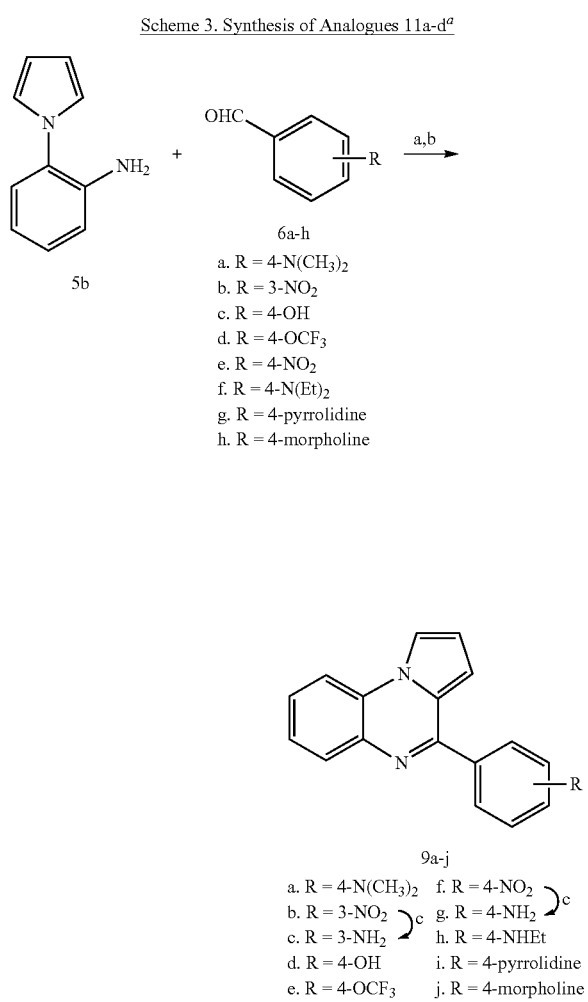

6a-h
a. R = 4-N(CH$_3$)$_2$
b. R = 3-NO$_2$
c. R = 4-OH
d. R = 4-OCF$_3$
e. R = 4-NO$_2$
f. R = 4-N(Et)$_2$
g. R = 4-pyrrolidine
h. R = 4-morpholine 9a-j
a. R = 4-N(CH$_3$)$_2$   f. R = 4-NO$_2$
b. R = 3-NO$_2$   g. R = 4-NH$_2$
c. R = 3-NH$_2$   h. R = 4-NHEt
d. R = 4-OH   i. R = 4-pyrrolidine
e. R = 4-OCF$_3$   j. R = 4-morpholine

[a]Reagents and conditions: (a) 1,2,3-benzotriazole, AlCl$_3$, THF, overnight; (b) MnO$_2$, acetone, 55° C., 24 h, 19-70% in two steps; (c) H$_2$, Pd/C, methanol, 5 h, 57-87%.

Scheme 4. Synthesis of Analogues 11a-d[a]

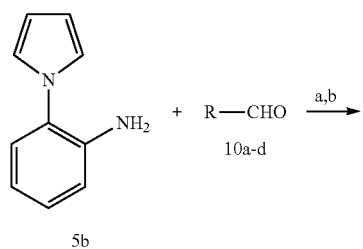 + R—CHO  $\xrightarrow{a,b}$ 10a-d

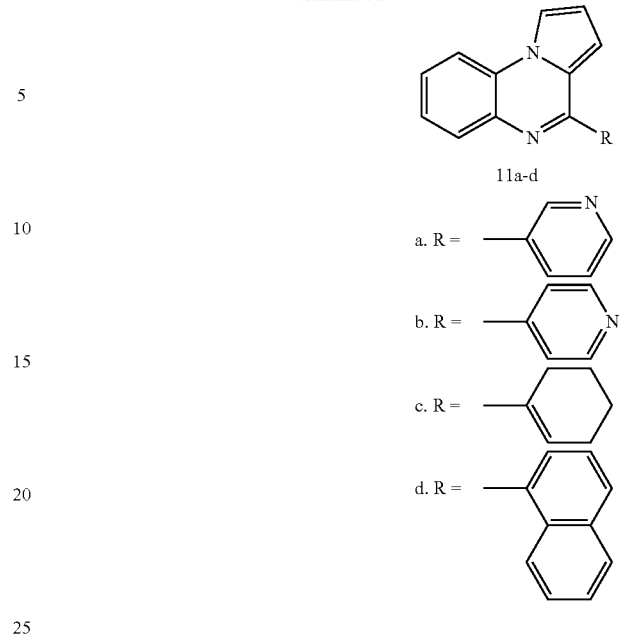

11a-d a. R = (3-pyridyl)
b. R = (pyridyl)
c. R = (cyclohexenyl)
d. R = (naphthyl)

[a]Reagents and conditions: (a) 1,2,3-benzotriazole, AlCl$_3$, THF, overnight; (b) MnO$_2$, acetone, 55° C., 24 h, 35-71% in two steps.

The D-loop inhibitory activities measured for compounds 9a-j and 11a-d are shown in Table 2. Results indicate that a dimethylamino group (9a), amino group (9g), ethylamino group (9h) or morpholine ring (9j) in the para-position of the B-ring allow for D-loop inhibition, and that 9g and 9h display potencies that are similar to that of compound 8. By contrast, introducing a hydroxyl group (9d), trifluoromethoxyl group (9e), nitro group (9f), or pyrrolidine group (9i) in the para-position significantly decreased the D-loop inhibitory activities. Moving the amino group from the para- (9g) to the meta-position (9c) also decreased the D-loop inhibitory activity. Replacing the B-ring with other aromatic or saturated rings only resulted in moderate (11a, 11b) or weak (11c, 11d) D-loop inhibitors. The ability of these analogs to modulate RAD51's ssDNA binding was also evaluated as shown in Table 2. Compounds 9a, 9b, 9i, 11c, and 11d had a modest influence on RAD51-ssDNA binding.

Example 15

Optimization of Ring A

To synthesize analogues with different substituents in the A-ring, the substituted anilines 5b-d were first prepared according to the route shown in Scheme 5. The starting materials 2b-d were condensed with dimethoxytetrahydrofuran (3) in refluxing acetic acid to afford 4b-d. Then, the nitro group was reduced to provide the products 5b-d. Subsequently, the anilines 5a-d were reacted with benzaldehydes (6a, 6c and 6e) to provide the analogues 12a-m in good yield (in Scheme 6). For analogues with an amino group (12c, 12f, 12i and 12l), compounds were prepared from the corresponding nitro analogues (12b, 12e, 12h, 12k) via hydrogenation. Two analogues (13a-b) with a 3-pyridine ring were also prepared from anilines 5a-b and aldehyde 10a as shown in Scheme 7.

Scheme 5. Synthesis of 5b-d[a]

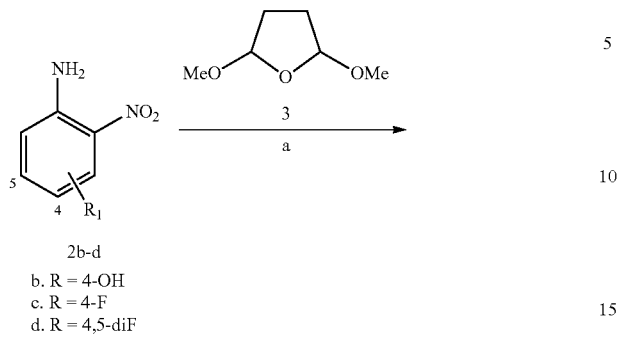

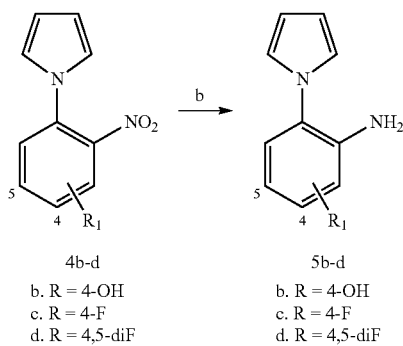

Reagents and conditions: (a) AcOH, reflux, 3 h, 45-63%; (b) H₂, Pd/C, MeOH, 5 h, 37-97%.

Scheme 6. Synthesis of Analogues 12a-m[a]

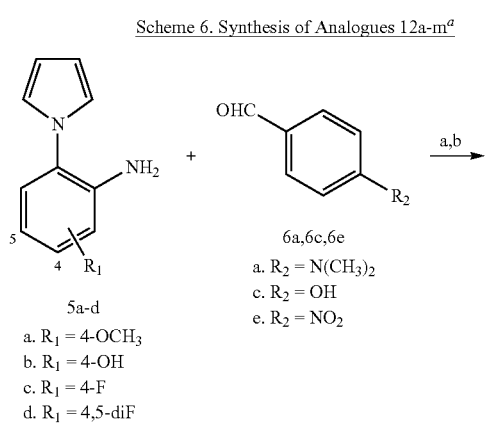

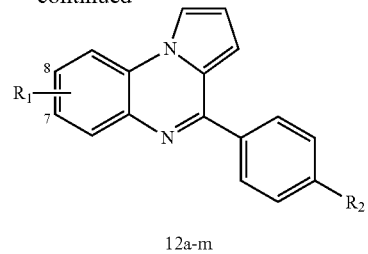

12a-m
a. $R_1$ = 7-OCH$_3$, $R_2$ = OH
b. $R_1$ = 7-OCH$_3$, $R_2$ = NO$_2$ ⎫ c
c. $R_1$ = 7-OCH$_3$, $R_2$ = NH$_2$ ⎭
d. $R_1$ = 7-OH, $R_2$ = OH
e. $R_1$ = 7-OH, $R_2$ = NO$_2$ ⎫ c
f. $R_1$ = 7-OH, $R_2$ = NH$_2$ ⎭
g. $R_1$ = 7-OH, $R_2$ = N(CH$_3$)$_2$
h. $R_1$ = 7-F, $R_2$ = NO$_2$ ⎫ c
i. $R_1$ = 7-F, $R_2$ = NH$_2$ ⎭
j. $R_1$ = 7-F, $R_2$ = N(CH$_3$)$_2$
k. $R_1$ = 7,8-diF, $R_2$ = NO$_2$ ⎫ c
l. $R_1$ = 7,8-diF, $R_2$ = NH$_2$ ⎭
m. $R_1$ = 7,8-diF, $R_2$ = N(CH$_3$)$_2$

Reagents and conditions: (a) 1,2,3-benzotriazole, AlCl₃, THF, overnight; (b) MnO₂, acetone, 55° C., 24 h, 7-77% in two steps; (c) H₂, Pd/C, MeOH, 5 h, 50-93%.

Scheme 7. Synthesis of Analogues 13a-b[a]

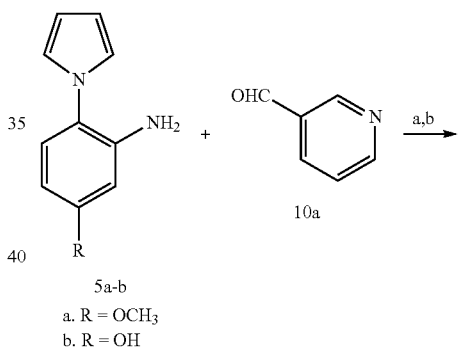

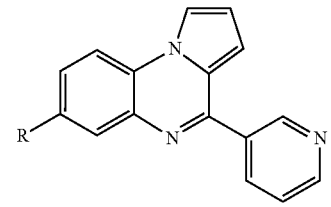

13a-b
a. R = OCH$_3$
b. R = OH

Reagents and conditions: (a) 1,2,3-benzotriazole, AlCl₃, THF, overnight; (b) MnO₂, acetone, 55° C., 24 h, 52-78% in two steps.

To explore the effects of replacing the hydroxyl group of compound 12f with different alkyl groups, compound 12e was first treated with allyl bromide to introduce the allyl group (14a), and then the nitro group was reduced by hydrogenation (in Scheme 8). The side chain double bond was also reduced under these conditions to afford the n-propoxy product 15a. The fluoroethyl compound 15b was prepared in a similar fashion but employed the Mitsunobu reaction to introduce the side chain (in Scheme 8).[25,26] An analogue 16 with a 2-methylpropionamide side chain was also prepared as shown in Scheme 9.

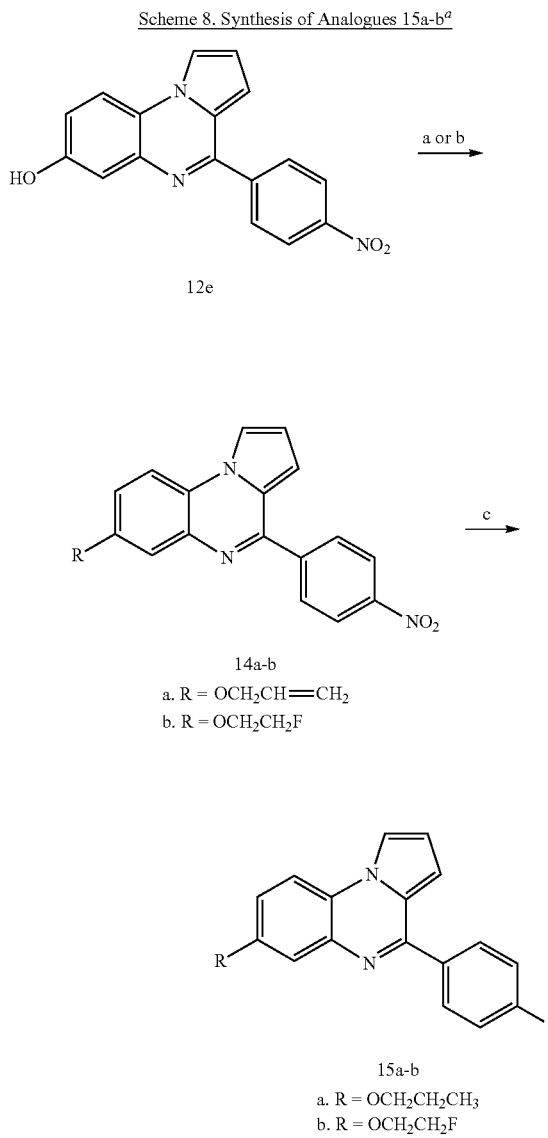

Scheme 8. Synthesis of Analogues 15a-b[a]

14a-b
a. R = OCH$_2$CH=CH$_2$
b. R = OCH$_2$CH$_2$F 15a-b
a. R = OCH$_2$CH$_2$CH$_3$
b. R = OCH$_2$CH$_2$F

Reagents and conditions: (a) allyl bromide, Cs$_2$CO$_3$, DMF, microwave, 80° C., 30 min, 58%; (b) FCH$_2$CH$_2$OH, DEAD, Ph$_3$P, THF, microwave, 60° C., 40 min; (c) H$_2$, Pd/C, MeOH, overnight, 36-45%.

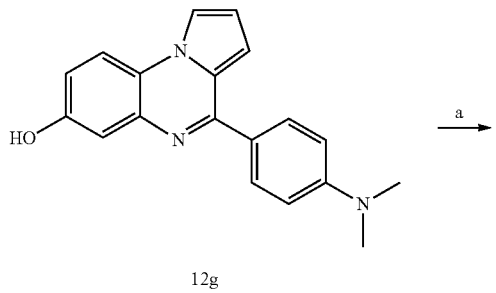

Scheme 9. Synthesis of Analogues 16[a]

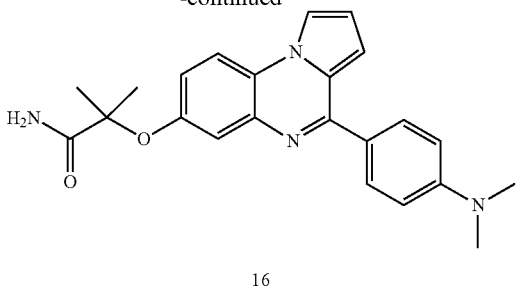

16

Reagents and conditions: (a) Br(CH$_3$)$_2$CHCONH$_2$, NaOH, DMA, 50° C., 3 h, 41%.

The D-loop inhibitory activities for compounds 12a-m, 13a-b, 15a-b and 16 are shown in Table 3. These results indicate that a methoxyl group in the 7 position of A-ring improves its D-loop inhibitory activity, which can be seen by comparing compound 12c (IC$_{50}$ 13.2 µM) against 9g (IC$_{50}$ 22.1 µM). A similar improvement was observed when a hydroxyl group was introduced at the same position (compare 12f, IC$_{50}$ 8.4 µM and 12g, IC$_{50}$ 9.8 µM against 9g, IC$_{50}$ 22.1 µM and 9a, IC$_{50}$ 27.6 µM). In contrast, the introduction of a fluorine atom in the 7 position or two fluorine atoms in the 7 and 8 positions of the A-ring yielded compounds whose D-loop inhibitory potential was moderately diminished (compound 12i IC$_{50}$ 25.0 µM and 12l IC$_{50}$ 34.0 µM) or nearly absent (compound 12j and 12m). For compounds with 3-pyridyl substituents (compound 13a and 13b), the incorporation of a methoxy or hydroxyl group in the A-ring yielded a slight improvement in D-loop inhibition compared with 11a. The appendage of larger alkoxy groups at the 7 position of the A-ring (compounds 15a-b and 16) did not provide more potent D-loop inhibitors (except for compound 15b), when compared to 9g.

The influence of these alterations on RAD51-ssDNA binding activity was also evaluated for these analogs (Table 3). Most of the compounds influenced RAD51-ssDNA binding weakly or modestly, except for compounds 12b, 15a, 15b, and 16, which were stimulators of RAD51-ssDNA binding, and 12a, which showed relatively strong ssDNA binding inhibition. Among the most potent D-loop inhibitors in this series, 12c and 12g only weakly influenced ssDNA-RAD51 binding; 12f and 15b exerted modest effects on ssDNA-RAD51 binding.

Example 16

Cellular Effects of 1 and 9h

The DR-GFP assay was used to test the ability of representative compounds to inhibit HR in human cells.[27] Briefly, cells containing the chromosomal DR-GFP reporter were transfected with a plasmid that expresses I-SceI, a rare-cutting endonuclease that makes a DSB within the DR-GFP cassette. Compounds were added at the time of transfection and the cells were outgrown for 24 hours. For longer outgrowth periods such as 48 hours, cells regained some HR activity. To overcome this technical limitation, the relatively early time point of 24 hours was selected to describe the in vivo effects of these compounds.

Compound 1 is able to inhibit HR activity in human cells. Importantly, 1 yields 50% inhibition of cellular HR activity at 13.1 µM, which is comparable to its observed activity in biochemical assays. Finally, compound 1 permits the timely assembly of RAD51 into sub-nuclear foci in response to DNA damage. This occurs at concentrations of 1 that reduce HR activity to less than 20% that of untreated cells. Taken together, this demonstrates that 1 specifically blocks RAD51's HR activity in human cells without blocking RAD51-ssDNA binding. In fact, a slight increase in steady-state foci levels was observed in irradiated cells treated with 10 to 20 µM of 1, suggesting that 1 may cause RAD51 to form non-functional complexes that accumulate at damaged DNA sites.

The biochemically-derived SAR findings were extended-back into a cell-based system. First, lead compound 1 against was compared against its pure oxidized and pure reduced forms. The HR inhibitory activity of 1 reaches 83% at concentrations of 40 which is a dose where the RAD51-ssDNA binding activity remains unaffected. In contrast to our results using biochemical assays, the inhibitory activity of 7 in the cell-based HR assay was comparable to that of 1 and 8 (FIG. 5a). As noted earlier, 7 spontaneously oxidize to 8. As such, this observed inhibitory activity of 7 is likely caused by its oxidation into the active constituent (8) during the HR assay; such would be expected given the relatively long (24-hour) incubation of 7 in aerated tissue culture medium.

This cell-based HR quantification method was used to evaluate all analogs that exhibited $IC_{50}$ values less than 20 µM in the biochemical D-loop assay. While compounds 12f and 12g had the lowest $IC_{50}$ values in the D-loop assay (even lower than starting compounds 1 and 8), they both yielded comparable or slightly less inhibitory activity in the DR-GFP assay relative to 1 and 8. The most potent inhibitor of cellular HR was 9h, having an $IC_{50}$ of 300±125 nM, which is over an order of magnitude lower than the $IC_{50}$ concentrations of the starting lead compounds 1 and 8 (FIG. 5b). Importantly, 9h did not inhibit the timely assembly of RAD51 into sub-nuclear foci in response to DNA damage, even at concentrations that resulted in more than 90% inhibition of cellular HR (FIGS. 5c-d).

Because 9h inhibits HR-mediated repair of DSBs, the effect of 9h on the sensitization of cancer cells to PARP inhibition or radiation damage was investigated. 9h significantly sensitized 6 different cancer cell lines when administered immediately after veliparib, olaparib, or irradiation and allowed to incubate with cells for the duration of clonogenic outgrowth thereafter (FIGS. 6a-f). Compound 9h is identified as RI(dl)-2, for D-loop activity of RAD51 Inhibitor no. 2.

Example 17

Procedures for the Synthesis of Inhibitors of RAD51 D-Loop Activity

General procedure for preparation of 4a-d. A solution of 2a-d (20 mmol) and 3 (20 mmol) in acetic acid (30 mL) was heated to reflux for 3 h. After cooling down, the mixture was poured into water (150 mL) and extracted with diethyl ether (150 mL×3). The organic layers were combined and dried over $Na_2SO_4$. Solvent was removed provided the crude products of 4a-d.

1-(4-Methoxy-2-nitrophenyl)-1H-pyrrole (4a).[29] The crude product of 4a was further purified by flash silica gel column chromatography (ethyl acetate-hexanes, gradient up to 1:4) to provide the product as orange solid (90%). $^1$H NMR (400 MHz, CDCl$_3$) δ 7.41-7.38 (m, 2H), 7.19-7.16 (m, 1H), 6.76 (s, 2H), 6.35 (s, 2H), 3.92 (s, 3H); $^{13}$C NMR (100 MHz, CDCl$_3$) δ 158.3, 145.6, 129.0, 126.9, 121.4, 118.8, 110.0, 109.1, 55.8.

3-Nitro-4-(1H-pyrrol-1-yl)phenol (4b).[30] The crude product of 4b was further purified by flash silica gel column chromatography (ethyl acetate-hexanes, gradient up to 1:2) to provide the product as orange solid (59%). $^1$H NMR (400 MHz, methanol-d$_4$ and CDCl$_3$) δ 7.25-7.22 (m, 2H), 7.05-7.02 (m, 1H), 6.68 (s, 2H), 6.25 (s, 2H); $^{13}$C NMR (100 MHz, methanol-d$_4$ and CDCl$_3$) δ 156.5, 145.6, 129.0, 125.6, 121.5, 119.8, 110.7, 109.5.

1-(4-Fluoro-2-nitrophenyl)-1H-pyrrole (4c). The crude product of 4c was further purified by flash silica gel column chromatography (ethyl acetate-hexanes, gradient up to 1:7) to provide the product as yellow oil (63%). $^1$H NMR (400 MHz, CDCl$_3$) δ 7.64-7.61 (m, 1H), 7.52-7.48 (m, 1H), 7.43-7.39 (m, 1H), 6.80-6.78 (m, 2H), 6.40-6.38 (m, 2H).

1-(4,5-Difluoro-2-nitrophenyl)-1H-pyrrole (4d). The crude product of 4d was further purified by flash silica gel column chromatography (ethyl acetate-hexanes, gradient up to 1:9) to provide the product as yellow oil (45%). $^1$H NMR (400 MHz, CDCl$_3$) δ 7.85-7.80 (m, 1H), 7.36-7.32 (m, 1H), 6.78-6.76 (m, 2H), 6.40-6.38 (m, 2H).

General procedure for preparation of 5a-d. A suspension of 4a-d (3 mmol) and palladium on charcoal (10%, 60 mg) in methanol (10 mL) was stirred under a hydrogen balloon for 5 h. The black solid was removed by filtration and the filtrate was concentrated to provide the crude product of 5a-d.

5-Methoxy-2-(1H-pyrrol-1-yl)aniline (5a).[29] The crude product of 5a was further purified by flash silica gel column chromatography (ethyl acetate-hexanes, gradient up to 1:4) to provide the product as pale yellow oil (97%). $^1$H NMR (400 MHz, CDCl$_3$) δ 7.13-7.09 (m, 1H), 6.83-6.82 (m, 2H), 6.40-6.37 (m, 4H), 3.84 (s, 3H); $^{13}$C NMR (100 MHz, CDCl$_3$) δ 159.9, 143.4, 128.2, 122.1, 121.2, 109.2, 103.6, 101.1, 55.4.

3-Amino-4-(1H-pyrrol-1-yl)phenol (5b). The crude product of 5b was further purified by flash silica gel column chromatography (ethyl acetate-hexanes, gradient up to 1:2) to provide the product as yellow solid (37%). $^1$H NMR (400 MHz, methanol-d$_4$ and CDCl$_3$) δ 6.93-6.90 (m, 1H), 6.71-6.69 (m, 2H), 6.26-6.24 (m, 3H), 6.22-6.19 (m, 1H); $^{13}$C NMR (100 MHz, methanol-d$_4$ and CDCl$_3$) δ 156.7, 142.9, 127.8, 121.8, 120.1, 108.4, 105.1, 102.0.

5-Fluoro-2-(1H-pyrrol-1-yl)aniline (5c). The crude product of 5c was further purified by flash silica gel column chromatography (ethyl acetate-hexanes, gradient up to 1:7) to provide the product as white solid (97%). $^1$H NMR (400 MHz, CDCl$_3$) δ 7.16-7.12 (m, 1H), 6.85-6.83 (m, 2H), 6.55-6.50 (m, 2H), 6.42-6.41 (m, 2H).

4,5-Difluoro-2-(1H-pyrrol-1-yl)aniline (5d). The crude product 5d was further purified by flash silica gel column chromatography (ethyl acetate-hexanes, gradient up to 1:7) to provide the product as white solid (87%). $^1$H NMR (400 MHz, CDCl$_3$) δ 7.06-7.00 (m, 1H), 6.82-6.80 (m, 2H), 6.62-6.56 (m, 1H), 6.39-6.38 (m, 2H).

4-(7-Methoxy-4,5-dihydropyrrolo[1,2-a][13]quinoxalin-4-yl)-N,N-dimethylaniline (7). A mixture of the aniline 5a (94 mg, 0.50 mmol), the benzaldehydes 6a (75 mg, 0.50 mmol), 1,2,3-benzotriazole (59 mg, 0.50 mmol) and AlCl$_3$ (18 mg, 0.13 mmol) in THF (4 mL) was stirred at room temperature for 4 h. The mixture was diluted with water (15 mL) and extracted with ethyl acetate (15 mL×3). The organic layers were combined, washed with saturated NaHSO$_3$ solutions (15 mL) three times, and then washed with 2 N NaOH aqueous solution (15 mL) and brine (15 mL) sequentially, dried over Na$_2$SO$_4$. The solvent was evaporated, the residue was further purified by flash silica gel column chromatography (ethyl acetate-hexanes, gradient up to 1:3). The purified product was recrystallized in methanol-acetonitrile (1:1, 3 mL) solutions to provide the pure product of 7 as white solid (12.5 mg, 8%). $^1$H NMR (400 MHz, CDCl$_3$) δ 7.35-7.33 (m, 2H), 7.27-7.24 (m, 1H), 7.15-7.13 (m, 1H), 6.76-6.73 (m, 2H), 6.42-6.38 (m, 1H), 6.31-6.30 (m, 1H), 6.25-6.23 (m, 1H), 5.62-5.60 (m, 1H), 5.44 (s, 1H), 4.11 (s, 1H), 3.79 (s, 3H), 2.98 (s, 6H); $^{13}$C NMR (100 MHz, CDCl$_3$) δ 156.6, 150.2, 137.2, 129.8, 128.6, 128.4, 119.5, 115.0, 113.4, 112.0, 109.1, 104.8, 103.7, 100.8, 55.4, 55.0, 40.2; HRESIMS m/z cacld for $C_{20}H_{22}N_3O$ (MH$^+$)

320.1763, found 320.1768. HPLC purity 98.3%, 98.9% (C-18 reverse phase, MeOH—H$_2$O).

General procedure for preparation of 8, 9a-j, 11a-d, 12a-m and 13a-b. A mixture of the aniline (5a-d, 1 mmol), the aldehyde (6a-h or 10a-d, 1 mmol), 1,2,3-benzotriazole (1 mmol) and AlCl$_3$ (0.2 mmol) in THF (4 mL) was stirred at room temperature overnight. The mixture was diluted with water (15 mL) and extracted with ethyl acetate (15 mL×3). The organic layers were combined, washed with 2 N NaOH solution (15 mL) and brine (15 mL) sequentially, and dried over Na$_2$SO$_4$ (for preparation of compounds with phenolic hydroxyl groups, including 9d, 12a, 12d-g and 13b, the organic layers were not washed with NaOH solution, only washed with brine). The solvent was evaporated, the residue was combined with MnO$_2$ (10 mmol) and dissolved with acetone (5 mL). The suspension was heated to 55° C. for 24 h. MnO$_2$ was removed by filtration, and the solvent was evaporated to provide the crude products of 8, 9a-j, 11a-d, 12a-m and 13a-b.

4-(7-Methoxypyrrolo[1,2-a]quinoxalin-4-yl)-N,N-dimethylaniline (8). The aniline 5a and benzaldehyde 6a were reacted according to the general procedure, and the crude product was first purified by flash silica gel column chromatography (ethyl acetate-dichloromethane, gradient up to 3:17), and then further purified by preparative HPLC (with methanol-water, method 1) to afford the products 8 as TFA salt, orange solid (59%). $^1$H NMR (400 MHz, methanol-d$_4$ and CDCl$_3$) δ 8.50-8.49 (m, 1H), 8.06-8.03 (m, 1H), 7.86-7.83 (m, 2H), 7.57-7.55 (m, 1H), 7.43-7.42 (m, 1H), 7.21-7.16 (m, 2H), 6.83-6.80 (m, 2H), 3.88 (s, 3H), 3.12 (s, 6H); $^{13}$C NMR (100 MHz, methanol-d$_4$ and CDCl$_3$) δ 158.3, 153.7, 150.0, 131.0, 126.4, 122.2, 121.9, 119.2, 119.0, 117.9, 117.2, 116.0, 114.3, 111.4, 102.3, 55.2, 39.1; HRESIMS m/z cacld for C$_{20}$H$_{20}$N$_3$O (MH$^+$) 318.1606, found 318.1598. HPLC purity 98.8%, 99.0% (C-18 reverse phase, MeOH—H$_2$O).

N,N-dimethyl-4-(pyrrolo[1,2-a]quinoxalin-4-yl)aniline (9a). The aniline 5b and benzaldehyde 6a were reacted according to the general procedure, and the crude product was purified by flash silica gel column chromatography (ethyl acetate-dichloromethane, gradient up to 1:9) to provide the product 9a as yellow solid (28%). $^1$H NMR (400 MHz, methanol-d$_4$) δ 8.06-8.04 (m, 1H), 7.89-7.87 (m, 1H), 7.82-7.80 (m, 1H), 7.76-7.73 (m, 2H), 7.40-7.33 (m, 2H), 6.94-6.92 (m, 1H), 6.79-6.76 (m, 2H), 2.96 (s, 6H); $^{13}$C NMR (100 MHz, methanol-d$_4$) δ 154.4, 151.9, 135.4, 129.5, 127.9, 126.7, 126.6, 125.1, 124.8, 115.3, 113.7, 111.3, 109.4, 39.0; HRESIMS m/z cacld for C$_{19}$H$_{18}$N$_3$ (MH$^+$) 288.1501, found 288.1506. HPLC purity 98.1%, 98.4% (C-18 reverse phase, MeOH—H$_2$O).

4-(3-Nitrophenyl)pyrrolo[1,2-a]quinoxaline (9b). The aniline 5b and benzaldehyde 6b were reacted according to the general procedure, and the crude product was purified by flash silica gel column chromatography (ethyl acetate-dichloromethane, gradient up to 1:19) to provide the product 9b as light yellow solid (65%). $^1$H NMR (400 MHz, CDCl$_3$) δ 8.93-8.91 (m, 1H), 8.41-8.38 (m, 2H), 8.07-8.04 (m, 2H), 7.94-7.91 (m, 1H), 7.76-7.72 (m, 1H), 7.61-7.57 (m, 1H), 7.53-7.49 (m, 1H), 7.02-7.00 (m, 1H), 6.98-6.95 (m, 1H); $^{13}$C NMR (100 MHz, CDCl$_3$) δ 151.1, 148.1, 139.7, 135.5, 134.1, 130.0, 129.3, 127.9, 126.8, 125.2, 124.3, 124.1, 123.3, 114.8, 114.1, 113.4, 107.8; HRESIMS m/z cacld for C$_{17}$H$_{12}$N$_3$O$_2$ (MH$^+$) 290.0930, found 290.0918. HPLC purity 99.5%, 99.4% (C-18 reverse phase, MeOH—H$_2$O).

4-(Pyrrolo[1,2-a]quinoxalin-4-yl)phenol (9d). The aniline 5b and benzaldehyde 6c were reacted according to the general procedure, and the crude product was first purified by flash silica gel column chromatography (ethyl acetate-dichloromethane, gradient up to 2:3), and then further purified by preparative HPLC (with methanol-water, method 1) to afford the products 9d as TFA salt, yellow solid (57%). $^1$H NMR (400 MHz, methanol-d$_4$) δ 8.87 (s, 1H), 8.40-8.37 (m, 1H), 8.03-8.01 (m, 1H), 7.96-7.94 (m, 2H), 7.82-7.78 (m, 1H), 7.73-7.67 (m, 2H), 7.35-7.33 (m, 1H), 7.15-7.12 (m, 2H); $^{13}$C NMR (100 MHz, methanol-d$_4$) δ 163.0, 151.5, 131.6, 129.6, 127.3, 126.0, 125.8, 124.1, 123.1, 121.0, 120.3, 120.0, 118.6, 116.2, 115.5; HRESIMS m/z cacld for C$_{17}$H$_{13}$N$_2$O (MH$^+$) 261.1028, found 261.1025. HPLC purity 99.5%, 99.5% (C-18 reverse phase, MeOH—H$_2$O).

4-(4-(Trifluoromethoxy)phenyl)pyrrolo[1,2-a]quinoxaline (9e). The aniline 5b and benzaldehyde 6d were reacted according to the general procedure, and the crude product was purified by flash silica gel column chromatography (ethyl acetate-hexanes, gradient up to 1:9) to provide the product 9e as yellow solid (70%). $^1$H NMR (400 MHz, CDCl$_3$) δ 8.08-8.03 (m, 3H), 7.97 (s, 1H), 7.85-7.82 (m, 1H), 7.53-7.40 (m, 4H), 6.97-6.96 (m, 1H), 6.90-6.89 (m, 1H); $^{13}$C NMR (100 MHz, CDCl$_3$) δ 152.7, 150.3, 137.1, 136.1, 130.2, 130.1, 129.9, 127.7, 127.1, 125.3, 125.0, 124.4, 121.0, 120.5 (q, CF$_3$), 116.7, 114.8, 114.1, 113.6, 108.4; HRESIMS m/z cacld for C$_{18}$H$_{12}$N$_2$OF$_3$ (MH$^+$) 329.0902, found 329.0908. HPLC purity 97.3%, 97.1% (C-18 reverse phase, MeOH—H$_2$O).

4-(4-Nitrophenyl)pyrrolo[1,2-a]quinoxaline (9f).[31] The aniline 5b and benzaldehyde 6e were reacted according to the general procedure, and the crude product was purified by flash silica gel column chromatography (ethyl acetate-dichloromethane, gradient up to 1:9) to provide the product 9f as yellow solid (51%). $^1$H NMR (400 MHz, CDCl$_3$) δ 8.43-8.40 (m, 2H), 8.22-8.19 (m, 2H), 8.07-8.05 (m, 2H), 7.94-7.92 (m, 1H), 7.62-7.57 (m, 1H), 7.53-7.49 (m, 1H), 6.97 (s, 2H); $^{13}$C NMR (100 MHz, CDCl$_3$) δ 151.4, 148.2, 144.0, 135.5, 130.1, 129.3, 128.0, 126.8, 125.3, 124.4, 123.4, 114.8, 114.1, 113.4, 107.9; HRESIMS m/z cacld for C$_{17}$H$_{12}$N$_3$O$_2$ (MH$^+$) 290.0930, found 290.0922. HPLC purity 99.0%, 98.1% (C-18 reverse phase, MeOH—H$_2$O).

N-ethyl-4-(pyrrolo[1,2-a]quinoxalin-4-yl)aniline (9h). The aniline 5b and benzaldehyde 6f were reacted according to the general procedure, and the crude product was first purified by flash silica gel column chromatography (ethyl acetate-hexanes, gradient up to 1:3), and then further purified by preparative HPLC (with methanol-water, method 1) to afford the products 9h as TFA salt, red oil (23%). $^1$H NMR (400 MHz, methanol-d$_4$) δ 8.64 (s, 1H), 8.19-8.16 (m, 1H), 7.89-7.87 (m, 1H), 7.80-7.78 (m, 2H), 7.65-7.61 (m, 2H), 7.56-7.52 (m, 1H), 7.21-7.18 (m, 1H), 6.80-6.77 (m, 2H), 3.25 (q, J =7.2 Hz, 2H), 1.31 (t, J=7.2 Hz, 3H); $^{13}$C NMR (100 MHz, methanol-d$_4$) δ 154.1, 150.6, 131.6, 128.7, 127.0, 125.5, 125.3, 123.3, 122.4, 120.2, 119.9, 118.0, 115.2, 114.7, 112.0, 37.1, 13.0; HRESIMS m/z cacld for C$_{19}$H$_{18}$N$_3$ (MH$^+$) 288.1501, found 288.1504. HPLC purity 98.5%, 98.4% (C-18 reverse phase, MeOH—H$_2$O).

4-(4-(Pyrrolidin-1-yl)phenyl)pyrrolo[1,2-a]quinoxaline (9i). The aniline 5b and benzaldehyde 6g were reacted according to the general procedure, and the crude product was first purified by flash silica gel column chromatography (ethyl acetate-hexanes, gradient up to 1:3), and then further purified by preparative HPLC (with methanol-water, method 1) to afford the products 9i as TFA salt, orange solid (61%). $^1$H NMR (400 MHz, methanol-d$_4$) δ 8.63 (s, 1H), 8.17-8.14 (m, 1H), 7.88-7.85 (m, 1H), 7.77-7.74 (m, 2H), 7.63-7.58 (m, 2H), 7.54-7.50 (m, 1H), 7.20-7.17 (m, 1H), 6.60-6.58 (m, 2H), 3.31 (s, 4H), 2.07 (s, 4H); $^{13}$C NMR (100 MHz, methanol-d$_4$) δ 151.7, 150.3, 131.4, 128.6, 127.0, 125.4, 125.2, 123.1, 122.3, 120.2, 119.9, 118.0, 115.1 113.9, 111.7, 47.3, 24.9; HRESIMS m/z cacld for C$_{21}$H$_{20}$N$_3$ (MH$^+$) 314.1657, found 314.1651. HPLC purity 95.6%, 97.7% (C-18 reverse phase, MeOH—H$_2$O).

4-(4-(Pyrrolo[1,2-a]quinoxalin-4-yl)phenyl)morpholine (9j). The aniline 5b and benzaldehyde 6h were reacted according to the general procedure. The crude product was combined with NaBH$_4$ (68 mg, 1.8 mmol), dissolved with methanol (3 mL)-dichloromethane (0.5 mL) mixture solvent, and stirred at room temperature for 3 h. The mixture was diluted with water (10 mL) and extracted with ethyl acetate (10 mL×3). The organic layers were combined and dried over $Na_2SO_4$. Solvent was evaporated and the residues were further purified by flash silica gel column chromatography (ethyl acetate-hexanes, gradient up to 1:2) and the product was recrystallized in acetonitrile to provide the product 9j as yellow solid (19%). $^1H$ NMR (400 MHz, $CDCl_3$) δ 8.04-7.97 (m, 4H), 7.87-7.84 (m, 1H), 7.47-7.44 (m, 2H), 7.06-7.04 (m, 3H), 6.90-6.88 (m, 1H), 3.92-3.87 (m, 4H), 3.32-3.27 (m, 4H); $^{13}C$ NMR (100 MHz, $CDCl_3$) δ 153.5, 152.0, 136.1, 129.6, 129.4, 129.3, 126.6, 126.5, 125.0, 124.8, 114.5, 114.0, 113.4, 113.2, 108.1, 66.4, 48.3. HRESIMS m/z cacld for $C_{21}H_{20}N_3O$ ($MH^+$) 330.1606, found 330.1577. HPLC purity 98.4%, 98.9% (C-18 reverse phase, MeOH—$H_2O$).

4-(Pyridin-3-yl)pyrrolo[1,2-a]quinoxaline (11a). The aniline 5b and aldehyde 10a were reacted according to the general procedure and the crude product was purified by flash silica gel column chromatography (hexane-ethyl acetate, gradient up to 2:3) to provide the product 11a as white solid (64%). $^1H$ NMR (400 MHz, $CDCl_3$) δ 9.26-9.25 (m, 1H), 8.77-8.74 (m, 1H), 8.31-8.29 (m, 1H), 8.02-7.96 (m, 2H), 7.84-7.81 (m, 1H), 7.52-7.41 (m, 3H), 6.96-6.94 (m, 1H), 6.89-6.87 (m, 1H); $^{13}C$ NMR (100 MHz, $CDCl_3$) δ 150.9, 150.2, 149.0, 135.8, 135.6, 133.8, 129.8, 127.6, 126.7, 125.1, 124.5, 123.2, 114.7, 113.9, 113.3, 107.9. HRESIMS m/z cacld for $C_{16}H_{12}N_3$ ($MH^+$) 246.1031, found 246.1038. HPLC purity 99.1%, 98.9% (C-18 reverse phase, MeOH—$H_2O$).

4-(Pyridin-4-yl)pyrrolo[1,2-a]quinoxaline (11b).[31] The aniline 5b and aldehyde 10b were reacted according to the general procedure and the crude product was further purified by flash silica gel column chromatography (ethyl acetate-dichloromethane, gradient up to 7:3) to provide the product 11b as yellow solid (64%). $^1H$ NMR (400 MHz, $CDCl_3$) δ 8.83-8.81 (m, 2H), 8.05-8.02 (m, 2H), 7.91-7.87 (m, 3H), 7.58-7.54 (m, 1H), 7.50-7.46 (m, 1H), 7.00-6.98 (m, 1H), 6.94-6.92 (m, 1H); $^{13}C$ NMR (100 MHz, $CDCl_3$) δ 151.3, 149.9, 145.3, 135.5, 130.1, 127.9, 126.9, 125.1, 124.3, 122.5, 114.7, 114.0, 113.3, 107.8; HRESIMS m/z cacld for $C_{16}H_{12}N_3$ ($MH^+$) 246.1031, found 246.1025. HPLC purity 98.0%, 98.9% (C-18 reverse phase, MeOH—$H_2O$).

4-(Cyclohex-1-en-1-yl)pyrrolo[1,2-a]quinoxaline (11c).[32] The aniline 5b and aldehyde 10c were reacted according to the general procedure and the crude product was further purified by flash silica gel column chromatography (ethyl acetate-hexanes, gradient up to 1:9) to provide the product 11c as pale yellow oil (35%). $^1H$ NMR (400 MHz, $CDCl_3$) δ 7.97-7.94 (m, 1H), 7.92-7.91 (m, 1H), 7.82-7.79 (m, 1H), 7.48-7.40 (m, 2H), 6.98-6.96 (m, 1H), 6.85-6.83 (m, 1H), 6.59-6.57 (m, 1H), 2.69-2.67 (m, 2H), 2.35-2.32 (m, 2H), 1.90-1.86 (m, 2H), 1.82-1.77 (m, 2H); $^{13}C$ NMR (100 MHz, $CDCl_3$) δ 156.2, 136.3, 135.6, 130.8, 129.5, 126.7, 126.6, 124.8, 124.6, 113.8, 113.1, 113.0, 107.8, 26.6, 25.3, 22.4, 21.7; HRESIMS m/z cacld for $C_{17}H_{17}N_2$ ($MH^+$) 249.1392, found 249.1392. HPLC purity 98.8%, 98.9% (C-18 reverse phase, MeOH—$H_2O$).

4-(Naphthalen-1-yl)pyrrolo[1,2-a]quinoxaline (11d).[33] The aniline 5b and aldehyde 10d were reacted according to the general procedure and the crude product was first purified by flash silica gel column chromatography (ethyl acetate-hexanes, gradient up to 3:17), and then further purified by preparative HPLC (with methanol-water, method 0) to afford the products 11d as TFA salt, pale yellow oil (71%). $^1H$ NMR (400 MHz, methanol-$d_4$ and $CDCl_3$) δ 8.50-8.49 (m, 1H), 8.19-8.16 (m, 1H), 8.13-8.11 (m, 2H), 7.99-7.96 (m, 1H), 7.84-7.82 (m, 1H), 7.79-7.72 (m, 2H), 7.67-7.61 (m, 2H), 7.58-7.54 (m, 1H), 7.48-7.44 (m, 1H), 7.13-7.10 (m, 1H), 7.03-7.02 (m, 1H); $^{13}C$ NMR (100 MHz, methanol-$d_4$ and $CDCl_3$) δ 151.6, 133.3, 131.8, 130.4, 129.6, 128.3, 128.2, 128.1, 128.0, 127.2, 127.0, 126.5, 126.2, 124.8, 124.6, 124.1, 121.0, 117.5, 117.2, 114.6. HRESIMS m/z cacld for $C_{21}H_{15}N_2$ ($MH^+$) 295.1235, found 295.1228. HPLC purity 99.4%, 99.7% (C-18 reverse phase, MeOH—$H_2O$).

4-(7-Methoxypyrrolo[1,2-a]quinoxalin-4-yl)phenol (12a). The aniline 5a and benzaldehyde 6c were reacted according to the general procedure and the crude product was first purified by flash silica gel column chromatography (ethyl acetate-hexanes, gradient up to 2:3) and then further purified by preparative HPLC (with methanol-water, method 1) to afford the product 12a as TFA salt, yellow solid (10 mg, 7%). $^1H$ NMR (400 MHz, methanol-$d_4$ and $CDCl_3$) δ 8.74-8.73 (m, 1H), 8.49-8.48 (m, 1H), 8.23-8.19 (m, 1H), 8.15-8.12 (m, 1H), 7.48-7.46 (m, 1H), 7.44-7.41 (m, 1H), 7.34-7.31 (m, 2H), 7.17-7.15 (m, 1H), 3.96 (s, 3H). HRESIMS m/z cacld for $C_{18}H_{15}N_2O_2$ ($MH^+$) 291.1134, found 291.1144. HPLC purity 98.3%, 98.1% (C-18 reverse phase, MeOH—$H_2O$).

7-Methoxy-4-(4-nitrophenyl)pyrrolo[1,2-a]quinoxaline (12b). The aniline 5a and benzaldehyde 6e were reacted according to the general procedure and the crude product was further purified by flash silica gel column chromatography eluted with pure dichloromethane to provide the product 12b as yellow solid (63%). $^1H$ NMR (400 MHz, $CDCl_3$) δ 8.41-8.38 (m, 2H), 8.20-8.17 (m, 2H), 7.99-7.98 (m, 1H), 7.83-7.81 (m, 1H), 7.51-7.50 (m, 1H), 7.21-7.18 (m, 1H), 6.94-6.91 (m, 2H), 3.94 (s, 3H); $^{13}C$ NMR (100 MHz, $CDCl_3$) δ 157.0, 151.7, 148.2, 144.1, 136.6, 129.2, 124.2, 123.4, 121.1, 117.3, 114.4, 114.3, 113.8, 111.1, 107.5, 55.4; HRESIMS m/z cacld for $C_{18}H_{14}N_3O_3$ ($MH^+$) 320.1035, found 320.1020. HPLC purity 96.4%, 97.1% (C-18 reverse phase, MeOH—$H_2O$).

4-(4-Hydroxyphenyl)pyrrolo[1,2-a]quinoxalin-7-ol (12d). The aniline 5b and benzaldehyde 6c were reacted according to the general procedure and the crude product was further purified by flash silica gel column chromatography (ethyl acetate-hexanes, gradient up to 3:2) to provide the product 12d as yellow solid (40%). $^1H$ NMR (400 MHz, methanol-$d_4$) δ 8.14 (s, 1H), 7.93-7.91 (m, 1H), 7.80-7.77 (m, 2H), 7.31-7.30 (m, 1H), 7.06-7.03 (m, 1H), 6.99-6.94 (m, 3H), 6.87-6.85 (m, 1H); $^{13}C$ NMR (100 MHz, methanol-$d_4$) δ 158.9, 154.7, 154.3, 136.1, 129.5, 128.7, 124.2, 120.1, 115.6, 114.8, 114.5, 114.3, 113.0, 111.9, 108.6; HRESIMS m/z cacld for $C_{17}H_{13}N_2O_2$ ($MH^+$) 277.0977, found 277.0983. HPLC purity 96.4%, 96.3% (C-18 reverse phase, MeOH—$H_2O$).

4-(4-Nitrophenyl)pyrrolo[1,2-a]quinoxalin-7-ol (12e). The aniline 5b and benzaldehyde 6e were reacted according to the general procedure and the crude product was first purified by flash silica gel column chromatography (ethyl acetate-dichloromethane, gradient up to 1:3), and then further purified by preparative HPLC (with methanol-water, method 1) to afford the products 12e as TFA salt, yellow solid (49%). $^1H$ NMR (400 MHz, methanol-$d_4$ and $CDCl_3$) δ 8.50-8.47 (m, 2H), 8.43 (s, 1H), 8.17-8.14 (m, 2H), 8.06-8.03 (m, 1H), 7.42-7.41 (m, 1H), 7.26-7.21 (m, 2H), 7.14-7.13 (m, 1H); HRESIMS m/z cacld for $C_{17}H_{12}N_3O_3$ ($MH^+$) 306.0879, found 306.0876. HPLC purity 99.4%, 99.5% (C-18 reverse phase, MeOH—$H_2O$).

4-(4-(Dimethylamino)phenyl)pyrrolo[1,2-a]quinoxalin-7-ol (12g). The aniline 5b and benzaldehyde 6a were reacted according to the general procedure and the crude product was first purified by flash silica gel column chromatography (ethyl acetate-dichloromethane, gradient up to 2:3) and then further purified by preparative HPLC (with methanol-water, method 1) to afford the products 12g as TFA salt, orange solid (25%). $^1H$ NMR (400 MHz, methanol-$d_4$ and $CDCl_3$) δ 8.46 (s, 1H), 8.01-7.99 (m, 1H), 7.88-7.86 (m, 2H), 7.59-7.57 (m, 1H), 7.39-7.37 (m, 1H), 7.19-7.17 (m, 2H), 6.91-6.88 (m, 2H), 3.16 (s, 6H); $^{13}C$ NMR (100 MHz, methanol-$d_4$ and $CDCl_3$) δ 156.6, 153.7, 150.2, 130.9, 126.5, 122.0, 121.9, 118.9, 118.5, 117.8, 116.0, 114.6, 111.5, 104.7, 39.2; HRESIMS m/z cacld for $C_{19}H_{18}N_3O$ ($MH^+$)

304.1450, found 304.1465. HPLC purity 99.0%, 99.5% (C-18 reverse phase, MeOH—H$_2$O).

7-Fluoro-4-(4-nitrophenyl)pyrrolo[1,2-a]quinoxaline (12h). The aniline 5c and benzaldehyde 6e were reacted according to the general procedure and the crude product was further purified by flash silica gel column chromatography (ethyl acetate-dichloromethane, gradient up to 1:19) to provide the product 12h as yellow solid (77%). $^1$H NMR (400 MHz, CDCl$_3$) δ 8.44-8.42 (m, 2H), 8.22-8.20 (m, 2H), 8.05 (s, 1H), 7.92-7.90 (m, 1H), 7.76-7.73 (m, 1H), 7.36-7.32 (m, 1H), 7.00-6.98 (m, 2H). HRESIMS m/z cacld for C$_{17}$H$_{11}$N$_3$O$_2$F (MH$^+$) 308.0835, found 308.0837.

4-(7-Fluoropyrrolo[1,2-a]quinoxalin-4-yl)-N,N-dimethylaniline (12j). The aniline 5c and benzaldehyde 6a were reacted according to the general procedure and the crude product was purified by flash silica gel column chromatography (ethyl acetate-hexanes, gradient up to 1:2) to provide the product 12j as yellow oil (77%). $^1$H NMR (400 MHz, CDCl$_3$) δ 8.01-7.98 (m, 2H), 7.91-7.89 (m, 1H), 7.79-7.75 (m, 1H), 7.71-7.67 (m, 1H), 7.20-7.15 (m, 1H), 7.10-7.08 (m, 1H), 6.88-6.84 (m, 3H), 3.07 (s, 6H). HRESIMS m/z cacld for C$_{19}$H$_{17}$N$_3$F (MH$^+$) 306.1406, found 306.1399. HPLC purity 96.4%, 97.4% (C-18 reverse phase, MeOH—H$_2$O).

7,8-Difluoro-4-(4-nitrophenyl)pyrrolo[1,2-a]quinoxaline (12k). The aniline 5d and benzaldehyde 6e were reacted according to the general procedure and the crude product was further purified by flash silica gel column chromatography (dichloromethane, 100%) to provide the product 12k as yellow solid (41%). $^1$H NMR (400 MHz, CDCl$_3$) δ 8.44-8.41 (m, 2H), 8.20-8.18 (m, 2H), 7.93-7.92 (m, 1H), 7.89-7.84 (m, 1H), 7.74-7.69 (m, 1H), 7.01-6.99 (m, 2H). HRESIMS m/z cacld for C$_{17}$H$_{10}$N$_3$O$_2$F$_2$ (MH$^+$) 326.0741, found 326.0738.

4-(7,8-Difluoropyrrolo[1,2-a]quinoxalin-4-yl)-N,N-dimethylaniline (12m). The aniline 5d and benzaldehyde 6a were reacted according to the general procedure and the crude product was purified by flash silica gel column chromatography (ethyl acetate-hexanes, gradient up to 1:2) to provide the product 12m as yellow solid (50%). $^1$H NMR (400 MHz, CDCl$_3$) δ 7.98-7.95 (m, 2H), 7.81-7.76 (m, 2H), 7.61-7.56 (m, 1H), 7.09-7.07 (m, 1H), 6.89-6.87 (m, 1H), 6.85-6.83 (m, 2H), 3.07 (s, 6H). HRESIMS m/z cacld for C$_{19}$H$_{16}$N$_3$F$_2$ (MH$^+$) 324.1312, found 324.1294. HPLC purity 97.3%, 97.2% (C-18 reverse phase, MeOH—H$_2$O).

7-Methoxy-4-(pyridin-3-yl)pyrrolo[1,2-a]quinoxaline (13a). The aniline 5a and aldehyde 10a were reacted according to the general procedure and the crude product was purified by flash silica gel column chromatography (ethyl acetate-hexanes, gradient up to 95:5) to afford the products 13a as yellow solid (78%). $^1$H NMR (400 MHz, methanol-d$_4$ and CDCl$_3$) δ 9.09-9.08 (m, 1H), 8.69-8.67 (m, 1H), 8.30-8.28 (m, 1H), 7.97-7.96 (m, 1H), 7.77-7.74 (m, 1H), 7.56-7.52 (m, 1H), 7.37-7.35 (m, 1H), 7.09-7.05 (m, 1H), 6.87-6.83 (m, 2H), 3.86 (s, 3H); $^{13}$C NMR (100 MHz, methanol-d$_4$ and CDCl$_3$) δ 156.9, 150.8, 149.6, 148.3, 136.4, 136.1, 133.9, 124.0, 123.5, 121.0, 116.7, 115.0, 114.4, 113.8, 110.3, 107.9, 54.9. HRESIMS m/z cacld for C$_{17}$H$_{14}$N$_3$O (MH$^+$) 276.1137, found 276.1121. HPLC purity 99.4%, 98.7% (C-18 reverse phase, MeOH—H$_2$O).

4-(Pyridin-3-yl)pyrrolo[1,2-a]quinoxalin-7-ol (13b). The aniline 5b and aldehyde 10a were reacted according to the general procedure and the crude product was further purified by flash silica gel column chromatography (first eluted with ethyl acetate-hexanes 1:1, and then switched to methanol-dichloromethane 5:95), to afford the products 13b as yellow solid (52%). $^1$H NMR (400 MHz, methanol-d$_4$ and CDCl$_3$) δ 9.09-9.08 (s, 1H), 8.70-8.68 (m, 1H), 8.32-8.29 (m, 1H), 8.04-8.03 (m, 1H), 7.84-7.81 (m, 1H), 7.59-7.55 (m, 1H), 7.36-7.34 (m, 1H), 7.13-7.09 (m, 1H), 6.90-6.88 (m, 2H); $^{13}$C NMR (100 MHz, methanol-d$_4$ and CDCl$_3$) δ 154.7, 150.9, 149.6, 148.3, 136.4, 136.2, 134.0, 124.1, 123.5, 120.5, 117.0, 115.0, 114.5, 113.7, 112.8, 108.1; HRESIMS m/z cacld for C$_{16}$H$_{12}$N$_3$O (MH$^+$) 262.0980, found 262.0963. HPLC purity 97.0%, 97.0% (C-18 reverse phase, MeOH—H$_2$O).

General procedure for preparation of 9c, 9g, 12c, 12f, 12i and 12l. A suspension of the nitro compound 9b, 9f, 12b, 12e, 12h, or 12k (0.3 mmol) and palladium on charcoal (10%, 20 mg) in methanol (10 mL) was stirred under a hydrogen balloon for 5 h. The solid was removed and the filtrate was concentrated to provide the crude product of 9c, 9g, 12c, 12f, 12i, and 12l.

3-(Pyrrolo[1,2-a]quinoxalin-4-yl)aniline (9c). The compound 9b was reduced by hydrogenation according the general procedure and the crude product was further purified by flash silica gel column chromatography (ethyl acetate-hexanes, gradient up to 3:2) to provide the product 9c as pale yellow oil (57%). $^1$H NMR (400 MHz, methanol-d$_4$) δ 8.14 (s, 1H), 7.97-7.94 (m, 1H), 7.86-7.84 (m, 1H), 7.47-7.43 (m, 1H), 7.40-7.35 (m, 1H), 7.29-7.23 (m, 2H), 7.18-7.15 (m, 1H), 6.95-6.90 (m, 2H), 6.85-6.83 (m, 1H); $^{13}$C NMR (100 MHz, methanol-d$_4$) δ 147.9, 138.5, 135.1, 128.9, 128.3, 127.4, 126.9, 124.9, 117.8, 116.6, 115.6, 114.9, 113.9, 113.8, 109.6; HRESIMS m/z cacld for C$_{17}$H$_{14}$N$_3$ (MH$^+$) 260.1188, found 260.1187. HPLC purity 99.6%, 98.8% (C-18 reverse phase, MeOH—H$_2$O).

4-(Pyrrolo[1,2-a]quinoxalin-4-yl)aniline (9g). The compound 9f was reduced by hydrogenation according the general procedure and the crude product was purified by flash silica gel column chromatography (ethyl acetate-hexanes, gradient up to 3:2) to provide the product 9g as yellow solid (87%). $^1$H NMR (400 MHz, methanol-d$_4$ and CDCl$_3$) δ 8.03-8.02 (m, 1H), 7.89-7.85 (m, 2H), 7.74-7.69 (m, 2H), 7.49-7.36 (m, 2H), 7.02-7.00 (m, 1H), 6.87-6.81 (m, 3H); $^{13}$C NMR (100 MHz, methanol-d$_4$ and CDCl$_3$) δ 154.1, 149.2, 134.5, 129.6, 127.5, 126.8, 126.4, 126.1, 125.0, 124.6, 115.3, 114.2, 113.9, 113.4, 109.9; HRESIMS m/z cacld for C$_{17}$H$_{14}$N$_3$ (MH$^+$) 260.1188, found 260.1170. HPLC purity 99.0%, 98.3% (C-18 reverse phase, MeOH—H$_2$O).

4-(7-Methoxypyrrolo[1,2-a]quinoxalin-4-yl)aniline (12c). The compound 12b was reduced by hydrogenation according the general procedure and the crude product was further purified by flash silica gel column chromatography (ethyl acetate-hexanes, gradient up to 3:2) to provide the product 12c as yellow oil (79%). $^1$H NMR (400 MHz, methanol-d$_4$) δ 7.87-7.86 (m, 1H), 7.66-7.63 (m, 3H), 7.22-7.21 (m, 1H), 6.90-6.87 (m, 1H), 6.85-6.80 (m, 2H), 6.70-6.68 (m, 1H), 3.78 (s, 3H); $^{13}$C NMR (100 MHz, methanol-d$_4$) δ 156.8, 154.3, 149.8, 135.8, 129.3, 126.0, 124.1, 120.5, 114.7, 114.6, 114.1, 113.7, 112.9, 109.1, 108.7, 54.2; HRESIMS m/z cacld for C$_{18}$H$_{16}$N$_3$O (MH$^+$) 290.1293, found 290.1286. HPLC purity 98.7%, 99.5% (C-18 reverse phase, MeOH—H$_2$O).

4-(4-Aminophenyl)pyrrolo[1,2-a]quinoxalin-7-ol (12f). The compound 12e was reduced by hydrogenation according the general procedure and the crude product was purified by preparative HPLC (with methanol-water, method 2) to afford the products 12f as TFA salt, brown oil (50%). $^1$H NMR (400 MHz, methanol-d$_4$) δ 8.54-8.53 (m, 1H), 8.05-8.02 (m, 1H), 7.78-7.75 (m, 2H), 7.57-7.56 (m, 1H), 7.29-7.28 (m, 1H), 7.17-7.15 (m, 1H), 7.12-7.09 (m, 1H), 6.93-6.90 (m, 2H); $^{13}$C NMR (100 MHz, methanol-d$_4$) δ 156.6, 153.5, 150.2, 131.1, 126.3, 122.4, 121.8, 118.7, 118.3, 117.4, 117.3, 116.0, 115.8, 113.9, 104.2; HRESIMS m/z cacld for C$_{17}$H$_{14}$N$_3$O (MH$^+$) 276.1137, found 276.1146. HPLC purity 98.4%, 95.6% (C-18 reverse phase, MeOH—H$_2$O).

4-(7-Fluoropyrrolo[1,2-a]quinoxalin-4-yl)aniline (12i). The compound 12h was reduced by hydrogenation according the general procedure and the crude product was first purified by flash silica gel column chromatography (ethyl acetate-hexanes, gradient up to 1:2), and then further purified by preparative HPLC (with methanol-water, method 1)

to afford the product 12i as TFA salt, yellow solid (74%). $^1$H NMR (400 MHz, methanol-d$_4$) δ 8.75-8.74 (m, 1H), 8.38-8.34 (m, 1H), 7.87-7.84 (m, 2H), 7.73-7.68 (m, 2H), 7.54-7.48 (m, 1H), 7.28-7.26 (m, 1H), 6.93-6.90 (m, 2H). HRESIMS m/z cacld for C$_{17}$H$_{13}$N$_3$F (MH$^+$) 278.1094, found 278.1099. HPLC purity 97.0%, 96.2% (C-18 reverse phase, MeOH—H$_2$O).

4-(7,8-Difluoropyrrolo[1,2-a]quinoxalin-4-yl)aniline (12l). The compound 12k was reduced by hydrogenation according the general procedure and the crude product was further purified by flash silica gel column chromatography (ethyl acetate-hexanes, gradient up to 2:3) to provide the product 12l as yellow solid (93%). $^1$H NMR (400 MHz, methanol-d$_4$ and CDCl$_3$) δ 7.88-7.85 (m, 2H), 7.82-7.77 (m, 2H), 7.65-7.60 (m, 1H), 7.06-7.05 (m, 1H), 6.92-6.89 (m, 1H), 6.84-6.81 (m, 2H). HRESIMS m/z cacld for C$_{17}$H$_{12}$N$_3$F$_2$ (MH$^+$) 296.0999, found 296.1003. HPLC purity 96.5%, 96.2% (C-18 reverse phase, MeOH—H$_2$O).

7-(Allyloxy)-4-(4-nitrophenyl)pyrrolo[1,2-a]quinoxaline (14a). A suspension of 12e (86 mg, 0.282 mmol), allyl bromide (78 mg, 0.64 mmol) and cesium carbonate (136 mg, 0.42 mmol) in dry DMF (2 mL) was heated to 80° C. for 30 min in a microwave reactor under argon. After cooling down, the mixture was diluted with water (20 mL) and extracted with ethyl acetate (20 mL×3). The organic layers were combined and dried over Na$_2$SO$_4$. The solvent was evaporated and the residues were further purified by flash silica gel column chromatography (ethyl acetate-hexanes, gradient up to 1:3) to afford the product 14a as yellow solid (56 mg, 58%). $^1$H NMR (400 MHz, CDCl$_3$) δ 8.41-8.38 (m, 2H), 8.20-8.17 (m, 2H), 7.98-7.97 (m, 1H), 7.83-7.81 (m, 1H), 7.51-7.50 (m, 1H), 7.24-7.21 (m, 1H), 6.94-6.91 (m, 2H), 6.18-6.08 (m, 1H), 5.52-5.47 (m, 1H), 5.37-5.33 (m, 1H), 4.68-4.66 (m, 2H); $^{13}$C NMR (100 MHz, CDCl$_3$) δ 156.0, 151.7, 148.2, 144.1, 136.6, 132.4, 129.2, 124.2, 123.4, 121.2, 117.8, 117.7, 114.4, 114.3, 113.8, 112.2, 107.5, 68.9. HRESIMS m/z cacld for C$_{20}$H$_{16}$N$_3$O$_3$ (MH$^+$) 346.1192, found 346.1162.

4-(7-Propoxypyrrolo[1,2-a]quinoxalin-4-yl)aniline (15a). A suspension of 14a (56 mg, 0.162 mmol) and palladium on charcoal (10%, 18 mg) in methanol (5 mL) was stirred under a hydrogen balloon overnight. The solid was removed and the filtrate was concentrated. The residue was further purified by flash silica gel column chromatography (ethyl acetate-hexanes, gradient up to 3:2) to provide the product 15a as yellow oil (23 mg, 45%). $^1$H NMR (400 MHz, methanol-d$_4$) δ 8.07-8.06 (m, 1H), 7.86-7.84 (m, 1H), 7.71-7.68 (m, 2H), 7.30-7.29 (m, 1H), 7.05-7.02 (m, 1H), 6.96-6.95 (m, 1H), 6.87-6.82 (m, 3H), 4.00-3.96 (m, 2H), 1.85-1.80 (m, 2H), 1.09-1.05 (m, 3H); $^{13}$C NMR (100 MHz, methanol-d$_4$) δ 156.4, 154.4, 149.9, 135.6, 129.3, 125.8, 124.1, 120.5, 115.4, 115.0, 114.3, 113.8, 113.2, 109.8, 109.1, 69.3, 21.8, 9.1. HRESIMS m/z cacld for C$_{20}$H$_{20}$N$_3$O (MH$^+$) 318.1606, found 318.1588. HPLC purity 97.7%, 98.2% (C-18 reverse phase, MeOH—H$_2$O).

4-(7-(2-Fluoroethoxy)pyrrolo[1,2-a]quinoxalin-4-yl)aniline (15b). A solution of 12e (69 mg, 0.226 mmol), 2-fluoroethanol (89 mg, 1.4 mmol) and triphenylphosphine (183 mg, 0.70 mmol) in dry THF (4 mL) was stirred under argon and cooled to 0° C. DEAD (145 mg, 0.83 mmol) was added dropwise. The mixture was warmed to room temperature and heated to 60° C. for 40 min in a microwave reactor. The solvent was evaporated and the residues were further purified by flash silica gel column chromatography (ethyl acetate-hexanes, gradient up to 3:7) to provide the crude product 14b. The crude product 14b was dissolved in methanol (5 mL), and palladium on charcoal (10%, 29 mg) was added. The suspension was stirred under a hydrogen balloon overnight. The solid was removed and the filtrate was concentrated. The residue was further purified by flash silica gel column chromatography (ethyl acetate-hexanes, gradient up to 2:1) to provide the product 15b as yellow oil (26 mg, 36%). $^1$H NMR (400 MHz, methanol-d$_4$) δ 8.02-8.00 (m, 1H), 7.82-7.79 (m, 1H), 7.69-7.67 (m, 2H), 7.29-7.28 (m, 1H), 7.05-7.01 (m, 1H), 6.94-6.92 (m, 1H), 6.85-6.82 (m, 2H), 6.81-6.78 (m, 1H), 4.82-4.80 (m, 1H), 4.70-4.68 (m, 1H), 4.29-4.27 (m, 1H), 4.22-4.20 (m, 1H); $^{13}$C NMR (100 MHz, methanol-d$_4$) δ 155.7, 154.4, 150.0, 135.6, 129.4, 125.7, 124.1, 120.9, 115.2, 115.0, 114.4, 113.7, 113.2, 109.9, 109.1, 82.2, 80.5, 67.3, 67.1. HRESIMS m/z cacld for C$_{19}$H$_{17}$N$_3$OF (MH$^+$) 322.1356, found 322.1330. HPLC purity 97.6%, 97.7% (C-18 reverse phase, MeOH—H$_2$O).

2-((4-(4-(Dimethylamino)phenyl)pyrrolo[1,2-a]quinoxalin-7-yl)oxy)-2-methylpropanamide (16). A solution of 12g (84 mg, 0.28 mmol), NaOH (180 mg, 4.5 mmol) in DMA (3 mL) was stirred at room temperature for 1 h, 2-bromo-2-methylpropanamide (131 mg, 0.789 mmol) was added and the mixture was heated to 50° C. for 3 h. After cooling down, the mixture was diluted with water (12 mL), extracted with ethyl acetate (20 mL×3). The organic layers were combined, washed with brine (20 mL) and dried over Na$_2$SO$_4$. The solvent was evaporated and the residues were further purified by flash silica gel column chromatography (ethyl acetate-hexanes, gradient up to 19:1) and the crude product was further purified by preparative HPLC (with methanol-water, method 1) to afford the product 16 as TFA salt, yellow solid (55 mg, 41%). $^1$H NMR (400 MHz, methanol-d$_4$) δ 8.63-8.62 (m, 1H), 8.20-8.17 (m, 1H), 7.91-7.88 (m, 2H), 7.67-7.65 (m, 1H), 7.54-7.53 (m, 1H), 7.36-7.32 (m, 1H), 7.24-7.22 (m, 1H), 6.94-6.91 (m, 2H), 3.14 (s, 6H), 1.65 (s, 6H); $^{13}$C NMR (100 MHz, methanol-d$_4$) δ 177.3, 153.9, 153.5, 150.3, 131.0, 125.9, 122.8, 122.0, 121.5, 120.5, 119.3, 117.8, 115.9, 114.3, 111.3, 109.6, 81.2, 38.4, 23.8. HRESIMS m/z cacld for C$_{23}$H$_{25}$N$_4$O$_2$ (MH$^+$) 389.1978, found 389.1956. HPLC purity 98.6%, 97.1% (C-18 reverse phase, MeOH—H$_2$O).

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

(1) Thompson, L. H.; Schild, D. Homologous Recombinational Repair of DNA Ensures Mammalian Chromosome Stability. *Mutat. Res.* 2001, 477, 131-153.
(2) Tebbs, R. S.; Zhao, Y.; Tucker, J. D.; Scheerer, J. B.; Siciliano, M. J.; Hwang, M.; Liu, N.; Legerski, R. J.; Thompson, L. H. Correction of Chromosomal Instability and Sensitivity to Diverse Mutagens by a Cloned Cdna of the Xrcc3 DNA Repair Gene. *Proc. Natl. Acad. Sci. U.S.A.* 1995, 92, 6354-6358.
(3) Liu, N.; Lamerdin, J. E.; Tebbs, R. S.; Schild, D.; Tucker, J. D.; Shen, M. R.; Brookman, K. W.; Siciliano, M. J.; Walter, C. A.; Fan, W.; Narayana, L. S.; Zhou, Z. Q.; Adamson, A. W.; Sorensen, K. J.; Chen, D. J.; Jones, N. J.; Thompson, L. H. Xrcc2 and Xrcc3, New Human (3) Rad51-Family Members, Promote Chromosome Stability and Protect against DNA Cross-Links and Other Damages. *Mol. Cell* 1998, 1, 783-793.
(4) Takata, M.; Sasaki, M. S.; Tachiiri, S.; Fukushima, T.; Sonoda, E.; Schild, D.; Thompson, L. H.; Takeda, S. Chromosome Instability and Defective Recombinational Repair in Knockout Mutants of the Five Rad51 Paralogs. *Mol. Cell Biol.* 2001, 21, 2858-2866.
(5) Klein, H. L. The Consequences of Rad51 Overexpression for Normal and Tumor Cells. *DNA Repair (Amst)* 2008, 7, 686-693.
(6) Hine, C. M.; Seluanov, A.; Gorbunova, V. Use of the Rad51 Promoter for Targeted Anti-Cancer Therapy. *Proc. Natl. Acad. Sci. U.S.A.* 2008, 105, 20810-20815.
(7) Vispe, S.; Cazaux, C.; Lesca, C.; Defais, M. Overexpression of Rad51 Protein Stimulates Homologous Recombination and Increases Resistance of Mammalian Cells to Ionizing Radiation. *Nucleic Acids Res.* 1998, 26, 2859-2864.
(8) Slupianek, A.; Schmutte, C.; Tombline, G.; Nieborowska-Skorska, M.; Hoser, G.; Nowicki, M. O.; Pierce, A. J.; Fishel, R.; Skorski, T. Bcr/Abl Regulates Mammalian Reca Homologs, Resulting in Drug Resistance. *Mol. Cell* 2001, 8, 795-806.
(9) Bello, V. E.; Aloyz, R. S.; Christodoulopoulos, G.; Panasci, L. C. Homologous Recombinational Repair Vis-a-Vis Chlorambucil Resistance in Chronic Lymphocytic Leukemia. *Biochem. Pharmacol.* 2002, 63, 1585-1588.
(10) Hansen, L. T.; Lundin, C.; Spang-Thomsen, M.; Petersen, L. N.; Helleday, T. The Role of Rad51 in Etoposide (Vp16) Resistance in Small Cell Lung Cancer. *Int. J. Cancer* 2003, 105, 472-479.
(11) Russell, J. S.; Brady, K.; Burgan, W. E.; Cerra, M. A.; Oswald, K. A.; Camphausen, K.; Tofilon, P. J. Gleevec-Mediated Inhibition of Rad51 Expression and Enhancement of Tumor Cell Radiosensitivity. *Cancer Res.* 2003, 63, 7377-7383.
(12) Ito, M.; Yamamoto, S.; Nimura, K.; Hiraoka, K.; Tamai, K.; Kaneda, Y. Rad51 Sirna Delivered by Hvj Envelope Vector Enhances the Anti-Cancer Effect of Cisplatin. *J. Gene Med.* 2005, 7, 1044-1052.
(13) Budke, B.; Logan, H. L.; Kalin, J. H.; Zelivianskaia, A. S.; Cameron McGuire, W.; Miller, L. L.; Stark, J. M.; Kozikowski, A. P.; Bishop, D. K.; Connell, P. P. Ri-1: A Chemical Inhibitor of Rad51 That Disrupts Homologous Recombination in Human Cells. *Nucleic Acids Res.* 2012, 40, 7347-7357.
(14) Axelle Renodon-Corniere, Pierre Weigel, Magali Le Breton, Fabrice Fleury. *New Potential Therapeutic Approaches by Targeting Rad51-Dependent Homologous Recombination*. New Research Directions in DNA Repair. Prof. Clark Chen, Ed.; InTech: 2013.
(15) Carvalho, J. F.; Kanaar, R. Targeting Homologous Recombination-Mediated DNA Repair in Cancer. *Expert Opin. Ther. Targets* 2014, 18, 427-458.
(16) Huang, F.; Mazin, A. V. Targeting the Homologous Recombination Pathway by Small Molecule Modulators. *Bioorg. Med. Chem. Lett.* 2014, 24, 3006-3013.
(17) Huang, F.; Mazina, O. M.; Zentner, I. J.; Cocklin, S.; Mazin, A. V. Inhibition of Homologous Recombination in Human Cells by Targeting Rad51 Recombinase. *J. Med. Chem.* 2012, 55, 3011-3020.
(18) Ishida, T.; Takizawa, Y.; Kainuma, T.; Inoue, J.; Mikawa, T.; Shibata, T.; Suzuki, H.; Tashiro, S.; Kurumizaka, H. Dids, a Chemical Compound That Inhibits Rad51-Mediated Homologous Pairing and Strand Exchange. *Nucleic Acids Res.* 2009, 37, 3367-3376.
(19) Budke, B.; Kalin, J. H.; Pawlowski, M.; Zelivianskaia, A. S.; Wu, M.; Kozikowski, A. P.; Connell, P. P. An Optimized Rad51 Inhibitor That Disrupts Homologous Recombination without Requiring Michael Acceptor Reactivity. *J. Med. Chem.* 2013, 56, 254-263.
(20) Takaku, M.; Kainuma, T.; Ishida-Takaku, T.; Ishigami, S.; Suzuki, H.; Tashiro, S.; van Soest, R. W.; Nakao, Y.; Kurumizaka, H. Halenaquinone, a Chemical Compound That Specifically Inhibits the Secondary DNA Binding of Rad51. *Genes Cells* 2011, 16, 427-436.
(21) Schlacher, K.; Christ, N.; Siaud, N.; Egashira, A.; Wu, H.; Jasin, M. Double-Strand Break Repair-Independent Role for Brca2 in Blocking Stalled Replication Fork Degradation by Mre11. *Cell* 2011, 145, 529-542.
(22) Ying, S.; Hamdy, F. C.; Helleday, T. Mre11-Dependent Degradation of Stalled DNA Replication Forks Is Prevented by Brca2 and Parp1. *Cancer Res.* 2012, 72, 2814-2821.
(23) Jayathilaka, K.; Sheridan, S. D.; Bold, T. D.; Bochenska, K.; Logan, H. L.; Weichselbaum, R. R.; Bishop, D. K.; Connell, P. P. A Chemical Compound That Stimulates the Human Homologous Recombination Protein Rad51. *Proc. Natl. Acad. Sci. U.S.A.* 2008, 105, 15848-15853.
(24) Budke, B.; Chan, Y. L.; Bishop, D. K.; Connell, P. P. Real-Time Solution Measurement of Rad51- and Reca-Mediated Strand Assimilation without Background Annealing. *Nucleic Acids Res.* 2013, 41, e130.
(25) Cheng, J.; Giguere, P. M.; Onajole, O. K.; Lv, W.; Gaisin, A.; Gunosewoyo, H.; Schmerberg, C. M.; Pogorelov, V. M.; Rodriguiz, R. M.; Vistoli, G.; Wetsel, W. C.; Roth, B. L.; Kozikowski, A. P. Optimization of 2-Phenylcyclopropylmethylamines as Selective Serotonin 2c Receptor Agonists and Their Evaluation as Potential Antipsychotic Agents. *J. Med. Chem.* 2015, 58, 1992-2002.
(26) Cheng, J.; Giguere, P. M.; Lv, W.; Roth, B. L.; Kozikowski, A. P. Design and Synthesis of (2-(5-Chloro-2,2-Dimethyl-2,3-Dihydrobenzofuran-7-Yl)Cyclopropyl) Methanamine as a Selective Serotonin 2c Agonist. *Tetrahedron Lett.* 2015, 56, 3420-3422.
(27) Bennardo, N.; Cheng, A.; Huang, N.; Stark, J. M. Alternative-Nhej Is a Mechanistically Distinct Pathway of Mammalian Chromosome Break Repair. *PLoS Genet.* 2008, 4, e1000110.
(28) Raderschall, E.; Stout, K.; Freier, S.; Suckow, V.; Schweiger, S.; Haaf, T. Elevated Levels of Rad51 Recombination Protein in Tumor Cells. *Cancer Res.* 2002, 62, 219-225.
(29) Guillon, J.; Grellier, P.; Labaied, M.; Sonnet, P.; Leger, J. M.; Deprez-Poulain, R.; Forfar-Bares, I.; Dallemagne, P.; Lemaitre, N.; Pehourcq, F.; Rochette, J.; Sergheraert, C.; Jarry, C. Synthesis, Antimalarial Activity, and Molecular Modeling of New Pyrrolo[1,2-a]Quinoxalines, Bispyrrolo[1,2-a]Quinoxalines, Bispyrido[3,2-E]Pyrrolo [1,2-a]Pyrazines, and Bispyrrolo[1,2-a]Thieno[3,2-E] Pyrazines. *J. Med. Chem.* 2004, 47, 1997-2009.
(30) Campiani, G.; Morelli, E.; Gemma, S.; Nacci, V.; Butini, S.; Hamon, M.; Novellino, E.; Greco, G.; Cagnotto, A.; Goegan, M.; Cervo, L.; Dalla Valle, F.; Fracasso, C.; Caccia, S.; Mennini, T. Pyrroloquinoxaline Derivatives as High-Affinity and Selective 5-Ht(3) Receptor Agonists: Synthesis, Further Structure-Activity Relationships, and Biological Studies. *J. Med. Chem.* 1999, 42, 4362-4379.
(31) Preetam, A.; Nath, M. An Eco-Friendly Pictet-Spengler Approach to Pyrrolo- and Indolo[1,2-a]Quinoxalines Using P-Dodecylbenzenesulfonic Acid as an Efficient Bronsted Acid Catalyst. *RSC Advances* 2015, 5, 21843-21853.
(32) Guillon, J.; Forfar, I.; Mamani-Matsuda, M.; Desplat, V.; Saliege, M.; Thiolat, D.; Massip, S.; Tabourier, A.; Leger, J. M.; Dufaure, B.; Haumont, G.; Jarry, C.; Mossalayi, D. Synthesis, Analytical Behaviour and Biological Evaluation of New 4-Substituted Pyrrolo[1,2-a]Quinoxalines as Antileishmanial Agents. *Bioorg. Med. Chem.* 2007, 15, 194-210.

(33) Wang, C.; Li, Y.; Guo, R.; Tian, J.; Tao, C.; Cheng, B.; Wang, H.; Zhang, J.; Zhai, H. Iodine-Catalyzed Facile Synthesis of Pyrrolo- and Indolo[1,2-a]Quinoxalines. *Asian Journal of Organic Chemistry* 2015, 4, 866-869.
(34) Sikorski, R. S.; Hieter, P. A System of Shuttle Vectors and Yeast Host Strains Designed for Efficient Manipulation of DNA in *Saccharomyces Cerevisiae*. *Genetics* 1989, 122, 19-27.
(35) R Core Team. *R: A Language and Environment for Statistical Computing*, R Foundation for Statistical Computing: 2015.
(36) Eklund, A. *The Bee Swarm Plot, an Alternative to Stripchart.*, 2015.

The invention claimed is:

1. A method for inhibiting RAD51 D-loop-formation activity in a ovarian cell comprising providing to said cell an effective amount of a RAD51 inhibitor, wherein the RAD51 inhibitor is a compound of formula (I):

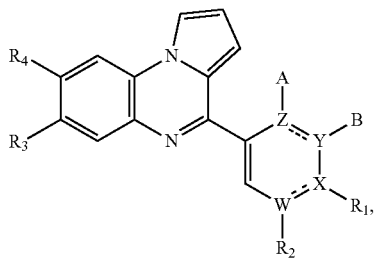

(I)

wherein $R_1$ is hydrogen, hydroxyl, ether, halo-alkyl ether, nitro, amine, alkylamine, dialkylamine, or heterocycle;

$R_2$ is hydrogen, nitro, or amine;

$R_3$ and $R_4$ are independently selected from hydrogen, halogen, hydroxyl, ether, halo-alkyl ether, alkoxyalkyl, or 2-oxy-2-methylpropanamide;

W is C or CH;

X is C, CH, or N;

Y is C, CH, or N;

Z is C or CH; and

A and B are H or join to form a carbocyclic ring;

or a salt, or enantiomer thereof.

2. The method of claim 1, wherein the cancer cell is resistant to chemotherapy or radiation.

3. The method of any of claim 1, wherein the cell is in a patient.

4. The method of claim 3, wherein the patient is a cancer patient.

5. The method of claim 3, wherein the patient has been determined to have chemotherapy- or radiation-resistant cancer.

6. The method of claim 1, wherein the cells have been treated or will be treated with a DNA damaging agent.

7. The method of claim 6, wherein the DNA damaging agent is a cross linking agent, an alkylating agent, nitrosourea, anti-metabolite, plant alkaloid, plant extract, radiation, or radioisotope.

* * * * *

UNITED STATES PATENT AND TRADEMARK OFFICE
CERTIFICATE OF CORRECTION

| | | |
|---|---|---|
| PATENT NO. | : 10,973,819 B2 | |
| APPLICATION NO. | : 16/081662 | |
| DATED | : April 13, 2021 | |
| INVENTOR(S) | : Philip Connell et al. | |

It is certified that error appears in the above-identified patent and that said Letters Patent is hereby corrected as shown below:

In the Specification

On Column 1 at Line 14 insert the following subtitle and paragraph:
-- STATEMENT OF GOVERNMENT SUPPORT
This invention was made with government support under grant number CA142642 awarded by the National Institutes of Health. The government has certain rights in the invention. --

Signed and Sealed this
Thirtieth Day of August, 2022

Katherine Kelly Vidal
*Director of the United States Patent and Trademark Office*